(12) United States Patent
Nakata et al.

(10) Patent No.: US 11,647,775 B2
(45) Date of Patent: May 16, 2023

(54) EMULSION COMPOSITION

(71) Applicant: SAN-EI GEN F.F.I., INC., Toyonaka (JP)

(72) Inventors: Kensuke Nakata, Osaka (JP); Ryoko Tsutsumi, Osaka (JP); Takeshi Miuchi, Osaka (JP); Makoto Sakata, Osaka (JP); Masayuki Nishino, Osaka (JP)

(73) Assignee: SAN-EI GEN F.F.I., INC., Osaka (JP)

( * ) Notice: Subject to any disclaimer, the term of this patent is extended or adjusted under 35 U.S.C. 154(b) by 292 days.

(21) Appl. No.: 16/499,123

(22) PCT Filed: Mar. 30, 2018

(86) PCT No.: PCT/JP2018/013923
§ 371 (c)(1),
(2) Date: Sep. 27, 2019

(87) PCT Pub. No.: WO2018/181998
PCT Pub. Date: Oct. 4, 2018

(65) Prior Publication Data
US 2020/0037648 A1 Feb. 6, 2020

(30) Foreign Application Priority Data

Mar. 31, 2017 (JP) ............................. JP2017-073029
Apr. 17, 2017 (JP) ............................. JP2017-081562

(51) Int. Cl.
| | | |
|---|---|---|
| A23L 29/10 | (2016.01) | |
| A61K 8/06 | (2006.01) | |
| A23L 29/25 | (2016.01) | |
| A23L 2/62 | (2006.01) | |
| A61K 8/73 | (2006.01) | |
| A61K 9/107 | (2006.01) | |
| A61K 47/36 | (2006.01) | |

(52) U.S. Cl.
CPC ............... *A23L 29/10* (2016.08); *A23L 2/62* (2013.01); *A23L 29/25* (2016.08); *A61K 8/06* (2013.01); *A61K 8/73* (2013.01); *A61K 9/107* (2013.01); *A61K 47/36* (2013.01); *A23V 2002/00* (2013.01)

(58) Field of Classification Search
CPC . A23L 29/10; A23L 29/25; A23L 2/62; A61K 8/06; A61K 8/73
See application file for complete search history.

(56) References Cited

U.S. PATENT DOCUMENTS

| | | | |
|---|---|---|---|
| 3,353,961 | A | 11/1967 | Simon et al. |
| 3,891,620 | A | 6/1975 | Cushman et al. |
| 4,581,256 | A | 4/1986 | Sommer |
| 5,725,605 | A | 3/1998 | Maunz et al. |
| 6,477,982 | B1 | 11/2002 | Ritter |
| 8,460,734 | B2 | 6/2013 | Sakata et al. |
| 8,501,209 | B2 | 8/2013 | Oi et al. |
| 8,722,129 | B2 | 5/2014 | Sasaki et al. |
| 8,846,126 | B2 | 9/2014 | Baseeth et al. |
| 9,737,088 | B2 | 8/2017 | Endo et al. |
| 2005/0096464 | A1 | 5/2005 | Heikkila et al. |
| 2005/0124805 | A1 | 6/2005 | Al-Assaf et al. |
| 2007/0031566 | A1 | 2/2007 | Sasaki et al. |
| 2007/0286930 | A1 | 12/2007 | Ogawa et al. |
| 2008/0124437 | A1 | 5/2008 | Fang et al. |
| 2008/0249000 | A1 | 10/2008 | Sakata et al. |
| 2008/0279798 | A1 | 11/2008 | Oi et al. |
| 2009/0004304 | A1 | 1/2009 | Ikehara et al. |
| 2009/0117238 | A1 | 5/2009 | Ido et al. |
| 2010/0020385 | A1 | 1/2010 | Yamamoto et al. |
| 2010/0034956 | A1 | 2/2010 | Kasumi et al. |
| 2011/0033555 | A1 | 2/2011 | Kwetkat et al. |
| 2011/0274812 | A1 | 11/2011 | Nakauma et al. |
| 2012/0100251 | A1 | 4/2012 | Baseeth et al. |
| 2013/0095221 | A1 | 4/2013 | Baseeth et al. |
| 2013/0108763 | A1 | 5/2013 | Saitoh et al. |
| 2013/0115345 | A1 | 5/2013 | Miuchi et al. |
| 2014/0242246 | A9 | 8/2014 | Baseeth et al. |
| 2014/0350125 | A1 | 11/2014 | Merat |
| 2014/0370154 | A1 | 12/2014 | Sakata et al. |
| 2015/0017306 | A1 | 1/2015 | Harada et al. |
| 2015/0045453 | A1 | 2/2015 | Endo et al. |

FOREIGN PATENT DOCUMENTS

| | | |
|---|---|---|
| CN | 1771263 | 5/2006 |
| CN | 1849340 | 10/2006 |
| CN | 1976989 | 6/2007 |
| CN | 101945698 | 1/2011 |
| CN | 102946866 | 2/2013 |
| CN | 102958372 | 3/2013 |

(Continued)

OTHER PUBLICATIONS

International Search Report of PCT/JP2018/013923, dated Jun. 12, 2018, 5 pages including English translation.
International Search Report (Japanese and English) issued for International Application No. PCT/JP2017/035739, dated Dec. 19, 2017, 5 pages.
Ido (SAN-EI GEN F.F.I., INC.), FFI Reports, Foods & Food Ingredients Journal of Japan, 2006, vol. 211, No. 7, pp. 641-645. Description of relevance in the International Search Report of PCT/JP2017/035739.
Amar, V., et al., "The Structure and Function of Arabinogalactan Proteins (AGPs) (2), An Introduction to Gum Ghatti: Another Proteinaceous Gum," Foods & Food Ingredients Journal of Japan, 2006, vol. 211, No. 3, pp. 275-280.

(Continued)

*Primary Examiner* — Yate' K Cutliff
(74) *Attorney, Agent, or Firm* — Hamre, Schumann, Mueller & Larson, P.C.

(57) ABSTRACT

An object of the present invention is to provide an emulsion composition having excellent emulsion stability.
The object is achieved by an emulsion composition comprising an oily component, gum arabic having a molecular weight of not less than 1 million, and a salt, the salt content being 90 parts by mass or less per 100 parts by mass of the gum arabic.

6 Claims, 27 Drawing Sheets

(56) References Cited

FOREIGN PATENT DOCUMENTS

| | | |
|---|---|---|
| CN | 103987372 | 8/2014 |
| CN | 104961840 | 10/2015 |
| EP | 2721933 | 4/2014 |
| JP | H02-042943 | 2/1990 |
| JP | H08-140623 | 6/1996 |
| JP | 2006-257246 | 9/2006 |
| JP | 2006-522202 | 9/2006 |
| JP | 2007-014288 | 1/2007 |
| JP | 2007-049908 | 3/2007 |
| JP | 2007-151480 | 6/2007 |
| JP | 2007-289124 | 11/2007 |
| JP | 2008-013751 | 1/2008 |
| JP | 2008-094806 | 4/2008 |
| JP | 2011-041512 | 3/2011 |
| JP | 2013-009667 | 1/2013 |
| JP | 2014-103957 | 6/2014 |
| JP | 5576539 B1 | 8/2014 |
| JP | 2015-023843 | 2/2015 |
| JP | 2016-187344 | 11/2016 |
| JP | 2016187344 A * | 11/2016 |
| WO | 85/00005 | 1/1985 |
| WO | 2004/089991 | 10/2004 |
| WO | 2005/092930 | 10/2005 |
| WO | 2006/126472 | 11/2006 |
| WO | 2009/001786 | 12/2008 |
| WO | 2009/016362 | 2/2009 |
| WO | 2009/147158 | 12/2009 |
| WO | 2010/082570 | 7/2010 |
| WO | 2011/127163 | 10/2011 |
| WO | 2013/084518 | 6/2013 |
| WO | 2013/146387 | 10/2013 |
| WO | WO2013/146181 | 10/2013 |
| WO | 2017/017248 | 2/2017 |

OTHER PUBLICATIONS

Cheng Liu, et al., "Practical Encyclopedia of Food Additives", Edition 1, 2004, Beijing Industry University Press, p. 580; Cited in the attached Chinese Office Action, English abstract provided.

Zhenyou Ma, et al., "Skin Beauty Cosmetics Preparation Manual", Edition 2, 2015, Ancient Chinese Medicine Books, p. 366; Cited in the attached Chinese Office Action, English abstract provided.

Agricultural Dictionary, Edition 1, 1998, Agricultural Dictionary Editorial Committee, China Agriculture Press, p. 1523; Cited in the attached Chinese Office Action, English abstract provided.

Office Action issued for CN patent application No. 201780060091.X, dated Nov. 3, 2020, 26 pages including English translation.

Ido, T. et al., "Natural Hydrocolloid Emulsifiers (2) Emulsification Properties of GATIFOLIA (Gum Ghatti) Used for Emulsions in Food Products," Foods & Food Ingred J Jpn, 2008, vol. 213, No. 4, pp. 365-371.

International Search Report of PCT/JP2018/044328, dated Feb. 5, 2019, 5 pages including English translation.

Supplementary Extended European Search Report for the related European patent application No. 17856501.6, dated Jan. 18, 2021, 8 pages.

Office Action issued for the corresponding Chinese patent application No. 201880035331.5., dated Jun. 29, 2021, 26 pages including English translation.

Sharma S C, "Gums and Hydrocolloids in Oil-Water Emulsions", Food Technology, 1981, pp. 59-67.

Riaz R A et al., "UTI Lization of Stabilizers and Thickeners as Additives in Food Industry", Science and Industry, 1971, vol. 8, No. 1, pp. 17-21.

Katayama et al., "Natural Hydrocolloid Emulsifiers (2), Characteristics of the Adsorbed Component of Gum Ghatti Responsible for Its Oil-Water Interface Advantages", Shokuhin-Shokuhin-Tenkabutsu-kenkyushi, Foods & Food Ingredients Journal of Japan, 2008, vol. 213, No. 4, pp. 372-376.

The extended European Search Report for the related European patent application No. 18792158.0, dated Apr. 7, 2020, 10 pages.

International Search Report of PCT/JP2018/017285, dated Jul. 17, 2018, 2 pages.

International Preliminary Report on Patentability issued for PCT/JP2018/017285, dated Nov. 7, 2019, 8 pages.

Office Action issued for Chinese Patent Application No. 201780060091.X, dated Apr. 6, 2022, 22 pages including English translation.

Al-Assaf et al., "Characterization of Gum Ghatti and Comparison with Gum Arabic" Royal Society of Chemistry, Special Publication No. 316, pp. 280-290, 2008.

Office Action issued for Korean Patent Application No. 10-2019-7009494, dated May 31, 2022, 10 pages including machine translation.

Office Action issued for Chinese patent application No. 201880035331.5, dated Feb. 17, 2022, 27 pages including English translation.

Office Action issued for Japanese Patent Application No. 2019-514673, dated Mar. 11, 2022, 7 pages including machine translation.

Roberto Buffo et al., "Beverage Emulsions and the Utilization of Gum Acacia as Emulsifier/Stabilizer," Perfumer & Flavorist, 2000, vol. 25, pp. 24-44.

Makoto Nakauma et al., "Comparison of sugar beet pectin, soybean soluble polysaccharide, and gum arabic as food emulsifiers. 1. Effect of concentration, pH, and salts on the emulsifying properties," Food Hydrocolloids, 2008, vol. 22, pp. 1254-1267.

Office Action issued for the corresponding Korean patent application No. 10-2019-7031975, dated Jan. 25, 2023, 10 pages including machine translation.

Office Action issued for the related Japanese patent application No. 2019-069073, dated Mar. 28, 2023, 7 pages including machine translation.

Seiichiro Isobe, "Present situation of ohmic heating in food processing and its possibility in future," Journal of the Japanese Society of Fisheries Science, 2012, vol. 78, No. 4, p. 791; A concise explanation of relevance provdided in the attached English translation of the Japanese Office Action.

Kunihiko Uemura, et al., "Inactivation of Microorganisms in Liquid Foods by High Electric Field Alternating Current," Japanese Society for Food Science and Technology, 2016, vol. 63, No. 5, pp. 185-189; with English Abstract.

Kunihiko Uemura, et al., "Computer fluid dynamics study on heating liquid food by high electric field AC," National Food Research Institute Report of Research, 2007, vol. 71, pp. 27-32; with English Abstract.

* cited by examiner

EMULSION COMPOSITION

TECHNICAL FIELD

The present disclosure relates to an emulsion composition containing gum arabic.

The present disclosure relates to an emulsion composition that can, for example, impart a cloudy appearance, especially to drinks and the like.

BACKGROUND ART

Gum arabic is a polysaccharide thickener obtained from sap of a plant of the genus *Acacia* of the Leguminosae family, and is used to emulsify various oily components such as flavorings, colorants, vitamins, and functional materials.

For example, Patent Literature 1 proposes an emulsion composition containing demetallized gum arabic, an oily substance, and 5 to 30 mass % of ethanol. Further, Patent Literature 2 proposes an emulsion composition containing reformed gum arabic obtained by a heat treatment or a drying treatment at 60° C. or more.

However, there is demand for the development of a composition having more excellent emulsion stability.

It is often preferred by consumers for liquid products, such as drinks, to have a cloudy appearance (or translucent or opaque appearance) (which may be simply referred to as "cloudiness" in the present specification).

Such cloudiness of a drink product is achieved, for example, by incorporating an O/W emulsion into the drink by using a clouding agent.

Such a clouding agent can also impart new properties such as desirable flavor to a drink depending on the component of the oil phase.

For example, as a known clouding agent, Patent Literature 3 proposes a clouding agent based on a combination of a brominated oil and a low-density flavor oil or a plant.

It is desirable that the cloudiness be maintained for a long period of time and/or under harsh conditions in terms of maintaining the quality of drinks.

However, since emulsions are usually a thermodynamically unstable two-phase system, which tends to separate into two immiscible liquids, it is inherently difficult to maintain cloudiness for a long period of time and/or under harsh conditions.

When an emulsion breaks, for example, the oil phase contained in the emulsion may float up and appear as an unsightly ring inside the top of a container enclosing the drink product or conversely may sink and appear as an unsightly precipitate.

A clouding agent capable of imparting stable cloudiness to liquid products such as drinks (i.e., capable of enhancing opacity), particularly a clouding agent whose own stability is also high, is useful.

CITATION LIST

Patent Literature

PTL 1: JP2007-289124A
PTL 2: JP2011-041512A
PTL 3: U.S. Pat. No. 3,353,961

SUMMARY OF INVENTION

Technical Problem

The present disclosure provides an emulsion composition having excellent emulsion stability.

The present disclosure also provides a highly stable emulsion composition that can be used for clouding agents.

Solution to Problem

According to Patent Literature 3, it is known that the emulsifiability of gum arabic is improved by demetallizing (desalting) gum arabic.

However, as a result of extensive research, the present inventors surprisingly found that the stability of an emulsion composition can be improved by adding a specific amount of a salt (e.g. sodium chloride) to gum arabic having a certain molecular weight.

The present invention includes the following embodiments (which may be collectively referred to as "embodiment 1" in the present specification).

Item A1. An emulsion composition comprising:
  water;
  an oily component;
  gum arabic having a molecular weight of not less than 1 million; and
  a salt,
  the salt content being 90 parts by mass or less per 100 parts by mass of the gum arabic.

Item A2. An emulsion composition according to Item A1, wherein the salt content is 0.1 to 90 parts by mass per 100 parts by mass of the gum arabic.

Item A3. The emulsion composition according to Item A1 or A2, wherein the oily component content is in the range of 0.1 to 50 mass %.

Item A4. The emulsion composition according to any one of Items A1 to A3, wherein the oily component content is in the range of 0.1 to 300 parts by mass per 100 parts by mass of the water.

Item A5. The emulsion composition according to any one of Items A1 to A4, wherein the gum arabic content is in the range of 5 to 35 mass %.

Item A6. The emulsion composition according to any one of Items A1 to A5, wherein the gum arabic content is in the range of 10 to 35000 parts by mass per 100 parts by mass of the oily component.

Item A7. The emulsion composition according to any one of Items A1 to A6, wherein the salt is a salt of an element belonging to Group 1 or Group 2 of the periodic table.

Item A8. The emulsion composition according to any one of Items A1 to A7, wherein the salt content is in the range of 0.01 to 10 mass %.

Item A9. The emulsion composition according to any one of Items A1 to A8, further comprising a polyhydric alcohol.

Item A10. The emulsion composition according to Item A9, wherein the polyhydric alcohol is at least one member selected from the group consisting of propylene glycol and glycerin.

Item A11. The emulsion composition according to any one of Items A1 to A10, wherein the emulsion composition is an emulsified flavoring preparation, an emulsified colorant preparation, an emulsified nutrition fortifier preparation, an emulsified functional material preparation, or a clouding agent.

Item A12. An aqueous composition comprising the emulsion composition according to any one of Items A1 to A11.

Item A13. A food or drink comprising the emulsion composition according to any one of Items A1 to A11.

Item A14. The food or drink according to Item A13, wherein the food or drink is a drink.

Item A15. A method for improving the emulsion stability of an emulsion composition comprising water, an oily component, and gum arabic having a molecular weight of not less than 1 million, the method comprising incorporating a salt into the composition, the salt content being 90 parts by mass or less per 100 parts by mass of the gum arabic.

Item A16. The method for improving the emulsion stability of an emulsion composition according to Item A15, wherein the step of incorporating a salt is performed before partial or complete formation of emulsified particles.

The present invention also includes the following embodiments (which may be collectively referred to as "embodiment 2" in the present specification).

Item B1. An emulsion composition comprising: water; an oily component; unmodified or modified gum arabic; and 0.01 mass % or more and less than 10 mass % of a salt, with the proviso that an emulsion composition comprising carnauba wax is excluded.

Item B2. The emulsion composition according to Item B1, wherein the oily component content is in the range of 0.1 to 50 mass %.

Item B3. The emulsion composition according to Item B1 or B2, wherein the oily component content is in the range of 0.1 to 300 parts by mass per 100 parts by mass of the water.

Item B4. The emulsion composition according to any one of Items B1 to B3, wherein the gum arabic content is in the range of 5 to 35 mass %.

Item B5. The emulsion composition according to any one of Items B1 to B4, wherein the gum arabic content is in the range of 10 to 35000 parts by mass per 100 parts by mass of the oily component.

Item B6. The emulsion composition according to any one of Items B1 to B5, wherein the salt is a salt of an element belonging to Group 1 or Group 2 of the periodic table.

Item B7. The emulsion composition according to any one of Items B1 to B6, wherein the salt content is in the range of 0.1 to 90 parts by mass per 100 parts by mass of the gum arabic.

Item B8. The emulsion composition according to any one of Items B1 to B7, further comprising a polyhydric alcohol.

Item B9. The emulsion composition according to Item B8, wherein the polyhydric alcohol is at least one member selected from the group consisting of propylene glycol and glycerin.

Item B10. An emulsified flavoring preparation, emulsified colorant preparation, emulsified nutrition fortifier preparation, emulsified functional material preparation, or clouding agent comprising the emulsion composition according to any one of Items B1 to B9.

Item B11. A food or drink comprising the emulsion composition according to any one of Items B1 to B9.

Item B12. An aqueous composition comprising the emulsion composition according to any one of Items B1 to B9.

Item B13. A method for enhancing the opacity of a drink, the method comprising adding the emulsion composition according to any one of Items B1 to B9 to the drink.

Item B14. A method for improving the emulsion stability of an emulsion composition comprising water, an oily component, and unmodified or modified gum arabic (with the proviso that an emulsion composition comprising carnauba wax is excluded), the method comprising adding a salt to the composition in such an amount that the salt content is 0.01 mass % or more and less than 10 mass %.

Advantageous Effects of Invention

The present invention provides an emulsion composition having excellent emulsion stability.

The present invention also provides an emulsion composition that can be used for clouding agents and exhibits high stability (in particular, emulsion stability).

DESCRIPTION OF EMBODIMENTS

Figure 1:
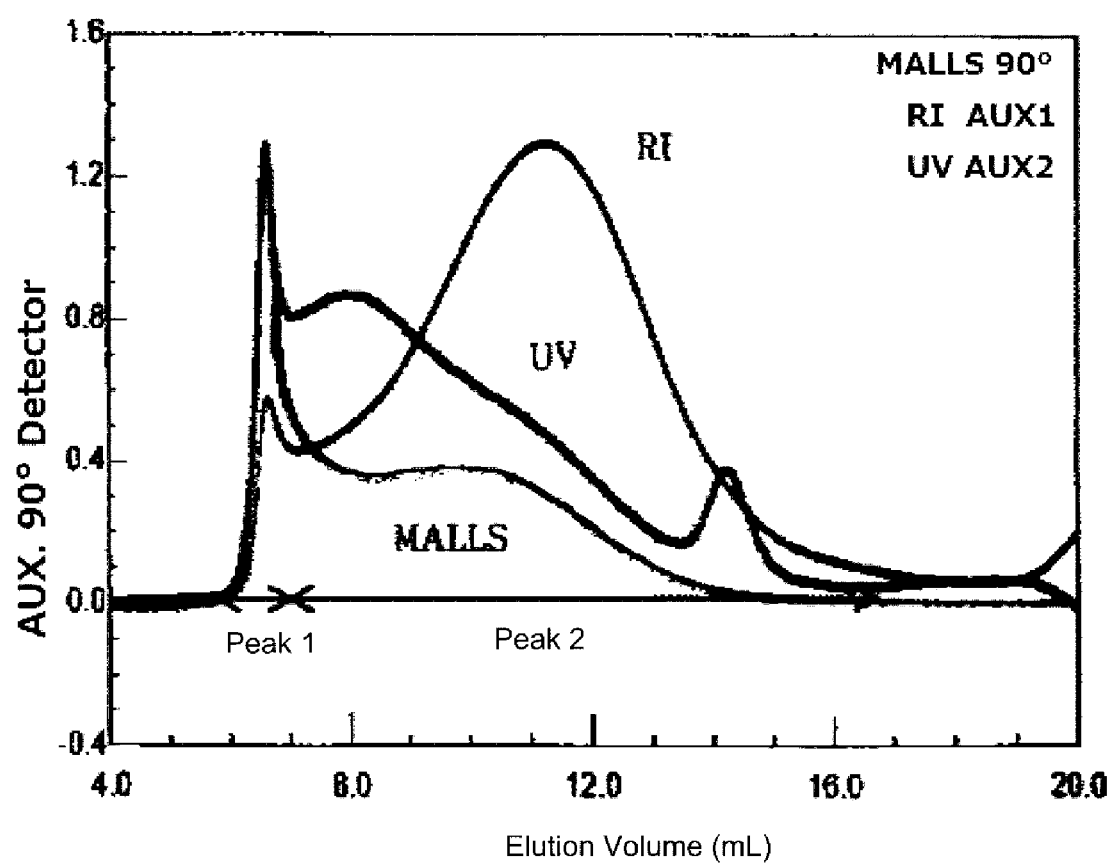
FIG. 1: A chromatogram showing results of analysis of unreformed gum arabic (*Acacia senegal*) by a GPC-MALLS method.

The present invention relates to an emulsion composition. Hereinafter, embodiments of the present invention are described in detail.

In the present specification, the terms "comprise" and "contain" are intended to include the meaning of the term "consist essentially of" and the term "consist of."

Embodiment A

Embodiment A of the present invention is described below.
1. Emulsion Composition The emulsion composition of the present invention comprises:
water;
an oily component;
gum arabic having a molecular weight of not less than 1 million; and
a salt,
the salt content being 90 parts by mass or less per 100 parts by mass of the gum arabic.

Water

Examples of water used in the present invention include pure water, ion-exchanged water, and tap water.

Oily Component

The oily component (component that forms an oil phase) used in the present invention comprises at least one member selected from the group consisting of oil-soluble materials (including liposoluble materials) and oil-based solvents.

Oil-Soluble Material

Examples of oil-soluble materials include, but are not limited to, oil-soluble flavorings, oil-soluble colorants, oil-soluble physiologically active substances, and the like.

Oil-Soluble Flavoring

The oil-soluble flavoring (including liposoluble flavorings; the same applies below) usable in the present invention is not limited as long as the oil-soluble flavoring is an oil-soluble or liposoluble substance containing an aroma component. The oil-soluble flavoring is preferably an edible flavoring that can be added to food or drink, or a flavoring that is applicable to a human body as a cosmetic.

Examples of oil-soluble flavorings include extracts obtained by, for example, extraction with a non-volatile solvent, extraction with a volatile solvent, or supercritical extraction from a natural ingredient derived from an animal or plant; natural flavorings, such as essential oils and recovery essences, obtained by a technique such as steam distillation or a press method; synthetic flavorings synthesized by a chemical technique; and flavoring bases obtained by adding and/or dissolving these flavorings in a fat, an oil, and/or a solvent. Examples of natural flavorings include extracts, such as absolutes, extracts, and oleoresins; essential oils, such as cold-pressed oils; and alcohol extracts called "tincture."

Specific examples of the flavorings include citrus essential oils, such as orange oil, lemon oil, grapefruit oil, lime oil, and mandarin oil; flower oils or absolutes, such as lavender oil; essential oils, such as peppermint oil, spearmint oil, and cinnamon oil; essential oils or oleoresins of spice, such as allspice, anise seed, basil, laurel, cardamom, celery, clove, garlic, ginger, mustard, onion, paprika, parsley, and black pepper; synthetic flavorings, such as limonene, linalool, geraniol, menthol, eugenol, and vanillin; extract oils derived from beans, such as coffee, cacao, vanilla, and roasted peanuts; extracts, such as of black tea, green tea, and oolong tea; and other synthetic flavoring compounds. These flavorings can be used individually, but are typically used as a blended flavoring prepared by combining any two or more flavorings. The term "flavoring" as used herein is defined as including not only flavorings composed of a single compound but also blended flavorings described above.

Oil-Soluble Colorant

The oil-soluble colorant (including liposoluble colorants; the same applies below) usable in the present invention is not limited as long as the oil-soluble colorant is an oil-soluble or liposoluble substance containing a coloring component. The oil-soluble colorant is preferably an edible colorant that can be added to food or drink, or a colorant that is applicable to a human body as a cosmetic.

Examples of oil-soluble colorants include paprika pigment, red pepper pigment, turmeric pigment, annatto pigment, tomato pigment, marigold pigment, *Haematococcus* algae pigment, *Dunaliella* carotene, carrot carotene, palm oil carotene, β-carotene, astaxanthin, canthaxanthin, cryptoxanthin, curcumin, lycopene, lutein, apocarotenal, fucoxanthin, cryptoxanthin, zeaxanthin, capsanthin, capsorubin, norbixin, bixin, chlorophyll, and the like. These oil-soluble colorants may be used singly or in a combination of two or more.

Oil-Soluble Physiologically Active Substance

The oil-soluble physiologically active substance (including liposoluble physiologically active substances; the same applies below) usable in the present invention is not limited as long as the oil-soluble physiologically active substance is an oil-soluble or liposoluble substance that is useful in a living organism.

As will be understood from the above description, an emulsion composition containing the oil-soluble physiologically active substance can be used as, for example, a medicinal agent, a nutrition fortifier (e.g., a vitamin preparation or an amino acid preparation), or a functional material preparation.

The oil-soluble physiologically active substance is preferably an edible substance that can be added to food or drink, or a substance that is applicable to a human body as a cosmetic.

Examples of oil-soluble physiologically active substances include oil-soluble medicinal agents; liposoluble vitamins, such as liver oil, vitamin A (e.g., retinol), vitamin A oil, vitamin D (e.g., ergocalciferol and cholecalciferol), vitamin B2 butyric acid ester, ascorbic acid fatty acid ester, vitamin E (e.g., tocopherol and tocotrienol), and vitamin K (e.g., phylloquinone and menaquinone); plants essential oils, such as limonene, linalool, nerol, citronellol, geraniol, citral, 1-menthol, eugenol, cinnamic aldehyde, anethole, perillaldehyde, vanillin, and γ-undeca lactone; resveratrol, oil-soluble polyphenol, glycosylceramide, sesamin, phosphatidylserine, coenzyme $Q_{10}$, ubiquinol, curcumin, astaxanthin, lutein, and α-lipoic acid; Ω-3 fatty acids, such as α-linolenic acid, eicosapentaenoic acid, and docosahexaenoic acid; Ω-6 fatty acids, such as linoleic acid and γ-linolenic acid; and functional materials, such as plant sterols. Preferable examples include liposoluble vitamins; coenzyme $Q_{10}$; α-lipoic acid; Ω-3 fatty acids, such as α-linolenic acid, eicosapentaenoic acid, and docosahexaenoic acid.

These oil-soluble physiologically active substances may be used singly or in a combination of two or more.

Oil-Based Solvent

The oil-based solvent is not particularly limited as long as the oil-based solvent is usable as a solvent for the oil-soluble material, specifically as long as the oil-based solvent is compatible with the oil-soluble material. The oil-based solvent is preferably an edible substance that can be added to food or drink, or a substance that is applicable to a human body as a cosmetic.

Examples of oil-based solvents include vegetable oils and fats, such as rapeseed oil, corn oil, palm oil, soybean oil, olive oil, jojoba oil, coconut oil, elemi resin, and mastic resin; animal oils and fats, such as beef tallow and lard; sucrose acetate isobutyrate (SAIB); rosin; dammar resin; ester gum; glycerin fatty acid esters; medium-chain triglycerides (MCTs); and the like. These solvents may be used singly or in a combination of two or more.

Preferable examples include glycerin fatty acid esters, triglycerides, sucrose acetate isobutyrate, and vegetable oils and fats. More preferable examples include glycerin fatty acid esters and triglycerides (more preferably medium-chain triglycerides).

Medium-chain triglycerides (MCTs) refer to triacylglycerols composed of medium-chain fatty acids having about 6 to 12 carbon atoms, preferably 6 to 10 carbon atoms, and more preferably 8 to 10 carbon atoms. Commercially available medium-chain triglycerides (MCTs) can be used without any restriction. Specific examples include caprylic triglyceride, capric triglyceride, caprylic and capric triglyceride, and mixtures of these triglycerides.

It is desirable that the emulsion composition of the present invention be substantially free of carnauba wax as an oily component. Specifically, a preferable embodiment of the emulsion composition of the present invention includes an embodiment excluding an emulsion composition containing carnauba wax.

The oily component content in the emulsion composition of the present invention is not particularly limited and is, for example, 0.1 mass % or more, preferably 0.5 mass % or more, more preferably 1 mass % or more, and even more preferably 2 mass % or more. The upper limit of the oily component content is not particularly limited and is, for example, 50 mass % or less, preferably 45 mass % or less, more preferably 40 mass % or less, and even more preferably 35 mass % or less.

The oily component content in the emulsion composition of the present invention is preferably in the range of 0.1 to 300 parts by mass, more preferably 2 to 200 parts by mass, even more preferably 3 to 150 parts by mass, and still even more preferably 4 to 120 parts by mass, per 100 parts by mass of the water.

Gum Arabic

Gum arabic is a polysaccharide derived from sap (secretion) of the genus *Acacia* of the Leguminosae family (in particular, *Acacia senegal* and *Acacia seyal*). The molecular weight of gum arabic obtained by drying the sap is generally less than 1 million (generally, about 200000 to 600000). Gum arabic having the above molecular weight is commonly distributed in the market.

On the other hand, gum arabic having a molecular weight of not less than 1 million is used as gum arabic in the present invention.

The gum arabic used in the present invention includes modified gum arabic and unmodified gum arabic.

The term "modified gum arabic" as used herein means chemically modified gum arabic, in other words, gum arabic having a substituent that natural gum arabic does not have. The term "unmodified gum arabic," which is excluded from this, means chemically unmodified gum arabic, in other words, gum arabic having no substituent that natural gum arabic does not have. Examples of the modified gum arabic include octenylsuccinic acid-modified gum arabic.

The term "unmodified gum arabic" as used herein may be any gum arabic that is not substantially chemically modified, and includes gum arabic that is denatured without chemical modification.

The term "unmodified gum arabic" as used herein may include gum arabic that is not substantially chemically modified. The term "gum arabic that is not substantially chemically modified" means gum arabic that has a small number of substituents that natural gum arabic does not have for some reason (e.g., unintentional contact with a chemical substance), but does not have changed properties due to this compared with gum arabic having no substituent that natural gum arabic does not have in light of the gist of the present invention.

In the present invention, it is desirable to exclude octenylsuccinic acid-modified gum arabic as gum arabic. In the present invention, unmodified gum arabic is preferably used.

The molecular weight of gum arabic in the present invention means a weight average molecular weight.

The weight average molecular weight can be determined by using gel filtration chromatography in which three detectors, i.e., a light scattering (MALLS) detector, a refraction index (RI) detector, and an ultraviolet (UV) detector, are connected online. In the present specification, a technique of such gel filtration chromatography is referred to as "GPC-MALLS." GPC-MALLS operates such that the molecular weight is measured by a MALLS detector, the mass (composition ratio) of each component is measured by an RI detector, and the protein content is measured by a UV detector. Therefore, it is possible to obtain the molecular weights and the compositions of the components to be analyzed without reference to the standard gum arabic having a known molecular weight. Detailed principals and characteristics of the GPC-MALLS can be found in the following Non-Patent Document: Idris, O. H. M., Williams, P. A. Phillips, G. O.; Food Hydrocolloids, 12, (1998) pp. 375-388.

Measurement conditions for GPC-MALLS used in the present invention are as below:

Column: Superose (6HR) 10/30 (Pharmacia Biotech, Sweden)
Flow rate: 0.5 mL/min
Eluant: 0.2 M NaCl
Preparation of a sample: A sample to be analyzed is diluted with the eluant (0.2 M NaCl).
Sample concentration: 0.4% (W/V)

Injection volume of sample solution: 100 μL
dn/dc: 0.141
Temperature: Room temperature
Detector: 1) MALLS (multi-angle laser light scattering) detector: DAWN EOS (produced by Wyatt Technology Inc., USA)
2) RI detector
3) UV detector (absorption at 214 nm)

By processing the data obtained by the GPC-MALLS conducted under the above conditions using, for example, ASTRA Version 4.5 (Wyatt Technology) software, each parameter of the components of the gum arabic, such as the weight average molecular weight, recovery rate (% mass), polydispersity value (P) and root mean square radius of gyration (Rg), can be obtained. When the data is processed for all peaks on the chromatogram obtained using an RI detector as one peak, the obtained molecular weight is identified as the weight average molecular weight ($M_{wt}$) (more specifically, "$M_{wt}$ processed as one peak"). When the point where the RI chart begins to rise from the baseline of the chromatogram is defined as the starting point, and the point where the RI chart falls and intersects the baseline is defined as the ending point, the "one peak" on the chromatogram means the region from the starting point to the ending point.

The molecular weight of gum arabic usable in the present invention is preferably more than 1 million, more preferably not less than 1.1 million, even more preferably not less than 1.2 million, and still even more preferably not less than 1.3 million.

The upper limit of the molecular weight of gum arabic is not particularly limited as long as the gum arabic is soluble in water; however, the molecular weight of gum arabic is, for example, not greater than 5 million, preferably not greater than 4.5 million, and more preferably not greater than 4 million.

Furthermore, the gum arabic usable in the present invention preferably has the above molecular weight and is water-soluble. "Water-soluble" herein means the property that a sample is completely or substantially completely dissolved in an excess of water. "Water" herein means any type of water, e.g., pure water, ion-exchanged water, or ion-containing water. The water temperature may be any suitable temperature as long as the gum arabic is soluble. More specifically, by appropriately setting the type or the temperature of water, any gum arabic dissolvable in water may suitably be used.

The gum arabic having a molecular weight of not less than 1 million can be prepared by subjecting gum arabic as a raw material to a heat treatment at 60° C. or more or a drying treatment at 60° C. or more (which hereinafter may be referred to as "reforming treatment" in the present specification) until the predetermined molecular weight is achieved. Examples of the method include the methods disclosed in JP2000-166489A, WO2003/093324, and WO2005/026213.

Heat treatment using a thermostat or a heater, such as an oven, is a preferred treatment condition. The heating temperature and the heating time are not particularly limited. The heating temperature is, for example, 110 to 130° C., and the heating time is, for example, 10 hours or more, preferably 15 hours or more, 24 hours or more, or 48 hours or more. The upper limit of the heating time depends on the desired molecular weight of gum arabic and is, for example, about 72 hours when heated at 110° C.

As long as it is possible to prepare gum arabic that has the molecular weight specified in the present invention and that is soluble in water, the heating method is not limited to one with the above conditions; the heating temperature, the heating time, the heating means, and the heating environment conditions (e.g., relative humidity, presence or absence of a closed system) can be optionally selected. For example, the effects of the present invention achieved by the heat treatment conducted under the conditions described above can also be obtained by a method in which heating is performed at a temperature lower than 110° C. for more than 10 hours, a method in which heating is performed at a temperature higher than 110° C. for a short time, or the like. Specifically, one example of the former case may be a method in which heating is performed at 80° C. for 3 days to 1 week or longer, or the like. The same effects can be achieved in less time by using microwave radiation instead of a heating means using an oven. In addition, a heat treatment in the absence of oxygen, such as under a nitrogen substitution condition, is a desirable treatment method.

When the gum arabic used in the present invention is gum arabic belonging to *Acacia senegal*, the arabinogalactan protein content is 16 mass % or more, preferably 17 mass % or more, and more preferably 20 mass % or more. The upper limit of the arabinogalactan protein content is not particularly limited as long as the gum arabic is soluble in water. It is desirable that the arabinogalactan protein content be about 30 mass % or less.

Arabinogalactan protein (which may hereinafter simply be referred to as "AGP") is one of three major components of gum arabic along with arabinogalactan (AG) and glycoprotein (GP). Gum arabic having a molecular weight of less than 1 million (*Acacia senegal*) generally contains 5 to 15 mass % of AGP.

The proportion of AGP in gum arabic may be determined by the GPC-MALLS described above. More specifically, when the RI chart of a chromatogram obtained by using an RI detector is divided into two parts, i.e., Peak 1 (high molecular weight elution fraction), which traces the first eluted portion, and Peak 2 (low molecular weight elution fraction), which traces the later eluted portion, and the data are then processed with ASTRA Version 4.5 (Wyatt Technology) software, the obtained recovery ratio of Peak 1 (% mass) corresponds to the AGP content (mass %) of the gum arabic subjected to GPC-MALLS. This is explained in detail with reference to a chromatogram (FIG. 1) showing the results of analysis in which unreformed gum arabic (*Acacia senegal*) was analyzed using GPC-MALLS. The point where the RI chart begins to rise from the baseline of the RI chart is defined as the starting point and the point where the RI chart falls and intersects the baseline is defined as the ending point. Between the starting point and the ending point, the point where the RI value becomes minimum is defined as the boundary, with the region between the starting point and the boundary being defined as Peak 1 and the region between the boundary and the ending point being defined as Peak 2.

The gum arabic used in the present invention may be desalted gum arabic.

The desalted gum arabic is obtained by subjecting gum arabic to a desalting treatment (e.g., a treatment using an electrodialysis membrane or an ion-exchange resin treatment).

As can be understood from this, the desalted gum arabic may be gum arabic in which some or all of the metal atoms or ions thereof are removed.

The desalted gum arabic is commercially available. Examples of commercially available products of the desalted gum arabic include those sold under the trade names such as San Arabic (product name; Sanei-yakuhin Co., Ltd.) and EFISTAB AA (product name; Nexira). Such commercially available products may be used.

The desalted gum arabic may be gum arabic having a metal content of preferably 0 to 100 ppm, and more preferably 0 to 50 ppm.

The desalted gum arabic may be gum arabic prepared by mixing nondesalted gum arabic and desalted gum arabic so that the metal content is in such a range as described above.

A preferable embodiment of the gum arabic used in the present invention includes gum arabic in which the viscosity of an aqueous gum arabic solution (Brix: 25°) measured according to the following conditions is 90 mPa·s or more. The upper limit of the viscosity of the aqueous gum arabic solution (Brix: 25°) is not particularly limited, and is, for example, 300 mPa·s or less.

Conditions for Measuring Viscosity
1) 28 g of gum arabic is added to 70 g of ion-exchanged water (20° C.), and the mixture is stirred to prepare an aqueous gum arabic solution.
2) The aqueous gum arabic solution is allowed to stand (at 5° C. for 18 hours), and the generated bubbles are removed.
3) Ion-exchanged water is appropriately added so that the Brix of the aqueous gum arabic solution is 25°, thereby preparing a 25° Brix aqueous gum arabic solution. This aqueous solution is used as a sample.
4) The viscosity of the sample is measured using a B-type viscometer (type BM; produced by TOKIMEC INC.).
Rotor: No. 2
Rotation rate: 30 rpm
Rotation time: 1 minute A preferable embodiment of the gum arabic used in the present invention includes gum arabic whose b value measured according to the following conditions is 10 or more, and preferably 12 or more. The upper limit of the b value is not particularly limited and is, for example, 30 or less, and preferably 24 or less.

Method for Measuring b Value
1) 28 g of gum arabic is added to 70 g of ion-exchanged water (20° C.), and the mixture is stirred to prepare an aqueous gum arabic solution.
2) The aqueous gum arabic solution is allowed to stand (at 5° C. for 18 hours), and the generated bubbles are removed.
3) Ion-exchanged water is appropriately added so that the Brix of the aqueous gum arabic solution is 10°, thereby preparing a 10° Brix aqueous gum arabic solution. The aqueous solution is used as a sample.
4) The b value of the sample is measured using a spectrophotometer.

Apparatuses etc. used
Measurement for Brix: digital sugar content (concentration) measurement apparatus (PR-101a; produced by Atago Co., Ltd.)
Measurement for b value: ultraviolet-visible spectrophotometer (V-760DS; produced by JASCO Corporation) Measurement conditions: quartz cell (10 mm×10 mm); transmittance (% T)

The amount of gum arabic having a molecular weight of not less than 1 million in the emulsion composition of the present invention is not particularly limited and is, for example, 3 to 40 mass %, preferably 4 to 35 mass %, more preferably 5 to 35 mass %, even more preferably 6 to 30 mass %, still even more preferably 8 to 30 mass %, particularly preferably 10 to 25 mass %, and more particularly preferably 12 to 25 mass %.

It is desirable that the gum arabic content be preferably 10 parts by mass or more, more preferably 30 parts by mass or more, even more preferably 40 parts by mass or more, still even more preferably 50 parts by mass or more, particularly preferably 80 parts by mass or more, more particularly preferably 100 parts by mass or more, even more particularly preferably 120 parts by mass or more, and most preferably 150 parts by mass or more, per 100 parts by mass of the total amount of the oily component in the emulsion composition. The upper limit of the gum arabic content per 100 parts by mass of the total amount of the oily component in the emulsion composition is not particularly limited and is, for example, 35000 parts by mass or less, preferably 10000 parts by mass or less, more preferably 5000 parts by mass or less, even more preferably 1000 parts by mass or less, still even more preferably 600 parts by mass or less, and particularly preferably 500 parts by mass or less.

Salt

In the present invention, use of gum arabic having the molecular weight described above and a predetermined amount of salt in combination enables the emulsion stability of the emulsion composition to be noticeably improved.

The salt used in the present invention is not particularly limited as long as it is a water-soluble salt. Inorganic salts and/or organic acid salts are usable. In the present invention, it is preferable to use an edible inorganic salt and/or organic acid salt.

Moreover, it is preferable to use an inorganic salt in the present invention. Examples of inorganic salts include sodium salts (e.g., sodium chloride), potassium salts (e.g., potassium chloride), calcium salts (e.g., calcium lactate and calcium chloride), magnesium salts (e.g., magnesium chloride), and the like.

Preferable examples of inorganic salts include sodium chloride, potassium chloride, calcium lactate, calcium chloride, and magnesium chloride.

More preferable examples of inorganic salts include sodium chloride, potassium chloride, and magnesium chloride.

Even more preferable examples of inorganic salts include sodium chloride.

These salts may be used singly or in a combination of two or more.

In the present invention, organic acid salts are also usable. Examples of organic acid salts include sodium salts (e.g., sodium citrate and sodium phosphate), potassium salts (e.g., potassium citrate and potassium phosphate), magnesium salts (e.g., magnesium carbonate), and the like.

Preferable examples of organic acid salts include sodium citrate, sodium phosphate, and potassium phosphate.

The emulsion composition of the present invention contains a salt, and the salt content in the emulsion composition is 90 parts by mass or less, preferably 80 parts by mass or less, more preferably 70 parts by mass or less, and even more preferably 60 parts by mass or less, per 100 parts by mass of the gum arabic.

The lower limit of the salt content in the emulsion composition (the salt content per 100 parts by mass of the gum arabic) is not particularly limited and is, for example, 0.05 parts by mass or more, preferably 0.1 parts by mass or more, more preferably 0.5 parts by mass or more, even more preferably 1 part by mass or more, still even more preferably 2 parts by mass or more, particularly preferably 3 parts by mass or more, more particularly preferably 5 parts by mass or more, and most preferably 10 parts by mass or more.

The salt content in the emulsion composition of the present invention is not particularly limited and is, for example, 0.01 mass % or more, preferably 0.05 mass % or more, more preferably 0.1 mass % or more, even preferably 0.5 mass % or more, still even more preferably 1 mass % or more, particularly preferably 1.5 mass % or more, and more particularly preferably 2 mass % or more.

The upper limit of the salt content in the emulsion composition is also not particularly limited and is, for example, 15 mass % or less, preferably 12 mass % or less, more preferably less than 10 mass %, even more preferably 9 mass % or less, still even more preferably 8 mass % or less, and particularly preferably 7 mass % or less.

When desalted gum arabic is used as the gum arabic, the amount of organic acid salt in the emulsion composition may suitably exceed 1 part by mass.

When desalted gum arabic is used, it may be suitably used in combination with an inorganic salt.

Polyhydric Alcohol

The emulsion composition of the present invention may contain a polyhydric alcohol. Use of a polyhydric alcohol improves the storage stability of an emulsion composition and enables an emulsion composition having a high antiseptic effect to be provided.

Examples of polyhydric alcohols usable in the present invention include glycerin, diglycerin, triglycerin, polyglycerin, propylene glycol, dipropylene glycol, 1,3-butylene glycol, ethylene glycol, polyethylene glycol, sorbitol (D-sorbitol), xylitol, maltitol, erythritol, mannitol, xylose, glucose, lactose, mannose, oligotose, high-fructose corn syrup, sucrose, and the like. These polyhydric alcohols may be used singly or in a combination of two or more.

Propylene glycol and/or glycerin is a preferable polyhydric alcohol in the present invention.

When propylene glycol is used as a polyhydric alcohol, the lower limit of the propylene glycol content in the emulsion composition of the present invention may be, for example, 3 mass %, 5 mass %, 10 mass %, 15 mass %, 20 mass %, 30 mass %, 35 mass %, 40 mass %, 45 mass %, or 50 mass %.

When propylene glycol is used as a polyhydric alcohol, the upper limit of the propylene glycol content in the emulsion composition of the present invention may be, for example, 65 mass %, 60 mass %, 55 mass %, 50 mass %, 45 mass %, 40 mass %, or 35 mass %.

The polyhydric alcohol content in the emulsion composition of the present invention is not particularly limited and is, for example, 3 to 80 mass %, preferably 5 to 60 mass %, more preferably 6 to 50 mass %, and even more preferably 8 to 45 mass %.

When propylene glycol is used as a polyhydric alcohol, the propylene glycol content in the emulsion composition of the present invention may be in the range of 3 to 40 mass %, preferably 5 to 30 mass %, more preferably 8 to 25 mass %, and even more preferably 10 to 20 mass %.

When glycerin is used as a polyhydric alcohol, the lower limit of the glycerin content in the emulsion composition of the present invention may be, for example, 5 mass %, 10 mass %, 15 mass %, 20 mass %, 30 mass %, 35 mass %, 40 mass %, 45 mass %, or 50 mass %.

When glycerin is used as a polyhydric alcohol, the upper limit of the glycerin content in the emulsion composition of the present invention may be, for example, 80 mass %, 70 mass %, 60 mass %, 55 mass %, 50 mass %, or 45 mass %.

When glycerin is used as a polyhydric alcohol, the glycerin content in the emulsion composition of the present invention may be in the range of 5 to 80 mass %, preferably 10 to 70 mass %, more preferably 15 to 60 mass %, even more preferably 20 to 50 mass %, and still even more preferably 25 to 45 mass %.

As described above, incorporating a polyhydric alcohol into an emulsion composition has advantages in that the storage stability of an emulsion composition can be improved and an emulsion composition having a high antiseptic effect can be provided. However, use of a polyhydric alcohol causes a decrease in the emulsion stability of an emulsion composition.

Thus, in the present invention, an emulsion composition having excellent emulsion stability, even though it contains a polyhydric alcohol, can be provided by incorporating gum arabic having a molecular weight of not less than 1 million and a salt in an amount of 90 parts by mass or less per 100 parts by mass of the gum arabic.

Preservatives, such as sodium benzoate and potassium sorbate, are generally used in conventional emulsion compositions from the viewpoint of an antiseptic effect. However, use of such preservatives adversely affects the flavor of an emulsion composition. These preservatives have a problem in that although they are effective against certain bacteria and/or fungi, there are bacteria and/or fungi that the preservatives are not effective against. Further, due to recent health consciousness of consumers, use of preservatives tends to be avoided.

From this viewpoint, it is desirable that the emulsion composition of the present invention be substantially free of preservatives. The present invention can provide an emulsion composition having an excellent antiseptic effect and emulsion stability even if the composition is substantially free of preservatives.

pH

The emulsion composition of the present invention preferably has a pH in the range of 2 to 7, more preferably 2 to 6, even more preferably 2 to 4.5, still even more preferably 2 to 4, particularly preferably 2.2 to 3.8, and more particularly preferably 2.5 to 3.5. When the pH is in this range, the stability of the emulsion composition is further improved, and an emulsion composition having a high antiseptic effect can be provided.

To adjust the pH of the emulsion composition to the above range, an organic acid and/or an inorganic acid may be used as necessary. The type of organic acid and/or inorganic acid is not particularly limited.

Examples of organic acids and/or inorganic acids include citric acid, phytic acid, ascorbic acid, phosphoric acid, lactic acid, adipic acid, gluconic acid, succinic acid, acetic acid, tartaric acid, fumaric acid, malic acid, pyrophosphoric acid, and the like. These organic acids and/or inorganic acids may be used singly or in a combination of two or more.

The organic acid and/or inorganic acid in the present invention is preferably at least one member selected from the group consisting of citric acid, phytic acid, ascorbic acid, phosphoric acid, and lactic acid.

The emulsion composition of the present invention may contain as one or more other optional components a water-soluble vitamin, a thickening stabilizer, an antioxidant, a chelating agent, an oxidation inhibitor, or the like as long as the effects of the present invention are not impaired.

The emulsion composition of the present invention may contain ethanol as long as the effects of the present invention are not impaired.

Emulsion Stability

The emulsion composition of the present invention has the advantage of excellent emulsion stability.

The term "emulsion stability" as used herein includes emulsifiability (ease of forming emulsified particles), emulsion storage stability (stability of emulsified particles during storage), and emulsion physical stability (stability of emulsified particles against external physical force).

Method for Preparing Emulsion Composition

The emulsion composition according to the present invention can be prepared by a method comprising mixing an oily component and an aqueous phase containing water, gum arabic having a molecular weight of not less than 1 million, and the predetermined amount of salt.

The means or method, and the conditions for mixing, are not limited as long as water, an oily component, gum arabic having a molecular weight of not less than 1 million, and the predetermined amount of salt are mixed. Mixing itself may be an emulsification treatment, or mixing may be accompanied by an emulsification treatment.

Mixing the components of the emulsion composition and an emulsification treatment may be performed in any order. For example, as the operation of the method for preparing the emulsion composition, the following methods can be used:

(1) a method comprising:
mixing all of and/or the total amount of the components of the emulsion composition; and then performing an emulsification treatment;

(2) a method comprising:
mixing part of and/or a partial amount of the components of the emulsion composition;
performing an emulsification treatment;
adding the remainder of the components of the emulsion composition; and
then further performing an emulsification treatment;

(3) a method comprising mixing all of and/or the total amount of the components of the emulsion composition by an emulsification treatment; or (4) a method comprising:
mixing part of and/or a partial amount of the components of the emulsion composition by an emulsification treatment;
adding the remainder of and/or the remaining amount of the components of the emulsion composition; and
then further mixing the components by an emulsification treatment.

The emulsification treatment may be performed with an emulsifying machine, such as a homogenizer (e.g., a high-pressure homogenizer, a homogenizing disperser, a homo-mixer, a Polytron stirrer, a colloid mill, and a Nanomizer). The conditions for the emulsification treatment can be suitably determined, depending on the type of emulsifying machine used.

For the emulsion composition of the present invention, it is desirable that an emulsification treatment be performed after mixing water, an oily component, gum arabic having a molecular weight of not less than 1 million, and a salt in an amount of 90 parts by mass or less per 100 parts by mass of the gum arabic.

The method for preparing the emulsion composition according to the present invention includes the following preferable embodiment:

A method for preparing an emulsion composition, comprising:
preparing a mixture containing water, an oily component, gum arabic having a molecular weight of not less than 1 million, and a salt, the salt content being 90 parts by mass or less per 100 parts by mass of the gum arabic; and
subjecting the mixture to an emulsification treatment.

The method for preparing the emulsion composition according to the present invention also includes the following preferable embodiment:

A method for preparing an emulsion composition, comprising:
(step 1) preparing an aqueous phase containing water, gum arabic having a molecular weight of not less than 1 million, and a salt, the salt content being 90 parts by mass or less per 100 parts by mass of the gum arabic;
(step 2) preparing a mixture of the aqueous phase and an oily component; and
(step 3) subjecting the mixture to an emulsification treatment.

The form of the emulsion composition of the present invention is not particularly limited. For example, the emulsion composition may be in a liquid form or may be provided as an emulsion composition in a powder form by a powderization means. The powderization means can be performed according to a usual method, and, for example, a means such as spray drying or freeze drying may be used. For powderization, an appropriate carrier or the like may be added.

The emulsion composition of the present invention can be used for various applications depending on, for example, the type of oily component. For example, when the oily component is a flavoring, the emulsion composition can be applied as an emulsified flavoring preparation. When the oily component is a colorant, the emulsion composition can be applied as an emulsified colorant preparation. When the oily component is a nutritional component (e.g., an oil-soluble vitamin or an oil-soluble amino acid), the emulsion composition can be applied as an emulsified nutrition fortifier preparation (a food additive used for the supplementation and enhancement of nutritional components)(e.g., an emulsified vitamin preparation or an emulsified amino acid preparation). When the oily component is a functional material, the emulsion composition can be applied as an emulsified functional material preparation. Moreover, the emulsion composition of the present invention can be applied as a clouding agent (also known as a turbidity agent or a cloudifier) for imparting appropriate cloudiness to aqueous media, such as drinks.

The particle diameter of emulsified particles of the emulsion composition of the present invention is not particularly limited and can be suitably adjusted depending on the intended use.

In one embodiment of the present invention, the emulsified particle diameter of the emulsion composition may be 3 μm or less, preferably 2.5 μm or less, more preferably 2 μm or less, and even more preferably 1.5 μm or less, in terms of median diameter (on a volume basis). Such an emulsion composition can be suitably used for, for example, drinks, desserts, frozen desserts, confectioneries (e.g., gum, chocolates, candies, cookies, and biscuits), bread, soups, seasonings, jams, fruit liquors, processed fruits, processed farm products, processed meats, processed fishery products, dairy products, milled products, noodles, liquid food, health food, or supplements.

In one preferable embodiment of the present invention, the emulsified particle diameter of the emulsion composition is 1.2 μm or less, preferably 1.1 μm or less, more preferably 1 μm or less, and even more preferably 0.9 μm or less, in terms of median diameter (on a volume basis). Such an emulsion composition can be suitably used for, for example, drinks.

The lower limit of the median diameter (on a volume basis) is not particularly limited and is, for example, 0.1 μm or more, preferably 0.2 μm or more, and more preferably 0.3 μm or more.

Aqueous Composition

The present invention also relates to an aqueous composition containing the emulsion composition described above.

The type of aqueous composition is not particularly limited and may be, for example, a food or drink, a cosmetic or fragrance, a pharmaceutical, or a quasi-drug. The type of aqueous composition is preferably a food or drink, and more preferably a drink.

The amount of the emulsion composition of the present invention in the aqueous composition may vary depending on the type, use, etc. of the composition and may be, for example, in the range of 0.001 to 5 mass % or 0.01 to 1 mass %.

Food and Drink

The present invention also relates to a food or drink containing the emulsion composition described above.

The type of food or drink is not particularly limited. Specific examples include drinks such as milk drinks, *lactobacillus* drinks, carbonated drinks, fruit-containing drinks (e.g., fruit-juice-containing drinks, fruit-juice-containing soft drinks, fruit-juice-containing carbonated drinks, and fruit-pulp-containing drinks), vegetable-containing drinks, vegetable- and fruit-containing drinks, alcoholic drinks such as liqueur, coffee drinks, powdered drinks, sport drinks, and supplement drinks; tea drinks, such as black tea drinks, green tea drinks, and blended tea drinks (various drinks and tea drinks are included in "drinks"); puddings, such as custard pudding, milk pudding, or fruit-juice-containing pudding; desserts such as jellies, bavarois, or yogurt; frozen desserts, such as milk ice cream, fruit-juice-containing ice cream, soft-serve ice cream, and popsicles; confectioneries, such as gum (e.g., stick gum and sugar-coated gum granules), chocolates (e.g., flavored chocolates and coated chocolates), candies (e.g., hard candies, soft candies, sugar-coated candies, and taffy), cookies, biscuits, and doughnuts; bread; soups such as consommé soup and potage soup; liquid seasonings such as vinaigrette dressings, non-oil dressings, ketchup, gravy, and sauce; jams, such as strawberry jam, blueberry jam, marmalade, apple jam, apricot jam, preserves, and syrups; fruit liquors such as red wine; processed fruits such as candied cherries, apricots, apples, strawberries, and peaches; processed farm products such as pickles; processed meats, such as ham and sausage; processed fishery products, such as fish meat sausage, hanpen (cakes of pounded fish), chikuwa (tubular fish cakes), and boiled fish paste; dairy products; milled products (e.g., okonomiyaki (Japanese pancake) mix and takoyaki (octopus balls) mix); noodles; liquid food; health food; and supplements.

Among these, drinks, desserts (particularly preferably jellies), candies, jams, pickles, and liquid seasonings are preferable, and drinks are more preferable.

Method for Improving Emulsion Stability of Emulsion Composition (Emulsion Stability Improvement Method)

The present invention also relates to the following method for improving the emulsion stability of an emulsion composition:

A method for improving the emulsion stability of an emulsion composition containing water, an oily component, and gum arabic having a molecular weight of not less than 1 million, the method comprising incorporating a salt into the composition, the salt content being 90 parts by mass or less per 100 parts by mass of the gum arabic.

This method may be the same as or similar to the embodiments of the emulsion composition of the present invention and the preparation method described above, and can be understood by referring to the method for preparing the emulsion composition according to the present invention described above.

Specifically, the step of incorporating a salt into the emulsion composition can be performed, for example, by a method comprising mixing an oily component and an aqueous phase containing water, gum arabic having a molecular weight of not less than 1 million, and the predetermined amount of salt, as in the method for preparing the emulsion composition described above.

The means or method, and the conditions for mixing, are not particularly limited as long as water, an oily component, gum arabic having a molecular weight of not less than 1 million, and the predetermined amount of salt are mixed. Mixing itself may be an emulsification treatment, or mixing may be accompanied by an emulsification treatment.

Mixing the components of the emulsion composition and an emulsification treatment may be performed in any order. For example, as the operation of the method for improving the emulsion stability of the emulsion composition, the following methods can be used:

(1) a method comprising:
mixing all of and/or the total amount of the components of the emulsion composition; and then performing an emulsification treatment;

(2) a method comprising:
mixing part of and/or a partial amount of the components of the emulsion composition;
performing an emulsification treatment;
adding the remainder of the components of the emulsion composition; and
then further performing an emulsification treatment;

(3) a method comprising mixing all of and/or the total amount of the components of the emulsion composition by an emulsification treatment; or (4) a method comprising:
mixing part of and/or a partial amount of the components of the emulsion composition by an emulsification treatment;
adding the remainder of and/or the remaining amount of the components of the emulsion composition; and then further mixing the components by an emulsification treatment.

The method for improving the emulsion stability of the emulsion composition according to the present invention includes an embodiment in which the step of incorporating a salt is performed before partial or complete formation of emulsified particles.

The method for improving the emulsion stability of an emulsion composition according to the present invention includes the following preferable embodiment:

A method for improving the emulsion stability of an emulsion composition containing gum arabic, the method comprising:

1) preparing a mixture containing water, an oily component, gum arabic, and a salt; and 2) subjecting the mixture to an emulsification treatment to prepare an emulsion composition.

Specific examples of the preferable embodiment include the following examples:

A) in steps 1 and 2, a salt is added to a mixed composition containing water, an oily component, and gum arabic, and an emulsification treatment is performed to preparing an emulsion composition;

B) in steps 1 and 2, gum arabic is added to a mixed composition containing water, an oily component, and a salt, and an emulsification treatment is performed to prepare an emulsion composition;

C) in steps 1 and 2, an oily component is added to a mixed composition containing water, gum arabic, and a salt, and an emulsification treatment is performed to prepare an emulsion composition; and D) in steps 1 and 2, water is added to a mixed composition containing an oily component, gum arabic, and a salt, and an emulsification treatment is performed to prepare an emulsion composition.

Although this is stated just to be sure, in these examples (in particular, example A and example B), each mixed composition described above may be subjected to the emulsification treatment. In this case, after addition of a further component, a further emulsification treatment may be performed, or a mere mixing treatment may be performed.

These embodiments and examples may overlap with each other.

Embodiment B

Embodiment B of the present invention is described below.

[1] Emulsion Composition

The emulsion composition of the present invention is an emulsion composition comprising:
water;
an oily component;
unmodified or modified gum arabic; and
0.01 mass % or more and less than 10 mass % of a salt,
with the proviso that an emulsion composition containing carnauba wax is excluded.

The emulsion composition of the present invention may be suitably an oil-in-water emulsion composition.

More descriptively, the emulsion composition of the present invention may suitably contain an aqueous phase that is a continuous phase containing water as a medium, and an oil phase, in a particle form, containing an oil-soluble physiologically active substance and/or an oil-based solvent (which may be referred to as "oil-containing particles" in the present specification).

1: Water

Examples of water used in the present invention include pure water, ion-exchanged water, and tap water.

2: Oily Component

The oily component (i.e., a component that forms an oil phase) used in the present invention comprises at least one member selected from the group consisting of oil-soluble materials (including liposoluble materials) and oil-based solvents.

2-1: Oil-Soluble Material

Examples of oil-soluble materials usable in the present invention include oil-soluble flavorings, oil-soluble colorants, oil-soluble physiologically active substances, and the like.

2-1-1: Oil-Soluble Flavoring

The oil-soluble flavoring (including liposoluble flavorings) usable in the present invention is not limited as long as the oil-soluble flavoring is an oil-soluble or liposoluble substance containing an aroma component.

The oil-soluble flavoring usable in the present invention is preferably an edible flavoring that can be added to food or drink, or a flavoring that is applicable to a human body as a cosmetic or fragrance.

Examples of oil-soluble flavorings include extracts obtained by, for example, extraction with a non-volatile solvent, extraction with a volatile solvent, supercritical extraction, or a combination thereof, from a natural ingredient derived from an animal or plant; natural flavorings, such as essential oils and recovery essences, obtained by a technique such as steam distillation or a press method; synthetic flavorings synthesized by a chemical technique; and flavoring bases obtained by adding and/or dissolving these flavorings in a fat, an oil, and/or a solvent.

Examples of natural flavorings include extracts, such as absolutes, essences, and oleoresins; squeezed liquid obtained by cold pressing or the like; alcohol extracts or extracts obtained using a mixture of water and an alcohol ("tinctures" as such extracts); and the like.

Specific examples of the flavorings include citrus essential oils, such as orange oil, lemon oil, grapefruit oil, lime oil, and mandarin oil; flower oils (or absolutes), such as lavender oil; essential oils, such as peppermint oil, spearmint oil, and cinnamon oil; essential oils (or oleoresins) of spice, such as allspice, anise seed, basil, laurel, cardamom, celery, clove, garlic, ginger, mustard, onion, paprika, parsley, and black pepper; synthetic flavorings, such as limonene, linalool, geraniol, menthol, eugenol, and vanillin; extract oils derived from beans, such as coffee, cacao, vanilla, and roasted peanuts; essence derived from tea, such as black tea, green tea, and oolong tea; and synthetic flavoring compounds.

These flavorings can be used individually, but are typically used as a blended flavoring prepared by combining any two or more flavorings.

The term "flavoring" as used herein is defined as including not only flavorings composed of a single compound but also blended flavorings described above.

2-1-2: Oil-Soluble Colorant

The oil-soluble colorant (including liposoluble colorants) usable in the present invention is not limited as long as the oil-soluble colorant is an oil-soluble or liposoluble substance containing a coloring component.

The oil-soluble colorant usable in the present invention is preferably an edible colorant that can be added to food or drink, or a colorant that is applicable to a human body as a cosmetic or fragrance.

Examples of oil-soluble colorants include paprika pigment, red pepper pigment, turmeric pigment, annatto pigment, tomato pigment, marigold pigment, *Haematococcus* algae pigment, *Dunaliella* carotene, carrot carotene, palm oil carotene, β-carotene, astaxanthin, canthaxanthin, cryptoxanthin, curcumin, lycopene, lutein, apocarotenal, fucoxanthin, cryptoxanthin, zeaxanthin, capsanthin, capsorubin, norbixin, bixin, chlorophyll, and the like.

These oil-soluble colorants may be used singly or in a combination of two or more.

2-1-3: Oil-Soluble Physiologically Active Substance

The oil-soluble physiologically active substance (including liposoluble physiologically active substances) usable in the present invention is not limited as long as the oil-soluble physiologically active substance is an oil-soluble or liposoluble substance that is useful in a living organism.

As will be understood from the above description, an emulsion composition containing the oil-soluble physiologically active substance can be used as, for example, a medicinal agent, a nutrition fortifier (e.g., a vitamin preparation or an amino acid preparation), or a functional material preparation.

The oil-soluble physiologically active substance usable in the present invention is preferably an edible substance that can be added to food or drink, or a substance that is applicable to a human body as a cosmetic or fragrance.

Examples of oil-soluble physiologically active substances include oil-soluble medicinal agents; liposoluble vitamins, such as liver oil, vitamin A (e.g., retinol), vitamin A oil, vitamin D (e.g., ergocalciferol and cholecalciferol), vitamin B2 butyric acid ester, ascorbic acid fatty acid ester, vitamin E (e.g., tocopherol, tocotrienol, and tocopherol acetate), and vitamin K (e.g., phylloquinone and menaquinone); plants essential oils, such as limonene, linalool, nerol, citronellol, geraniol, citral, 1-menthol, eugenol, cinnamic aldehyde, anethole, perillaldehyde, vanillin, and γ-undeca lactone; resveratrol, oil-soluble polyphenol, glucosylceramide, sesamin, phosphatidylserine, coenzyme $Q_{10}$, curcumin, astaxanthin, lutein, and α-lipoic acid; Ω-3 fatty acids, such as α-linolenic acid, eicosapentaenoic acid, and docosahexaenoic acid; Ω-6 fatty acids, such as linoleic acid and γ-linolenic acid; functional materials, such as plant sterols; and the like.

Preferable examples include liposoluble vitamins, coenzyme $Q_{10}$, α-lipoic acid, and Ω-3 fatty acids, such as a-linolenic acid, eicosapentaenoic acid, and docosahexaenoic acid.

These oil-soluble physiologically active substances may be used singly or in a combination of two or more.

2-2: Oil-Based Solvent

The oil-based solvent usable in the present invention may be a solvent that is suitably usable as a solvent for the oil-soluble material, specifically a solvent that is compatible with the oil-soluble material.

The oil-based solvent usable in the present invention is preferably an edible substance that can be added to food or drink, or a substance that is applicable to a human body as a cosmetic or fragrance.

Examples of oil-based solvents usable in the present invention include vegetable oils and fats, such as rapeseed oil, corn oil, palm oil, soybean oil, olive oil, jojoba oil, coconut oil, elemi resin, and mastic resin; animal oils and fats, such as beef tallow and lard; sucrose acetate isobutyrate (SAIB); rosin; dammar resin; ester gum; glycerin fatty acid esters; medium-chain triglycerides (MCTs) (medium-chain fatty acid oils); and the like.

These solvents may be used singly or in a combination of two or more.

The oil-based solvent usable in the present invention is preferably at least one member selected from the group consisting of glycerin fatty acid esters, triglycerides, sucrose acetate isobutyrate, and vegetable oils and fats, and more preferably at least one member selected from the group consisting of glycerin fatty acid esters and triglycerides (more preferably medium-chain triglycerides).

Medium-chain triglycerides (MCTs) refer to triacylglycerols composed of medium-chain fatty acids having about 6 to 12 carbon atoms, preferably 6 to 10 carbon atoms, and more preferably 8 to 10 carbon atoms. Commercially available medium-chain triglycerides (MCTs) can be used without any restriction.

Specific examples of medium-chain triglycerides (MCTs) include caprylic triglyceride, capric triglyceride, caprylic and capric triglyceride, and mixtures of these triglycerides.

The emulsion composition of the present invention is free of carnauba wax as an oily component. The emulsion composition of the present invention may be substantially or completely free of carnauba wax. The embodiment in which the emulsion composition is substantially free of carnauba wax can includes an embodiment in which the emulsion composition contains carnauba wax in an amount that is not sufficient for carnauba wax to function as wax. Specifically, the amount may be, for example, less than 5 mass %, 4 mass % or less, 3 mass % or less, 2 mass % or less, or 1 mass % or less.

A preferable embodiment of the present invention may be an embodiment in which the emulsion composition is substantially free of wax.

The oily component content in the emulsion composition of the present invention is not particularly limited and may be, for example, 0.1 mass % or more, preferably 0.5 mass % or more, more preferably 1 mass % or more, and even more preferably 2 mass % or more. The upper limit of the oily component content is also not particularly limited. The oily component content may be, for example, 50 mass % or less, preferably 45 mass % or less, more preferably 40 mass % or less, and even more preferably 35 mass % or less.

The oily component content in the emulsion composition of the present invention is preferably in the range of 0.1 to 300 parts by mass, more preferably 2 to 200 parts by mass, even more preferably 3 to 150 parts by mass, and still even more preferably 4 to 120 parts by mass, per 100 parts by mass of the water.

3: Gum Arabic

Gum arabic is a polysaccharide derived from sap (secretion) of the genus *Acacia* of the Leguminosae family (in particular, *Acacia senegal* and *Acacia seyal*). The molecular weight of gum arabic obtained by drying the sap is generally less than 1000000 (1.0 million) ($1.0 \times 10^6$) (more specifically, generally, about 200000 (0.2 million) to 600000 (0.6 million)). Gum arabic having the above molecular weight is commonly distributed in the market.

Gum arabic generally contain arabinogalactan protein (AGP), arabinogalactan (AG), and glycoprotein (GP) as three major components.

On the other hand, in addition to the gum arabic commonly distributed in the market, gum arabic having a molecular weight of 1000000 (1.0 million) or more can be used as gum arabic in the present invention.

In the present invention, gum arabic having a molecular weight of 1000000 (1.0 million) or more can be suitably used.

The gum arabic used in the present invention includes modified gum arabic and unmodified gum arabic.

The term "modified gum arabic" as used herein means chemically modified gum arabic, in other words, gum arabic having a substituent that natural gum arabic does not have. The term "unmodified gum arabic," which is excluded from this, means chemically unmodified gum arabic, in other words, gum arabic having no substituent that natural gum arabic does not have.

Examples of the modified gum arabic include octenylsuccinic acid-modified gum arabic.

The term "unmodified gum arabic" as used herein may be any gum arabic that is not substantially chemically modified, and includes gum arabic that is reformed without chemical modification.

The term "unmodified gum arabic" as used herein may include gum arabic that is not substantially chemically modified.

The term "gum arabic that is not substantially chemically modified" means gum arabic that has a small number of substituents that natural gum arabic does not have for some reason (e.g., unintentional contact with a chemical substance), but does not have changed properties due to this compared with gum arabic having no substituent that natural gum arabic does not have in light of the gist of the present invention (i.e., gum arabic having the same properties as gum arabic that does not have changed properties compared with gum arabic having no substituent that natural gum arabic does not have in light of the gist of the present invention).

In the present invention, it is desirable to exclude octenylsuccinic acid-modified gum arabic as gum arabic. Specifically, the gum arabic used in the present invention is preferably gum arabic (excluding octenylsuccinic acid-modified gum arabic).

In the present invention, unmodified gum arabic is preferably used.

The molecular weight of gum arabic in the present invention means a weight average molecular weight.

The weight average molecular weight can be determined by using gel filtration chromatography in which three detectors, i.e., a light scattering (MALLS) detector, a refraction index (RI) detector, and an ultraviolet (UV) detector, are connected online.

In the present specification, a technique of such gel filtration chromatography is referred to as "GPC-MALLS."

As commonly understood by a person skilled in the art, GPC-MALLS operates in such a manner that
(1) the molecular weight is measured by a MALLS detector,
(2) the mass (composition ratio) of each component is measured by an RI detector, and
(3) the protein content is measured by a UV detector.
Therefore, it is possible to obtain the molecular weight of gum arabic and the compositions of its constituents without reference to the standard gum arabic having a known molecular weight.

Detailed principals and characteristics of the GPC-MALLS are known and can be found in, for example, the following Non-Patent Document: Idris, O. H. M., Williams, P. A. Phillips, G. O.; Food Hydrocolloids, 12, (1998) pp. 375-388.

Measurement conditions for GPC-MALLS used in the present invention are as below:
Column: Superose (6HR) 10/30 (Pharmacia Biotech, Sweden)
Flow rate: 0.5 mL/min
Eluant: 0.2 M NaCl
Preparation of a sample: A sample to be analyzed is diluted with the eluant (0.2 M NaCl).
Sample concentration: 0.4% (W/V)
Injection volume of sample solution: 100 μL
dn/dc: 0.141
Temperature: Room temperature
Detector: 1) MALLS (multi-angle laser light scattering) detector: DAWN EOS (Wyatt Technology Inc., USA)
2) RI detector
3) UV detector (absorption at 214 nm)

By processing the data obtained by the GPC-MALLS conducted under the above conditions using, for example, ASTRA Version 4.5 (Wyatt Technology) software, each parameter of the components of the gum arabic, such as the weight average molecular weight, recovery rate (% mass), polydispersity value (P) and root mean square radius of gyration (Rg), can be obtained. When the data is processed for all peaks on the chromatogram obtained using an RI detector as one peak, the obtained molecular weight is identified as the weight average molecular weight ($M_{wt}$) (more specifically, $M_{wt}$ processed as one peak). When the point where the RI chart begins to rise from the baseline of the chromatogram is defined as the starting point, and the point where the RI chart falls and intersects the baseline is defined as the ending point, the "one peak" on the chromatogram means the region from the starting point to the ending point.

The molecular weight of gum arabic used in the present invention is not less than 1 million, preferably more than 1 million, more preferably not less than 1.1 million, even more preferably not less than 1.2 million, and still even more preferably not less than 1.3 million.

The upper limit of the molecular weight of gum arabic is not particularly limited as long as the gum arabic is soluble in water; however, the molecular weight of gum arabic may be, for example, not greater than 5 million, preferably not greater than 4.5 million, and more preferably not greater than 4 million.

The gum arabic usable in the present invention preferably has the above molecular weight and is water-soluble.

"Water-soluble" herein means the property that a sample is completely or substantially completely dissolved in a large excess of water.

"Water" herein means any type of water, e.g., pure water, ion-exchanged water, or ion-containing water. The water temperature may be any suitable temperature as long as the gum arabic is soluble.

More specifically, by appropriately setting the type or the temperature of water, any gum arabic dissolvable in water may suitably be used in the present invention.

The gum arabic used in the present invention is preferably gum arabic that has the above molecular weight and is completely or substantially dissolved in water in an amount that is three or more times the mass of the gum arabic at room temperature (here, specifically 25° C.).

The gum arabic can be prepared by subjecting gum arabic commonly distributed in the market as a raw material to a heat treatment at 60° C. or more or a drying treatment at 60° C. or more (which hereinafter may be referred to as "reforming treatment" in the present specification) until the predetermined molecular weight is achieved.

The gum arabic can be prepared by a known method disclosed in, for example, JP2000-166489A, WO2003/093324, or WO2005/026213.

The reforming treatment may be suitably a heat treatment using a thermostat or a heater, such as an oven.

The temperature and the time in the heat treatment are not particularly limited. The heating temperature may be, for example, 110 to 130° C., and the heating time may be, for example, 10 hours or more, preferably 15 hours or more, 24 hours or more, or 48 hours or more.

The upper limit of the heating time can vary depending on the desired molecular weight of gum arabic and is, for example, about 72 hours when heated at 110° C.

As long as it is possible to prepare gum arabic having the molecular weight specified in the present invention, the heating method is not limited to one with the above conditions; the heating temperature, the heating time, the heating means, and the heating environment conditions (e.g., relative humidity, presence or absence of a closed system) can be optionally selected.

For example, the effects of the present invention achieved by the heat treatment conducted under the conditions described above can also be obtained by, for example, the following methods:
(1) a method in which heating is performed at a temperature lower than 110° C. for more than 10 hours; or
(2) a method in which heating is performed at a temperature higher than 110° C. for a short time.

Specifically, one example of the former case may be a method in which heating is performed at 80° C. for 3 days to 1 week or longer, or the like. The same effects can be achieved in less time by using microwave radiation instead of a heating means using an oven. In addition, a heat treatment in the absence of oxygen, such as under a nitrogen substitution condition, is a desirable treatment method.

When the gum arabic used in the present invention is gum arabic belonging to *Acacia senegal*, the arabinogalactan protein content is 16 mass % or more, preferably 17 mass % or more, and more preferably 20 mass % or more. The upper limit of the arabinogalactan protein content is not particularly limited as long as the gum arabic is soluble in water. It is desirable that the arabinogalactan protein content be about 30 mass % or less.

Gum arabic (*Acacia senegal*) commonly distributed as general gum arabic in the market, which has a molecular weight of less than 1 million, generally contains 5 to 15 mass % of AGP.

The proportion of AGP in gum arabic may be determined by the GPC-MALLS described above.

More specifically, when the RI chart of a chromatogram obtained by using an RI detector is divided into two parts, i.e., Peak 1 (high molecular weight elution fraction), which traces the first eluted portion, and Peak 2 (low molecular weight elution fraction), which traces the later eluted portion, and the data are then processed with ASTRA Version 4.5 (Wyatt Technology) software, the obtained recovery ratio of Peak 1 (% mass) corresponds to the AGP content (mass %) of the gum arabic subjected to GPC-MALLS.

This is explained in detail with reference to a chromatogram (FIG. 1) showing the results of analysis in which unreformed gum arabic (*Acacia senegal*) was analyzed using GPC-MALLS. The point where the RI chart begins to rise from the baseline of the RI chart is defined as the starting point and the point where the RI chart falls and intersects the baseline is defined as the ending point. Between the starting point and the ending point, the point where the RI value becomes minimum is defined as the boundary, with the region between the starting point and the boundary being defined as Peak 1 and the region between the boundary and the ending point being defined as Peak 2.

The gum arabic used in the present invention may be desalted gum arabic.

The desalted gum arabic is obtained by subjecting gum arabic to a desalting treatment (e.g., a treatment using an electrodialysis membrane or an ion-exchange resin treatment).

As can be understood from this, the desalted gum arabic may be gum arabic in which some or all of the metal atoms or ions thereof are removed.

The desalted gum arabic is commercially available. Examples of commercially available products of the desalted gum arabic include those sold under the trade names such as San Arabic (product name; Sanei-yakuhin Co., Ltd.) and EFISTAB AA (product name; Nexira). Such commercially available products may be used.

The desalted gum arabic may be gum arabic having a metal content of preferably 0 to 100 ppm, and more preferably 0 to 50 ppm.

The desalted gum arabic may be gum arabic prepared by mixing nondesalted gum arabic and desalted gum arabic so that the metal content is in such a range as described above.

A preferable embodiment of the gum arabic used in the present invention includes gum arabic in which the viscosity of an aqueous gum arabic solution (Brix: 25°) measured according to the following conditions is 90 mPa·s or more.

The upper limit of the viscosity of the aqueous gum arabic solution (Brix: 25°) is not particularly limited and may be, for example, 300 mPa·s.

Conditions for Measuring Viscosity
1) 28 g of gum arabic is added to 70 g of ion-exchanged water (20° C.), and the mixture is stirred to prepare an aqueous gum arabic solution.
2) The aqueous gum arabic solution is allowed to stand (at 5° C. for 18 hours), and the generated bubbles are removed.
3) Ion-exchanged water is appropriately added so that the Brix of the aqueous gum arabic solution is 25°, thereby preparing a 25° Brix aqueous gum arabic solution. This aqueous solution is used as a sample.
4) The viscosity of the sample is measured under the following conditions using a B-type viscometer (type BM; TOKIMEC INC.).
Conditions
Rotor: No. 2
Rotation rate: 30 rpm
Rotation time: 1 minute A preferable embodiment of the gum arabic used in the present invention include gum arabic whose b value in the Lab color system measured according to the following conditions is 10 or more, and preferably 12 or more.

The upper limit of the b value is not particularly limited and may be, for example, 30, and preferably 24.
Method for Measuring b Value
1) 28 g of gum arabic is added to 70 g of ion-exchanged water (20° C.), and the mixture is stirred to prepare an aqueous gum arabic solution.
2) The aqueous gum arabic solution is allowed to stand (at 5° C. for 18 hours), and the generated bubbles are removed.
3) Ion-exchanged water is appropriately added so that the Brix of the aqueous gum arabic solution is 10°, thereby preparing a 10° Brix aqueous gum arabic solution. The aqueous solution is used as a sample.
4) The b value of the sample is measured using a spectrophotometer.
Apparatuses etc. used in method for measuring b value
Measurement for Brix: digital sugar content (concentration) measurement apparatus (PR-101α; Atago Co., Ltd.)
Measurement for b value: ultraviolet-visible spectrophotometer (V-760DS; JASCO Corporation) Measurement conditions: quartz cell (10 mm×10 mm); transmittance (% T)

The gum arabic content in the emulsion composition of the present invention is not particularly limited and may be, for example, in the range of 3 to 40 mass %, preferably 4 to 35 mass %, more preferably 5 to 35 mass %, even more preferably 6 to 30 mass %, still even more preferably 8 to 30 mass %, particularly preferably 10 to 25 mass %, and more particularly preferably 12 to 25 mass %.

It is desirable that the gum arabic content be preferably 10 parts by mass or more, more preferably 30 parts by mass or more, even more preferably 40 parts by mass or more, still even more preferably 50 parts by mass or more, particularly preferably 80 parts by mass or more, more particularly preferably 100 parts by mass or more, even more particularly preferably 120 parts by mass or more, and most preferably 150 parts by mass or more, per 100 parts by mass of the total amount of the oily component in the emulsion composition. The upper limit of the gum arabic content per 100 parts by mass of the total amount of the oily component in the emulsion composition is not particularly limited. The gum arabic content may be, for example, 35000 parts by mass or less, preferably 10000 parts by mass or less, more preferably 5000 parts by mass or less, even more preferably 1000 parts by mass or less, still even more preferably 600 parts by mass or less, and particularly preferably 500 parts by mass or less.

4: Salt

In the present invention, use of the gum arabic described above and 0.01 mass % or more and less than 10 mass % of a salt in combination enables an emulsion composition having high emulsion stability to be provided.

The salt used in the present invention is not limited as long as it is a water-soluble salt. Inorganic salts and/or organic acid salts are usable. In the present invention, it is preferable to use an edible inorganic salt and/or organic acid salt.

Moreover, it is preferable to use an inorganic salt in the present invention.

Examples of inorganic salts include sodium salts (e.g., sodium chloride), potassium salts (e.g., potassium chloride), calcium salts (e.g., calcium lactate and calcium chloride), magnesium salts (e.g., magnesium chloride), and the like.

Preferable examples of inorganic salts include sodium chloride, potassium chloride, calcium lactate, calcium chloride, and magnesium chloride.

More preferable examples of inorganic salts include sodium chloride, potassium chloride, and magnesium chloride.

Even more preferable examples of inorganic salts include sodium chloride.

These salts may be used singly or in a combination of two or more.

In the present invention, organic acid salts are also usable.

Examples of organic acid salts include sodium salts (e.g., sodium citrate and sodium phosphate), potassium salts (e.g., potassium citrate and potassium phosphate), magnesium salts (e.g., magnesium carbonate), and the like.

Preferable examples of organic acid salts include sodium citrate, sodium phosphate, and potassium phosphate.

The emulsion composition of the present invention contains a salt, and the salt content in the emulsion composition is 0.01 mass % or more and less than 10 mass %.

The lower limit of the salt content in the emulsion composition of the present invention may be 0.01 mass % or more, preferably 0.05 mass % or more, more preferably 0.1 mass % or more, even more preferably 0.5 mass % or more, still even more preferably 1 mass % or more, and particularly preferably 2 mass % or more.

The upper limit of the salt content in the emulsion composition may be preferably 9 mass % or less, more preferably 8 mass % or less, and even more preferably 7 mass % or less.

The salt content in the emulsion composition of the present invention may be, for example, 0.05 parts by mass or more, preferably 0.1 parts by mass or more, more preferably 0.5 parts by mass or more, even more preferably 1 part by mass or more, still even more preferably 2 parts by mass or more, further still even more preferably 3 parts by mass or more, more particularly preferably 5 parts by mass or more, and most preferably 10 parts by mass or more, per 100 parts by mass of the gum arabic.

The salt content in the emulsion composition of the present invention may be, for example, 90 parts by mass or less, preferably 80 parts by mass or less, more preferably 70 parts by mass or less, and even more preferably 60 parts by mass or less, per 100 parts by mass of the gum arabic.

When desalted gum arabic is used as the gum arabic, the amount of organic acid salt in the emulsion composition may suitably exceed 1 part by mass.

When desalted gum arabic is used, it may be suitably used in combination with an inorganic salt.

5: Polyhydric Alcohol

The emulsion composition of the present invention may contain a polyhydric alcohol.

Use of a polyhydric alcohol improves the storage stability of an emulsion composition and enables an emulsion composition having a high antiseptic effect to be provided.

Examples of polyhydric alcohols usable in the present invention include glycerin, diglycerin, triglycerin, polyglycerin, propylene glycol, dipropylene glycol, 1,3-butylene glycol, ethylene glycol, polyethylene glycol, sorbitol (D-sorbitol), xylitol, maltitol, erythritol, mannitol, xylose, glucose, lactose, mannose, oligotose, high-fructose corn syrup, sucrose, and the like.

These polyhydric alcohols may be used singly or in a combination of two or more.

The polyhydric alcohol in the present invention is preferably propylene glycol, glycerin, or a combination thereof.

When propylene glycol is used as a polyhydric alcohol, the lower limit of the propylene glycol content in the emulsion composition of the present invention may be, for example, 3 mass %, 5 mass %, 10 mass %, 15 mass %, 20 mass %, 30 mass %, 35 mass %, 40 mass %, 45 mass %, or 50 mass %.

When propylene glycol is used as a polyhydric alcohol, the upper limit of the propylene glycol content in the emulsion composition of the present invention may be, for example, 65 mass %, 60 mass %, 55 mass %, 50 mass %, 45 mass %, 40 mass %, or 35 mass %.

The polyhydric alcohol content in the emulsion composition of the present invention is not particularly limited and may be, for example, in the range of 3 to 80 mass %, preferably 5 to 60 mass %, more preferably 6 to 50 mass %, and even more preferably 8 to 45 mass %.

When propylene glycol is used as a polyhydric alcohol, the propylene glycol content in the emulsion composition of the present invention may be, for example, in the range of 3 to 40 mass %, preferably 5 to 30 mass %, more preferably 8 to 25 mass %, and even more preferably 10 to 20 mass %.

When glycerin is used as a polyhydric alcohol, the lower limit of the glycerin content in the emulsion composition of the present invention may be, for example, 5 mass %, 10 mass %, 15 mass %, 20 mass %, 30 mass %, 35 mass %, 40 mass %, 45 mass %, or 50 mass %.

When glycerin is used as a polyhydric alcohol, the upper limit of the glycerin content in the emulsion composition of the present invention may be, for example, 80 mass %, 70 mass %, 60 mass %, 55 mass %, 50 mass %, or 45 mass %.

When glycerin is used as a polyhydric alcohol, the glycerin content in the emulsion composition of the present invention may be, for example, in the range of 5 to 80 mass %, preferably 10 to 70 mass %, more preferably 15 to 60 mass %, even more preferably 20 to 50 mass %, and still even more preferably 25 to 45 mass %.

As described above, incorporating a polyhydric alcohol into an emulsion composition has advantages in that the storage stability of the emulsion composition can be improved and an emulsion composition having a high antiseptic effect can be provided.

However, use of a polyhydric alcohol can disadvantageously cause a decrease in the emulsion stability of an emulsion composition.

To address this problem, by incorporating gum arabic and 0.01 mass % or more and less than 10 mass % of a salt, an emulsion composition having high emulsion stability, even though it contains a polyhydric alcohol, can be provided in the present invention.

Synthetic preservatives, such as sodium benzoate and potassium sorbate, are generally used in conventional emulsion compositions from the viewpoint of an antiseptic effect.

However, such synthetic preservatives have, for example, the following problems:

(1) use of such a synthetic preservative may adversely affect the flavor of an emulsion composition; and (2) although these preservatives are effective against certain bacteria and fungi, there are bacteria and fungi that the preservatives are not effective against.

Further, due to recent health consciousness of consumers, use of synthetic preservatives tends to be avoided.

From this viewpoint, it is desirable that the emulsion composition of the present invention be substantially free of synthetic preservatives.

In regard to these points, the present invention can provide an emulsion composition having excellent antiseptic properties and emulsion stability even if use of a synthetic preservative is substantially suppressed or no synthetic preservative is used.

6: pH

The emulsion composition of the present invention generally has a pH in the range of 2 to 7, preferably 2 to 6, more preferably 2 to 4.5, even more preferably 2 to 4, particularly preferably 2.2 to 3.8, and further more preferably 2.5 to 3.5.

When the pH is in this range, an emulsion composition having more improved emulsion stability and high antiseptic properties can be provided.

To adjust the pH of the emulsion composition to the above range, an organic acid and/or an inorganic acid may be used as necessary. The type of organic acid and/or inorganic acid is not particularly limited.

Examples of organic acids and/or inorganic acids include citric acid, phytic acid, ascorbic acid, phosphoric acid, lactic acid, adipic acid, gluconic acid, succinic acid, acetic acid, tartaric acid, fumaric acid, malic acid, pyrophosphoric acid, and the like. These organic acids and/or inorganic acids may be used singly or in a combination of two or more.

The organic acid and/or inorganic acid in the present invention is preferably at least one member selected from the group consisting of citric acid, phytic acid, ascorbic acid, phosphoric acid, and lactic acid.

The emulsion composition of the present invention may contain as one or more other optional components a water-soluble vitamin, a thickening stabilizer, an antioxidant, a chelating agent, an oxidation inhibitor, or the like as long as the effects of the present invention are not impaired.

The emulsion composition of the present invention may contain ethanol as long as the effects of the present invention are not impaired.

7: Emulsion Stability

The emulsion composition of the present invention has the advantage of excellent emulsion stability.

The term "emulsion stability" as used herein includes emulsifiability (ease of forming emulsified particles), emulsion storage stability (stability of emulsified particles during storage), and emulsion physical stability (stability of emulsified particles against external physical force).

Specifically, the emulsion composition of the present invention can exhibit high stability when it is evaluated based on the criteria described later in the Examples.

[2] Method for Preparing Emulsion Composition

The emulsion composition according to the present invention can be prepared by mixing an oily component and an aqueous phase containing water, gum arabic, and the predetermined amount of salt.

The means or method, and the conditions for mixing are not particularly limited as long as water, an oily component, gum arabic, and the predetermined amount of salt are mixed. Mixing itself may be an emulsification treatment, or mixing may be accompanied by an emulsification treatment.

The emulsification treatment may be performed with an emulsifying machine, such as a homogenizer (e.g., a high-pressure homogenizer, a homogenizing disperser, a homo-mixer, a Polytron stirrer, a colloid mill, and a Nanomizer). The conditions for the emulsification treatment can be suitably determined, depending on the type of emulsifying machine used.

For the emulsion composition of the present invention, it is desirable that an emulsification treatment be performed after mixing water, an oily component, gum arabic, and 0.01 mass % or more and less than 10 mass % of a salt.

The method for preparing the emulsion composition according to the present invention includes the following preferable embodiment:

A method for preparing an emulsion composition containing water, an oily component, gum arabic (unmodified gum arabic or modified gum arabic), and 0.01 mass % or more and less than 10 mass % of a salt (with the proviso that an emulsion composition containing carnauba wax is excluded), the method comprising:

preparing a mixture containing the water, the oily component, the gum arabic, and the salt; and subjecting the mixture to an emulsification treatment.

The method for preparing the emulsion composition according to the present invention also includes the following preferable embodiment:

A method for preparing an emulsion composition containing water, an oily component, gum arabic (unmodified gum arabic or modified gum arabic), and 0.01 mass % or more and less than 10 mass % of a salt (with the proviso that an emulsion composition containing carnauba wax is excluded), the method comprising:

(step 1) preparing an aqueous phase containing the water, the gum arabic, and the salt;

(step 2) preparing a mixture of the aqueous phase and the oily component; and (step 3) subjecting the mixture to an emulsification treatment.

The form or shape of the emulsion composition of the present invention is not particularly limited.

For example, the emulsion composition of the present invention may be in a liquid form or may be in a powder form by a powderization means.

The powderization can be performed according to a usual method, and, for example, a powderization means such as spray drying or freeze drying may be used. For powderization, an appropriate carrier or the like may be added.

The emulsion composition of the present invention can be used for various applications depending on, for example, the type of oily component. For example, when the oily component is a flavoring, the emulsion composition can be applied as an emulsified flavoring preparation. When the oily component is a colorant, the emulsion composition can be applied as an emulsified colorant preparation. When the oily component is a nutritional component (e.g., an oil-soluble vitamin or an oil-soluble amino acid), the emulsion composition can be applied as an emulsified nutrition fortifier preparation (a food additive used for the supplementation and enhancement of nutritional components)(e.g., an emulsified vitamin preparation or an emulsified amino acid preparation). When the oily component is a functional material, the emulsion composition can be applied as an emulsified functional material preparation. Moreover, the emulsion composition of the present invention can be applied as a clouding agent (also known as a turbidity agent or a cloudifier) for imparting appropriate cloudiness to aqueous media, such as drinks.

The particle diameter of emulsified particles of the emulsion composition of the present invention is not particularly limited and can be suitably adjusted depending on the intended use.

In one embodiment of the present invention, the emulsified particle diameter of the emulsion composition may be 3 μm or less, preferably 2.5 μm or less, more preferably 2 μm or less, and even more preferably 1.5 μm or less, in terms of median diameter (on a volume basis). Such an emulsion composition can be suitably used for, for example, drinks, desserts, frozen desserts, confectioneries (e.g., gum, chocolates, candies, cookies, and biscuits), bread, soups, seasonings, jams, fruit liquors, processed fruits, processed farm products, processed meats, processed fishery products, dairy products, milled products, noodles, liquid food, health food, or supplements.

In one preferable embodiment of the present invention, the emulsified particle diameter of the emulsion composition is 1.2 μm or less, preferably 1.1 μm or less, more preferably 1 μm or less, and even more preferably 0.9 μm or less, in terms of median diameter (on a volume basis). Such an emulsion composition can be suitably used for, for example, drinks.

The lower limit of the median diameter (on a volume basis) is not particularly limited and is, for example, 0.08 μm, preferably 0.1 μm or more, more preferably 0.12 μm or more, even more preferably 0.15 μm or more, still even more preferably 0.2 μm or more, and particularly preferably 0.3 μm or more.

[3] Aqueous Composition

The present invention also relates to an aqueous composition containing the emulsion composition.

The type of aqueous composition is not particularly limited and may be, for example, a food or drink, a cosmetic or fragrance (including a cosmetic), a pharmaceutical, or a quasi-drug. The type of aqueous composition is preferably a food or drink, and more preferably a drink.

The amount of the emulsion composition of the present invention in the aqueous composition may vary depending on the type, use, etc. of the composition and may be, for example, in the range of 0.001 to 5 mass % or 0.01 to 1 mass %.

[4] Food and Drink

The present invention also relates to a food or drink containing the emulsion composition.

The type of food or drink is not particularly limited. Specific examples of the food and drink include drinks such as milk drinks, *lactobacillus* drinks, carbonated drinks, fruit-containing drinks (e.g., fruit-juice-containing drinks, fruit-juice-containing soft drinks, fruit-juice-containing carbonated drinks, and fruit-pulp-containing drinks), vegetable-containing drinks, vegetable- and fruit-containing drinks, alcoholic drinks such as liqueur, coffee drinks, powdered drinks, sport drinks, and supplement drinks; tea drinks, such as black tea drinks, green tea drinks, and blended tea drinks (various drinks and tea drinks are included in "drinks"); puddings, such as custard pudding, milk pudding, or fruit-juice-containing pudding; desserts such as jellies, bavarois, or yogurt; frozen desserts, such as milk ice cream, fruit-juice-containing ice cream, soft-serve ice cream, and popsicles; confectioneries, such as gum (e.g., stick gum and sugar-coated gum granules), chocolates (e.g., flavored chocolates and coated chocolates), candies (e.g., hard candies, soft candies, sugar-coated candies, and taffy), cookies, biscuits, and doughnuts; bread; soups such as consommé soup and potage soup; liquid seasonings such as vinaigrette dressings, non-oil dressings, ketchup, gravy, and sauce; jams, such as strawberry jam, blueberry jam, marmalade, apple jam, apricot jam, preserves, and syrups; fruit liquors such as red wine; processed fruits such as candied cherries, apricots, apples, strawberries, and peaches; processed farm products such as pickles; processed meats, such as ham and sausage; processed fishery products, such as fish meat sausage, hanpen (cakes of pounded fish), chikuwa (tubular fish cakes), and boiled fish paste; dairy products; milled products (e.g., okonomiyaki (Japanese pancake) mix and takoyaki (octopus balls) mix); noodles; liquid food; health food; and supplements.

The type of food or drink is particularly preferably a drink, a dessert (particularly preferably a jelly), a candy, a jam, pickles, or a liquid seasoning, and more preferably a drink.

The examples of the food and drink also include semi-finished products, intermediate products, etc. of these products.

Oil-containing particles derived from the emulsion composition of the present invention are suitably present in the food or drink.

7: Method for Improving Emulsion Stability of Emulsion Composition (Emulsion Stability Improvement Method)

The present invention also relates to the following method for improving the emulsion stability of an emulsion composition:

A method for improving the emulsion stability of an emulsion composition containing water, an oily component, and unmodified or modified gum arabic (with the proviso that an emulsion composition containing carnauba wax is excluded), the method comprising adding a salt to the composition in such an amount that the salt content is 0.01 mass % or more and less than 10 mass %.

This method may be the same as or similar to the embodiments of the emulsion composition of the present invention and the preparation method described above, and can be understood by referring to the method for preparing the emulsion composition according to the present invention described above.

The method for improving the emulsion stability of an emulsion composition according to the present invention preferably includes an embodiment in which the step of incorporating a salt is performed before formation of emulsified particles.

The method for improving the emulsion stability of an emulsion composition according to the present invention includes the following preferable embodiment:

A method for improving the emulsion stability of an emulsion composition containing gum arabic, the method comprising:
1) preparing a mixture containing water, an oily component, gum arabic, and salt; and
2) subjecting the mixture to an emulsification treatment to prepare an emulsion composition.

Specific examples of the preferable embodiment include the following examples:
A) in steps 1 and 2, a salt is added to a mixed composition containing water, an oily component, and gum arabic, and an emulsification treatment is performed to preparing an emulsion composition;
B) in steps 1 and 2, gum arabic is added to a mixed composition containing water, an oily component, and a salt, and an emulsification treatment is performed to prepare an emulsion composition;

C) in steps 1 and 2, an oily component is added to a mixed composition containing water, gum arabic, and a salt, and an emulsification treatment is performed to prepare an emulsion composition; and D) in steps 1 and 2, water is added to a mixed composition containing an oily component, gum arabic, and a salt, and an emulsification treatment is performed to prepare an emulsion composition.

Although this is stated just to be sure, in these examples (in particular, example A and example B), each mixed composition described above may be subjected to the emulsification treatment. In this case, after addition of a further component, a further emulsification treatment may be performed, or a mere mixing treatment may be performed.

These embodiments and examples may overlap with each other.

EXAMPLES

The present invention is more specifically explained below with reference to Examples. The scope of the present invention is, however, not limited to these examples.

In the tables of the following Examples, numerals indicating formulations are mass % unless otherwise specified.

The following abbreviations may be used in the Examples.
GumA: Unmodified gum arabic
DGFE: Decaglycerin fatty acid ester An Example of embodiment A of the present invention is shown below.
Materials
Gum arabic: Gum arabic having different molecular weights (molecular weight of 0.80 million, 1.10 million, 1.50 million, and 4.00 million) was prepared. The molecular weights were calculated by the GPC-MALLS method described in this specification.
Medium-chain triglyceride (ODO): Caprylic acid/capric acid=3/1, produced by Nisshin OilliO Group, Ltd.
Emulsion Stability Test
Evaluation of Emulsifiability The prepared emulsion composition was evaluated as a drink model in terms of the following items.
D50 μm or a particle size D50: median diameter
0.1.3 μm↑ or 1.3μ↑: Frequency of a particle size of 1.3 μm or more
0.1% E (720 nm): Turbidity of a 0.1% aqueous diluent of a sample (emulsion composition) at 720 nm "D50 μm" and "1.3 μm↑" were found by measuring the particle size distribution of the emulsion composition under the following conditions.
Particle-Size Distribution Analyzer: Microtrac MT3000EX-II (MicrotracBEL Corp.)
Measurement Method: Refraction Index=1.81, Measurement Range=0.021 to 2000 μm, Volumetric Basis "0.1% E (720 nm)" was found by using a 0.1% aqueous solution of each sample (emulsion composition), which was obtained by diluting the sample with ion-exchanged water, and measuring the turbidity of the diluent at 720 nm under the following conditions.
Spectrophotometer: V-660DS spectrophotometer, produced by JASCO Corporation
Measurement Conditions: Quartz cell, 10 mm×10 mm, Absorbance (Abs)
Evaluation of Emulsion Storage Stability The prepared emulsion composition was placed in a 30-mL glass bottle to fill and stored in a constant-temperature bath at 60° C. The evaluation was performed in terms of the following items using the emulsion composition three days and seven days after the storage.

Figure 2:
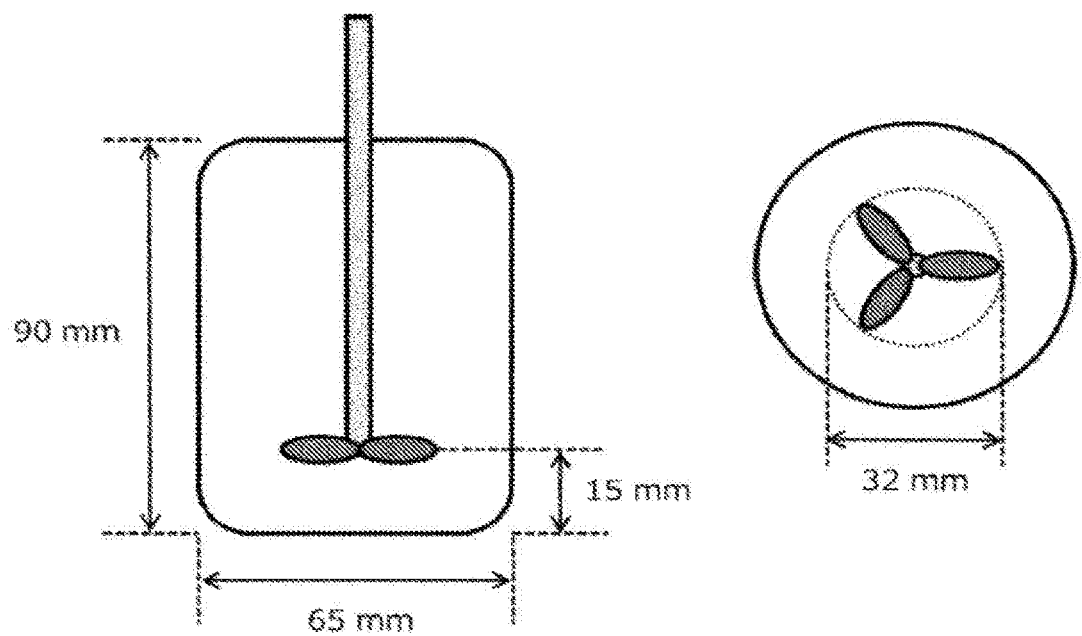
FIG. 2: A schematic diagram showing a test for evaluating emulsion physical stability (accelerated test). The figure on the left is a lateral view and the figure on the right is an upper view of the test system.

D50 μm or a particle size D50: median diameter; the unit of the numbers in the tables is μm.
1.3 μm↑: Frequency of a particle size of 1.3 μm or more The unit in the tables is %.
0.1% E (720 nm): Turbidity of a 0.1% aqueous diluent of a sample (emulsion composition) at 720 nm The preferable range of turbidity as a clouding agent is 0.2 to 0.8.
Evaluation of Emulsion Physical Stability An accelerated test was performed to evaluate, as one of the indices of emulsion physical stability, changes of emulsified particles when the emulsion composition was stirred under a high temperature condition. FIG. 2 shows a schematic diagram.
Instruments: 200-mL beaker (glass beaker, diameter=65 mm, height=90 mm)
Stirring blade (a metal rod having a diameter of 5 mm with three blades having a diameter of 32 mm on the top end)
Measurement method:
1) 200 g of a sample (emulsion composition) is weighed and placed in a 200 mL beaker.
2) The sample is allowed to stand at 60° C. for 20 minutes.
3) A blade is placed in a portion 15 mm high from the bottom of the 200-mL beaker.
4) The sample is stirred with the stirring blade at a rotation rate of 1300 rpm.
5) The emulsion composition is sampled for a predetermined time (0 minutes, 3 minutes, and 6 minutes).

The particle size distribution is measured.
Particle-Size Distribution Analyzer: Microtrac MT3000EX-II (MicrotracBEL Corp.)
Measurement Method: Refraction Index=1.81, Measurement Range=0.021 to 2000 μm, Volumetric Basis
Evaluation of Emulsion Stability Tables A1 and A2 below show evaluation criteria in the evaluation of emulsion stability in each Example.

"Evaluation (changes over time)" was performed using a difference (score difference) between an "emulsion state (evaluation score)" immediately after the preparation (initial sample) of an emulsion composition (drink model) and an emulsion state (evaluation score) of the emulsion composition at the time of evaluation (after the test of the emulsion storage stability or after the test of the emulsion physical stability) as an index.

Further, the "evaluation (changes over time) was performed by grading samples having an initial sample evaluation score of 3 or more (better than normal) in 4 levels, i.e., ××, ×, ○, and ◉, and grading samples having an initial sample evaluation score of less than 3 as "–".

TABLE A1

| Evaluation Score (Emulsion State) | D50 μm | 1.3 μm↑ |
| --- | --- | --- |
| 5: Excellent | 0.9 μm or less | Not more than 10% |
| 4: Very Good | More than 0.9 μm to not more than 1.0 μm | More than 10% to not more than 20% |
| 3: Acceptable | More than 1.0 μm to not more than 1.2 μm | More than 20% to not more than 35% |
| 2: Bad | More than 1.2 μm to not more than 2.0 μm | More than 35% to not more than 50% |
| 1: Very Bad | More than 2.0 μm- | More than 50%- |

TABLE A2

| Evaluation (Changes Over Time) | Difference in Evaluation Score (Emulsion State) |
|---|---|
| ◎: Very Stable | 0 |
| ○: Stable | −1 |
| X: Relatively Unstable | −2 |
| XX: Unstable | Not more than −3 |
| — | A score of less than 3 for Initial Sample |

Method for Producing Emulsion Composition (Drink Model)

The emulsion compositions (drink model) were produced according to the formulations in the respective tables. The materials shown in the formulations were stirred at 3000 rpm for 5 minutes, thereby preparing a mixed liquid. Subsequently, the mixed liquid was homogenized with a high-pressure homogenizer (15MR-8TA homogenizer, produced by Manton-Gaulin Co., Ltd.) (350 kg/cm$^2$, 5 times), thereby producing an emulsion composition.

Test Example A: Gum Arabic Molecular Weight

Preparation of Emulsion Composition

The emulsion compositions (drink model) were prepared according to the formulation in Table A3.

An emulsion stability test was performed using the prepared emulsion composition.

Figure 3:
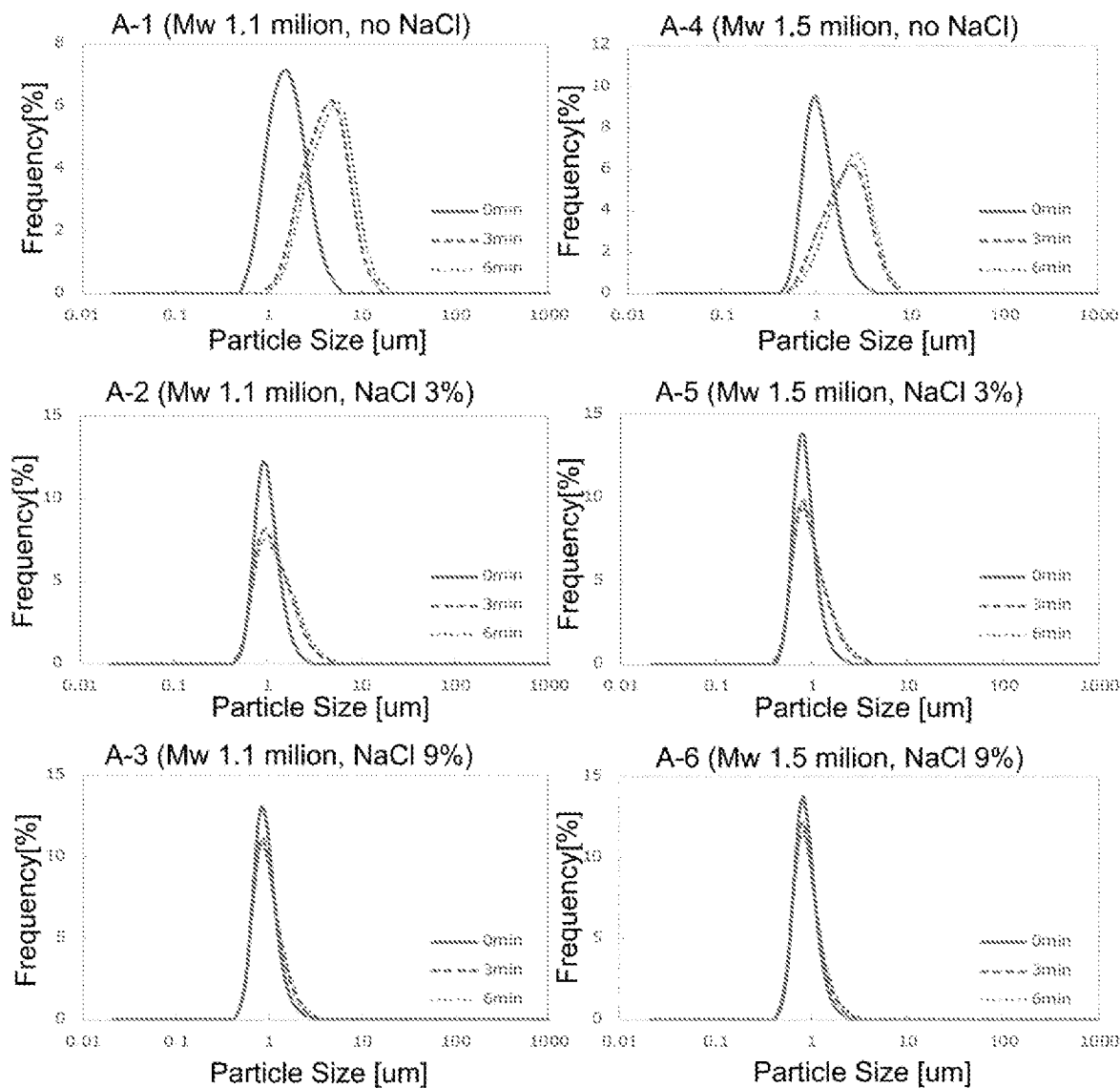
FIG. 3: Results (particle size distribution) of the emulsion physical stability test for samples A-1 to A-6 in Test Example A.
Figure 4:
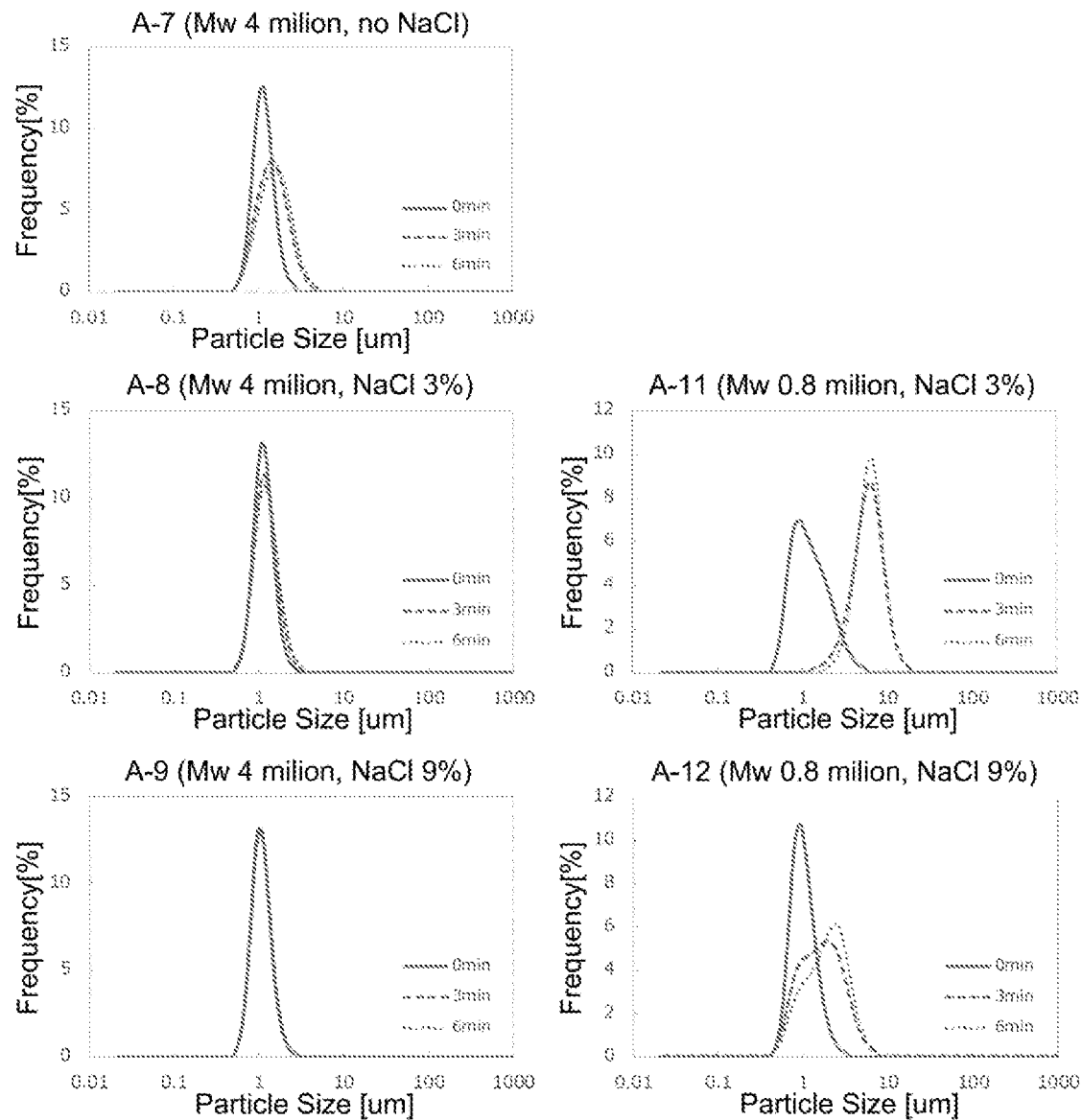
FIG. 4: Results (particle size distribution) of the emulsion physical stability test for samples A-7 to A-9 and A-11 to A-12 in Test Example A.

The test results for emulsifiability and emulsion storage stability are shown in Tables A4 and A5, and the results of the emulsion physical stability test are shown in Tables A6, and FIGS. 3 and 4.

The pH of the emulsion compositions A-1 to A-12 was within the range of 2.5 to 3.5.

TABLE A3

| Formulation | Mass % |
|---|---|
| Medium-Chain Triglyceride | 15 |
| GumA(Molecular Weight: see Tables 4-6) | 17.5 |
| Sodium Chloride | See Tables A4-6 |
| Citric Acid (Anhydrous) | 0.5 |
| Propylene Glycol | 10 |
| Ion-Exchanged Water (added to result in 100%) | 100 |

TABLE A4

| Sample No. | GumA Molecular Weight [×10$^4$] | NaCl (%) | Initial Sample | | | 3 Days at 60° C. | | | 7 Days at 60° C. | | |
|---|---|---|---|---|---|---|---|---|---|---|---|
| | | | D50 | 1.3µ ↑ | 0.1% E | D50 | 1.3µ ↑ | 0.1% E | D50 | 1.3µ ↑ | 0.1% E |
| A-1 | 110 | 0 | 1.20 | 44 | 0.54 | 1.47 | 65 | 0.59 | 1.63 | 75 | 0.60 |
| A-2 | 110 | 3 | 0.92 | 16 | 0.49 | 0.97 | 22 | 0.51 | 1.05 | 31 | 0.51 |
| A-3 | 110 | 9 | 0.84 | 9 | 0.44 | 0.83 | 9 | 0.45 | 0.87 | 14 | 0.45 |
| A-4 | 150 | 0 | 0.95 | 21 | 0.48 | 1.07 | 33 | 0.50 | 1.15 | 41 | 0.52 |
| A-5 | 150 | 3 | 0.78 | 6 | 0.41 | 0.81 | 11 | 0.43 | 0.84 | 15 | 0.44 |
| A-6 | 150 | 9 | 0.80 | 8 | 0.42 | 0.82 | 8 | 0.42 | 0.82 | 10 | 0.42 |
| A-7 | 400 | 0 | 1.08 | 29 | 0.56 | 1.13 | 36 | 0.58 | 1.21 | 45 | 0.58 |
| A-8 | 400 | 3 | 1.07 | 27 | 0.59 | 1.10 | 32 | 0.59 | 1.15 | 39 | 0.59 |
| A-9 | 400 | 9 | 1.01 | 21 | 0.55 | 1.01 | 27 | 0.54 | 1.00 | 21 | 0.54 |
| A-10 | 80 | 0 | 2.48 | 87 | 0.55 | 2.40 | 94 | 0.62 | 2.46 | 96 | 0.65 |
| A-11 | 80 | 3 | 0.95 | 25 | 0.48 | 1.12 | 39 | 0.52 | 1.18 | 42 | 0.54 |
| A-12 | 80 | 9 | 0.91 | 16 | 0.47 | 0.94 | 18 | 0.49 | 0.98 | 22 | 0.50 |

TABLE A5

| Sample No. | GumA Molecular Weight [×10$^4$] | NaCl (%) | Initial Sample Evaluation Score | | 3 Days at 60° C. Evaluation Score (Evaluation) | | 7 Days at 60° C. Evaluation Score (Evaluation) | |
|---|---|---|---|---|---|---|---|---|
| | | | D50 | 1.3µ ↑ | D50 | 1.3µ ↑ | D50 | 1.3µ ↑ |
| A-1 | 110 | 0 | 3 | 2 | 2 (○) | 1 (—) | 2 (○) | 1 (—) |
| A-2 | 110 | 3 | 4 | 4 | 4 (◎) | 3 (○) | 3 (○) | 3 (○) |
| A-3 | 110 | 9 | 5 | 5 | 5 (◎) | 5 (◎) | 5 (◎) | 4 (○) |
| A-4 | 150 | 0 | 4 | 3 | 3 (○) | 3 (◎) | 3 (○) | 2 (○) |
| A-5 | 150 | 3 | 5 | 5 | 5 (◎) | 4 (○) | 5 (◎) | 4 (○) |
| A-6 | 150 | 9 | 5 | 5 | 5 (◎) | 5 (◎) | 5 (◎) | 5 (◎) |
| A-7 | 400 | 0 | 3 | 3 | 3 (◎) | 2 (○) | 2 (○) | 2 (○) |
| A-8 | 400 | 3 | 3 | 3 | 3 (◎) | 3 (◎) | 3 (◎) | 2 (○) |
| A-9 | 400 | 9 | 3 | 3 | 3 (◎) | 3 (◎) | 4 (◎) | 3 (◎) |
| A-10 | 80 | 0 | 1 | 1 | 1 (—) | 1 (—) | 1 (—) | 1 (—) |
| A-11 | 80 | 3 | 4 | 3 | 3 (○) | 2 (○) | 3 (○) | 2 (○) |
| A-12 | 80 | 9 | 4 | 4 | 4 (◎) | 4 (◎) | 4 (◎) | 3 (○) |

TABLE A6

| Sample No. | GumA Molecular Weight [×10⁴] | NaCl (%) | Initial Sample (0 Minutes) D50 | Initial Sample (0 Minutes) 1.3μ↑ | 3 Minutes D50 | 3 Minutes 1.3μ↑ | 6 Minutes D50 | 6 Minutes 1.3μ↑ |
|---|---|---|---|---|---|---|---|---|
| A-1 | 110 | 0 | 1.46 | 62 | 3.89 | 98 | 4.44 | 99 |
| A-2 | 110 | 3 | 0.92 | 16 | 1.05 | 35 | 1.10 | 40 |
| A-3 | 110 | 9 | 0.84 | 10 | 0.87 | 10 | 0.88 | 18 |
| A-4 | 150 | 0 | 1.01 | 29 | 2.01 | 78 | 2.25 | 88 |
| A-5 | 150 | 3 | 0.78 | 6 | 0.86 | 20 | 0.87 | 22 |
| A-6 | 150 | 9 | 0.81 | 8 | 0.83 | 11 | 0.84 | 14 |
| A-7 | 400 | 0 | 1.10 | 30 | 1.39 | 59 | 1.50 | 65 |
| A-8 | 400 | 3 | 1.07 | 27 | 1.13 | 36 | 1.15 | 39 |
| A-9 | 400 | 9 | 1.01 | 20 | 1.01 | 22 | 1.01 | 22 |
| A-10 | 80 | 0 | — | — | — | — | — | — |
| A-11 | 80 | 3 | 1.10 | 41 | 5.73 | 100 | 5.96 | 100 |
| A-12 | 80 | 9 | 0.94 | 21 | 1.58 | 63 | 1.90 | 72.66 |

The salt contents in the samples with 3% and 9% sodium chloride based on 100 parts by mass of gum arabic are 17.1 parts by mass and 51.4 parts by mass, respectively.

Tables A4 and A5 confirmed that the emulsion stability of emulsion compositions using gum arabic having molecular weights of $110\times10^4$, $150\times10^4$ and $400\times10^4$ and a specific amount of sodium chloride were superior to that of an emulsion composition that does not contain sodium chloride. Regarding the emulsifiability, the particle size tends to decrease by having sodium chloride added. Regarding the emulsion storage stability, the variation in emulsified particles (D50, 1.3 μm↑) tends to decrease compared with the sample with no addition of sodium chloride. In contrast, the emulsion stability of an emulsion composition using gum arabic having a molecular weight of $80\times10^4$ was not regarded as sufficient, compared with an emulsion composition using gum arabic having a molecular weight of $110\times10^4$ or more.

Table A6, and FIGS. 3 and 4 show the results of the emulsion physical stability test. It was confirmed that the particle size distribution of the emulsion compositions using gum arabic having molecular weights of $110\times10^4$, $150\times10^4$ and $400\times10^4$ and a specific amount of sodium chloride after the accelerated test (3 and 6 minutes after the test) did not greatly vary. This indicated that the sample was superior in emulsion physical stability.

In contrast, it was confirmed that the particle size distribution of the emulsion composition using gum arabic having a molecular weight of $80\times10^4$ varied despite the incorporation of a specific amount of sodium chloride, and that the emulsified particle diameter increased.

Test Example B: Salt Content (1)

Preparation of Emulsion Composition

An emulsion composition was prepared according to the formulation shown in Table A7.

An emulsion stability test was performed using the prepared emulsion composition.

Figure 5:
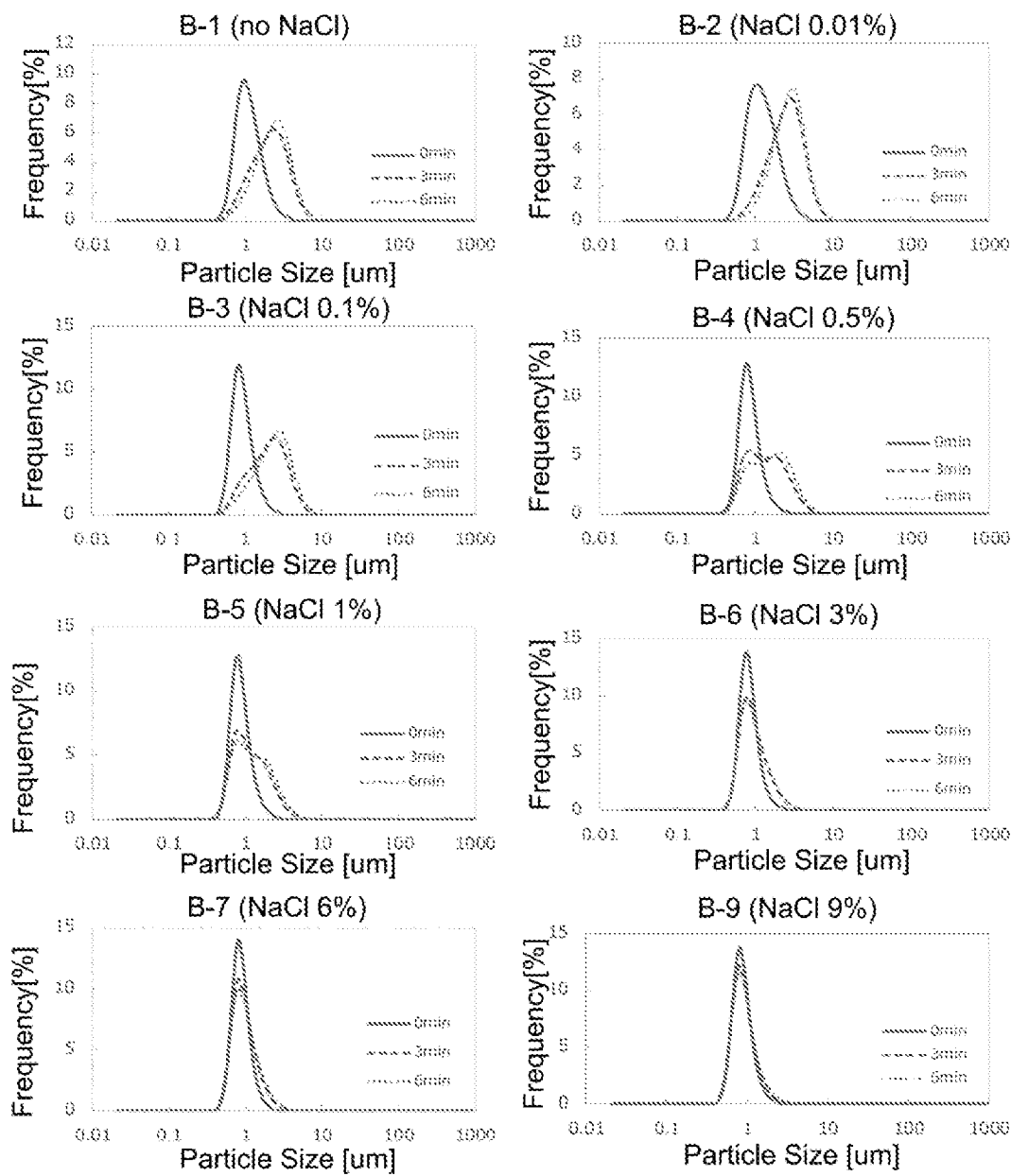
FIG. 5: Results (particle size distribution) of the emulsion physical stability test for samples B-1 to B-7 and B-9 in Test Example B.

The test results for emulsifiability and emulsion storage stability are shown in Tables A8 and A9, and the results of the emulsion physical stability test are shown in Table A10 and FIG. 5.

The pH of B-1 to B-11 was within the range of 2.5 to 3.5.

TABLE A7

| Formulation | Mass % |
|---|---|
| Medium-Chain Triglyceride | 15 |
| GumArabic (Molecular Weight: $150 \times 10^4$) | 17.5 |
| Sodium Chloride | See Tables A8-10 |
| Citric Acid (Anhydrous) | 0.5 |
| Propylene Glycol | 10 |
| Ion-Exchanged Water (added to result in 100%) | 100 |

TABLE A8

| Sample No. | NaCl (%) | Salt Content (part) per 100 parts of GumA | D50 [μm] Initial Sample | D50 [μm] 3 Days at 60° C. | D50 [μm] 7 Days at 60° C. | 1.3μ↑ [%] Initial Sample | 1.3μ↑ [%] 3 Days at 60° C. | 1.3μ↑ [%] 7 Days at 60° C. |
|---|---|---|---|---|---|---|---|---|
| B-1 | 0 | 0 | 0.95 | 1.07 | 1.15 | 21 | 33 | 41 |
| B-2 | 0.01 | 0.06 | 0.97 | 1.01 | 1.18 | 23 | 35 | 43 |
| B-3 | 0.1 | 0.6 | 0.83 | 0.95 | 1.07 | 10 | 25 | 37 |
| B-4 | 0.5 | 2.9 | 0.77 | 0.87 | 0.95 | 7 | 16 | 28 |
| B-5 | 1 | 5.7 | 0.78 | 0.85 | 0.91 | 7 | 16 | 22 |
| B-6 | 3 | 17.1 | 0.78 | 0.81 | 0.84 | 6 | 11 | 15 |
| B-7 | 6 | 34.2 | 0.81 | 0.83 | 0.86 | 7 | 9 | 14 |
| B-8 | 8 | 45.7 | 0.84 | 0.86 | 0.87 | 9 | 10 | 12 |
| B-9 | 9 | 51.4 | 0.80 | 0.82 | 0.82 | 8 | 8 | 10 |
| B-10 | 12 | 68.6 | 0.83 | 0.83 | 0.83 | 8 | 9 | 9 |
| B-11 | 14.5 | 82.9 | 0.79 | 0.80 | 0.80 | 6 | 7 | 7 |

TABLE A9

| Sample No. | NaCl (%) | Salt Content (part) per 100 parts of GumA | D50 [μm] Evaluation Score (Evaluation) Initial Sample | D50 [μm] Evaluation Score (Evaluation) 3 Days at 60° C. | D50 [μm] Evaluation Score (Evaluation) 7 Days at 60° C. | 1.3μ↑ [%] Evaluation Score (Evaluation) Initial Sample | 1.3μ↑ [%] Evaluation Score (Evaluation) 3 Days at 60° C. | 1.3μ↑ [%] Evaluation Score (Evaluation) 7 Days at 60° C. |
|---|---|---|---|---|---|---|---|---|
| B-1 | 0 | 0 | 4 | 3 (◯) | 3 (◯) | 3 | 3 (⊚) | 2 (◯) |
| B-2 | 0.01 | 0.06 | 4 | 3 (◯) | 3 (◯) | 3 | 3 (⊚) | 2 (◯) |

TABLE A9-continued

| Sample No. | NaCl (%) | Salt Content (part) per 100 parts of GumA | D50 [μm] Evaluation Score (Evaluation) | | | 1.3μ↑ [%] Evaluation Score (Evaluation) | | |
|---|---|---|---|---|---|---|---|---|
| | | | Initial Sample | 3 Days at 60° C. | 7 Days at 60° C. | Initial Sample | 3 Days at 60° C. | 7 Days at 60° C. |
| B-3 | 0.1 | 0.6 | 5 | 4 (○) | 3 (X) | 5 | 3 (X) | 2 (XX) |
| B-4 | 0.5 | 2.9 | 5 | 5 (⊚) | 4 (○) | 5 | 4 (○) | 3 (X) |
| B-5 | 1 | 5.7 | 5 | 5 (⊚) | 4 (○) | 5 | 4 (○) | 3 (X) |
| B-6 | 3 | 17.1 | 5 | 5 (⊚) | 5 (⊚) | 5 | 4 (○) | 4 (○) |
| B-7 | 6 | 34.2 | 5 | 5 (⊚) | 5 (⊚) | 5 | 5 (⊚) | 4 (○) |
| B-8 | 8 | 45.7 | 5 | 5 (⊚) | 5 (⊚) | 5 | 5 (⊚) | 4 (○) |
| B-9 | 9 | 51.4 | 5 | 5 (⊚) | 5 (⊚) | 5 | 5 (⊚) | 5 (⊚) |
| B-10 | 12 | 68.6 | 5 | 5 (⊚) | 5 (⊚) | 5 | 5 (⊚) | 5 (⊚) |
| B-11 | 14.5 | 82.9 | 5 | 5 (⊚) | 5 (⊚) | 5 | 5 (⊚) | 5 (⊚) |

The results of Tables A8 and A9 confirmed that the emulsifiability and emulsion storage stability of the emulsion composition were improved by having a predetermined amount of sodium chloride added. In the emulsion compositions having sodium chloride content of 12 mass % and 14.5 mass % (samples B-10 and B-11), precipitation of sodium chloride was partially observed. It was suggested that the sodium chloride content is preferably 12 mass % or less in terms of the quality of the emulsion composition.

TABLE A10

| Sample No. | NaCl (%) | Salt Content (part) per 100 parts of GumA | 0 Minutes | | 3 Minutes | | 6 Minutes | |
|---|---|---|---|---|---|---|---|---|
| | | | D50 | 1.3μ↑ | D50 | 1.3μ↑ | D50 | 1.3μ↑ |
| B-1 | 0 | 0 | 1.01 | 29 | 2.01 | 78 | 2.25 | 85 |
| B-2 | 0.01 | 0.06 | 1.15 | 42 | 2.47 | 88 | 2.71 | 93 |
| B-3 | 0.1 | 0.6 | 0.84 | 12 | 1.95 | 74 | 2.28 | 83 |
| B-4 | 0.5 | 2.9 | 0.80 | 9 | 1.27 | 50 | 1.51 | 59 |
| B-5 | 1 | 5.7 | 0.80 | 9 | 1.04 | 38 | 1.14 | 44 |
| B-6 | 3 | 17.1 | 0.78 | 6 | 0.86 | 20 | 0.87 | 22 |
| B-7 | 6 | 34.2 | 0.82 | 7 | 0.87 | 17 | 0.88 | 20 |
| B-9 | 9 | 51.4 | 0.81 | 8 | 0.83 | 11 | 0.84 | 14 |

Table A10 and FIG. 5 show the results of the emulsion physical stability test for samples B-1 to B-7 and B-9. It was confirmed that when the sodium chloride content was 3 mass % or more (i.e., the salt content based on 100 parts by mass of gum arabic was 17.1 parts by mass), the emulsion physical stability was significantly improved.

Test Example C: Salt Content (2)

Preparation of Emulsion Composition

An emulsion composition was prepared according to the formulation shown in Table A11.

An emulsion stability test was performed using the prepared emulsion composition.

The test results for emulsifiability and emulsion storage stability are shown in Tables A12 and A13.

The pH of C-1 to C-4 was within the range of 2.5 to 3.5.

TABLE A11

| Formulation | Mass % |
|---|---|
| Medium-Chain Triglyceride | 15 |
| GumArabic (Molecular Weight: 1.50 million) | 17.5 |
| Sodium Chloride | See Tables A12-13 |
| Citric Acid (Anhydrous) | 0.5 |
| Glycerin | 20 |
| Ion-Exchanged Water (added to result in 100%) | 100 |

TABLE A12

| Sample No. | NaCl (%) | Salt Content (part) per 100 parts of GumA | D50 [μm] | | | 1.3μ↑ [%] | | |
|---|---|---|---|---|---|---|---|---|
| | | | Initial Sample | 3 Days at 60° C. | 7 Days at 60° C. | Initial Sample | 3 Days at 60° C. | 7 Days at 60° C. |
| C-1 | 0.1 | 0.6 | 0.72 | 0.76 | 0.80 | 5 | 11 | 18 |
| C-2 | 3 | 17.1 | 0.65 | 0.66 | 0.66 | 3 | 4 | 4 |
| C-3 | 8 | 45.7 | 0.56 | 0.56 | 0.56 | 2 | 2 | 2 |
| C-4 | 11.5 | 65.7 | 0.50 | 0.51 | 0.51 | 1 | 1 | 1 |

TABLE A13

| Sample No. | NaCl (%) | Salt Content (part) per 100 parts of GumA | D50 [μm] Evaluation Score (Evaluation) | | | 1.3μ↑ [%] Evaluation Score (Evaluation) | | |
|---|---|---|---|---|---|---|---|---|
| | | | Initial Sample | 3 Days at 60° C. | 7 Days at 60° C. | Initial Sample | 3 Days at 60° C. | 7 Days at 60° C. |
| C-1 | 0.1 | 0.6 | 5 | 5 (◉) | 5 (◉) | 5 | 4(○) | 4(○) |
| C-2 | 3 | 17.1 | 5 | 5 (◉) | 5 (◉) | 5 | 5 (◉) | 5 (◉) |
| C-3 | 8 | 45.7 | 5 | 5 (◉) | 5 (◉) | 5 | 5 (◉) | 5 (◉) |
| C-4 | 11.5 | 65.7 | 5 | 5 (◉) | 5 (◉) | 5 | 5 (◉) | 5 (◉) |

Tables A12 and A13 confirmed that the emulsifiability and emulsion storage stability of the emulsion composition were improved by adding a predetermined amount of sodium chloride.

Test Example D: Emulsifier Other than Gum Arabic

Preparation of Emulsion Composition

An emulsion composition was prepared according to the formulation shown in Table A14.

An emulsion stability test was performed using the prepared emulsion composition.

The test results for emulsifiability and emulsion storage stability are shown in Tables A15 and A16.

TABLE A14

| Formulation Mass % | D-1 | D-2 | D-3 | D-4 | D-5 | D-6 |
|---|---|---|---|---|---|---|
| Medium-Chain Triglyceride | 15 | 15 | 15 | 15 | 15 | 15 |
| GumA (Molecular Weight: 150 × 10$^4$) | 17.5 | 17.5 | 17.5 | 17.5 | — | — |
| DGFE | — | — | — | — | 17.5 | 17.5 |
| Sodium Chloride | — | 8 | — | 8 | — | 8 |
| Propylene Glycol | — | — | 10 | 10 | — | — |
| Ion-Exchanged Water (added to result in 100%) | 100 | 100 | 100 | 100 | 100 | 100 |

TABLE A15

| Sample No. | Emulsifier | Propylene Glycol (%) | NaCl (%) | Salt Content (part) per 100 parts of Emulsifier | D50 [μm] | | | 1.3μ↑ [%] | | |
|---|---|---|---|---|---|---|---|---|---|---|
| | | | | | Initial Sample | 3 Days at 60° C. | 7 Days at 60° C. | Initial Sample | 3 Days at 60° C. | 7 Days at 60° C. |
| D-1 | GumA | 0 | 0 | 0 | 0.41 | 0.51 | 0.72 | 1 | 20 | 36 |
| D-2 | GumA | 0 | 8 | 45.7 | 0.54 | 0.72 | 0.73 | 4 | 10 | 13 |
| D-3 | GumA | 10 | 0 | 0 | 0.88 | 1.11 | 1.12 | 15 | 41 | 45 |
| D-4 | GumA | 10 | 8 | 45.7 | 0.88 | 0.90 | 0.92 | 12 | 14 | 16 |
| D-5 | DGFE | 0 | 0 | 0 | 0.13 | — | — | 0 | — | — |
| D-6 | DGFE | 0 | 8 | 45.7 | 16.54 | ND | ND | 100 | ND | ND |

ND: unmeasurable

TABLE A16

| Sample No. | Emulsifier | Propylene Glycol (%) | NaCl (%) | Salt Content (part) per 100 parts of Emulsifier | D50 [μm] Evaluation Score (Evaluation) | | | 1.3μ↑ [%] Evaluation Score (Evaluation) | | |
|---|---|---|---|---|---|---|---|---|---|---|
| | | | | | Initial Sample | 3 Days at 60° C. | 7 Days at 60° C. | Initial Sample | 3 Days at 60° C. | 7 Days at 60° C. |
| D-1 | GumA | 0 | 0 | 0 | 5 | 5 (◉) | 5 (◉) | 5 | 3 (X) | 2 (XX) |
| D-2 | GumA | 0 | 8 | 45.7 | 5 | 5 (◉) | 5 (◉) | 5 | 5 (◉) | 4 (○) |
| D-3 | GumA | 10 | 0 | 0 | 5 | 3 (X) | 3 (X) | 4 | 2 (X) | 2 (X) |
| D-4 | GumA | 10 | 8 | 45.7 | 5 | 5 (◉) | 4 (○) | 4 | 4 (○) | 4 (○) |
| D-5 | DGFE | 0 | 0 | 0 | 5 | — | — | 5 | — | — |
| D-6 | DGFE | 0 | 8 | 45.7 | 1 | ND | ND | 100 | ND | ND |

ND: unmeasurable

The results for D-1 to D-4 using gum arabic having a molecular weight of 1.50 million revealed that the emulsion stability (emulsifiability and emulsion storage stability) of the emulsion composition was improved by adding a predetermined amount of salt.

In emulsion composition (D-5), which contains, as an emulsifier, decaglycerin fatty acid ester, which is generally used, and which does not contain sodium chloride, the emulsified particle diameter (D50) was small, namely, 0.13 µm, and the emulsion composition did not have desirable turbidity as a clouding agent. The turbidity (0.1% E (720 nm)) of D-5 was measured and found to be 0.095, and a 0.1% aqueous solution thereof was transparent.

In emulsion composition (D-6), which contains decaglycerin fatty acid ester and also contains sodium chloride, a part of the oil phase was separated after the homogenization treatment, and a uniform emulsion composition could not be prepared. The particle size distribution in the emulsified portion of the emulsion composition was measured. The emulsified particle diameter (D50) was significantly large, namely, 16.54.

These results revealed that addition of sodium chloride generally serves to inhibit the emulsification of an emulsion composition, as known by conventional technical standards.

D-1 and D-2 are free of propylene glycol as polyhydric alcohol. D-3 and D-4 are emulsion compositions containing propylene glycol. A comparison between D-1 and D-3 revealed that the emulsified particle diameter immediately after the preparation was 0.41 µm (no addition of propylene glycol) and 0.88 µm (with propylene glycol), and that, therefore, the addition of propylene glycol decreased the emulsifiability. It was also revealed that the emulsion storage stability (1.3 µm↑) was 1% (no addition of propylene glycol) and 15% (with propylene glycol), and that, therefore, the addition of propylene glycol also decreased the emulsion storage stability.

On the other hand, it was revealed that the emulsifiability and the emulsion storage stability were improved by further using sodium chloride in the sample in which propylene glycol was added.

Test Example E: Oil/Fat Content

Preparation of Emulsion Composition

An emulsion composition was prepared according to the formulation shown in Table A17.

Figure 6:
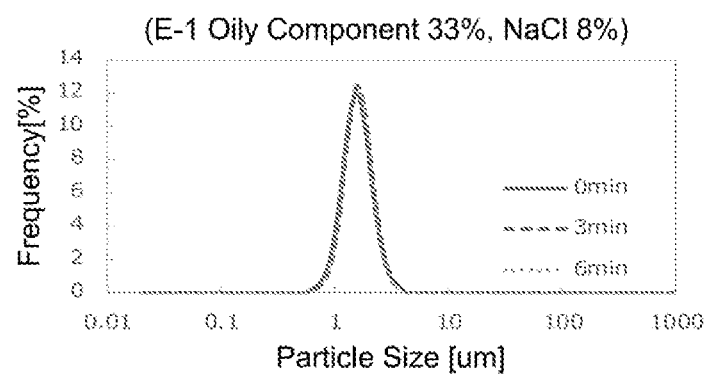
FIG. 6: Results (particle size distribution) of the emulsion physical stability test for sample E-1 in Test Example E.

An emulsion stability test (emulsion physical stability test) was performed using the prepared emulsion composition. FIG. 6 shows the results.

TABLE A17

| Formulation Mass % | E-1 |
|---|---|
| Medium-Chain Triglyceride | 33 |
| GumArabic (Molecular Weight: 150 × 10$^4$) | 17.5 |
| Sodium Chloride | 8 |
| Ion-Exchanged Water (added to result in 100%) | 100 |
| Salt Content (part) per 100 parts of GumArabic | 45.71 |

FIG. 6 revealed that an emulsion composition having significantly superior emulsion physical stability can be prepared by incorporating gum arabic having a molecular weight of $150 \times 10^4$ and a predetermined amount of sodium chloride.

Test Example F: Types of Salt

Preparation of Emulsion Composition

An emulsion composition was prepared according to the formulation shown in Table A18.

An emulsion stability test was performed using the prepared emulsion composition.

Figure 7:
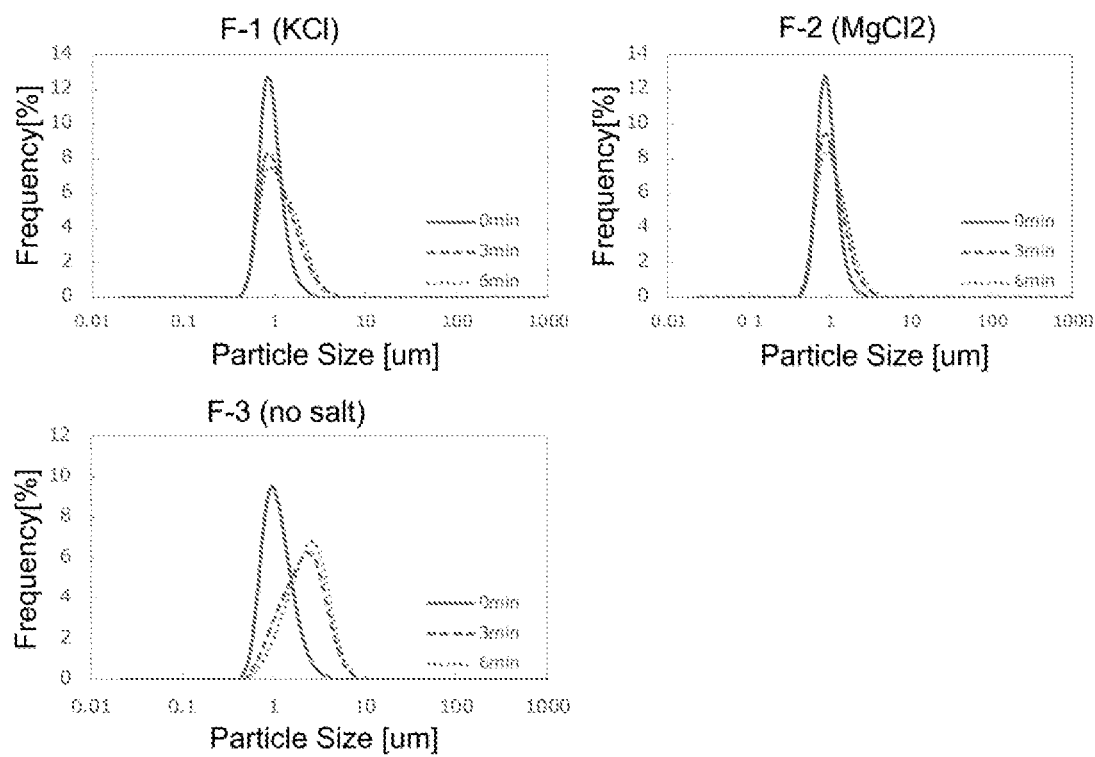
FIG. 7: Results (particle size distribution) of the emulsion physical stability test for samples F-1 to F-3 in Test Example F.

The test results for emulsifiability and emulsion storage stability are shown in Tables A19 and A20, and the results of the emulsion physical stability test are shown in Tables A21 and FIG. 7.

The pH of the emulsion compositions F-1 and F-2 was 3.0 and 2.6, respectively.

The turbidities (0.1% E (720 nm)) of the emulsion compositions F-1 to F-2 were within the range of 0.45 to 0.49 from the initial day (immediately after the preparation) throughout the 7-day storage at 60° C.

TABLE A18

| Formulation | Mass % |
|---|---|
| Medium-Chain Triglyceride | 15 |
| GumA (Molecular Weight: 150 × 10$^4$) | 17.5 |
| Salt | See Tables A19-21 |
| Citric Acid (Anhydrous) | 0.5 |
| Propylene Glycol | 10 |
| Ion-Exchanged Water (added to result in 100%) | 100 |

TABLE A19

| Sample No. | Salt | Salt Content (%) | Salt Content (part) per 100 parts of GumA | D50 [µm] Initial Sample | D50 [µm] 3 Days at 60° C. | D50 [µm] 7 Days at 60° C. | 1.3µ↑ [%] Initial Sample | 1.3µ↑ [%] 3 Days at 60° C. | 1.3µ↑ [%] 7 Days at 60° C. |
|---|---|---|---|---|---|---|---|---|---|
| F-1 | Potassium Chloride | 3.84 | 21.9 | 0.86 | 0.89 | 0.95 | 11 | 15 | 22 |
| F-2 | Magnesium Chloride | 4.89 | 27.9 | 0.87 | 0.89 | 0.96 | 11 | 14 | 22 |
| F-3 | Nil | 0 | 0 | 0.95 | 1.01 | 1.15 | 21 | 33 | 41 |

TABLE A20

| Sample No. | Salt | Salt Content (%) | Salt Content (part) per 100 parts of GumA | D50 [μm] Evaluation Score (Evaluation) | | | 1.3μ↑ [%] Evaluation Score (Evaluation) | | |
|---|---|---|---|---|---|---|---|---|---|
| | | | | Initial Sample | 3 Days at 60° C. | 7 Days at 60° C. | Initial Sample | 3 Days at 60° C. | 7 Days at 60° C. |
| F-1 | Potassium Chloride | 3.84 | 21.9 | 5 | 5 (◎) | 4 (○) | 4 | 4 (◎) | 3 (○) |
| F-2 | Magnesium Chloride | 4.89 | 27.9 | 5 | 5 (◎) | 4 (○) | 4 | 4 (◎) | 3 (○) |
| F-3 | Nil | 0 | 0 | 4 | 3 (○) | 3 (○) | 3 | 3 (◎) | 2 (○) |

TABLE A21

| Sample No. | Salt | Salt Content (%) | Salt Content (part) per 100 parts of GumA | 0 Minutes | | 3 Minutes | | 6 Minutes | |
|---|---|---|---|---|---|---|---|---|---|
| | | | | D50 | 1.3μ↑ | D50 | 1.3μ↑ | D50 | 1.3μ↑ |
| F-1 | Potassium Chloride | 3.84 | 21.9 | 0.86 | 11 | 0.99 | 31 | 1.06 | 38 |
| F-2 | Magnesium Chloride | 4.89 | 27.9 | 0.88 | 12 | 0.94 | 24 | 1.01 | 32 |
| F-3 | Nil | 0 | 0 | 1.01 | 29 | 2.01 | 78 | 2.25 | 88 |

As shown in Tables A19 to A21 and FIG. 7, the emulsion stability of the emulsion composition was improved by adding a predetermined amount of salt also when potassium chloride and magnesium chloride were used.

Test Example G: pH

Preparation of Emulsion Composition

An emulsion composition was prepared according to the formulation shown in Table A22.

An emulsion stability test was performed using the prepared emulsion composition.

Figure 8:
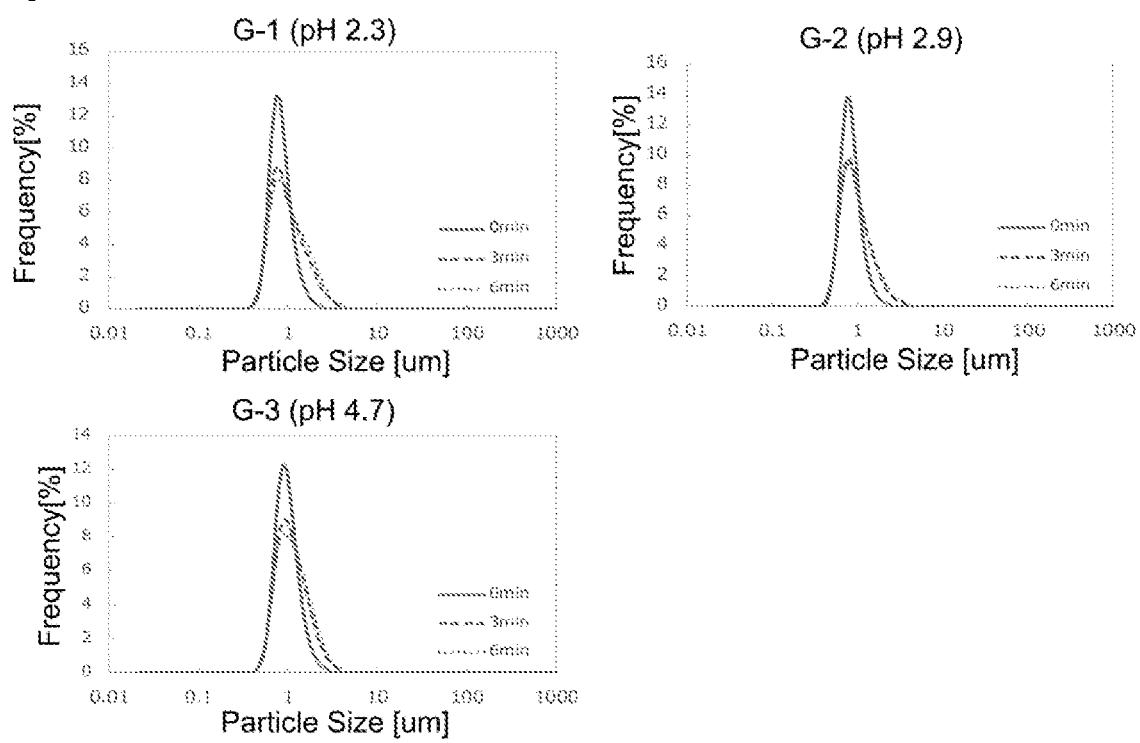
FIG. 8: Results (particle size distribution) of the emulsion physical stability test for samples G-1 to G-3 in Test Example G.

The results for emulsifiability and emulsion storage stability are shown in Tables A23 and A24. The results of emulsion physical stability test are shown in Table A25 and FIG. 8.

TABLE A22

| Formulation Mass % | G-1 | G-2 | G-3 |
|---|---|---|---|
| Medium-Chain Triglyceride | 15 | 15 | 15 |
| GumArabic(Molecular Weight: 150 × 10$^4$) | 17.5 | 17.5 | 17.5 |
| Sodium Chloride | 3.0 | 3.0 | 3.0 |
| Citric Acid (Anhydrous) | 0.5 | 0.5 | 0.5 |
| 6N Hydrochloric Acid | Adjusted to pH below | — | — |
| 6N Sodium Hydroxide | — | — | Adjusted to pH below |
| Propylene Glycol | 10 | 10 | 10 |
| Ion-Exchanged Water (added to result in 100%) | 100 | 100 | 100 |
| Sodium Chloride Content (part) per 100 parts of GumArabic | 17.1 | 17.1 | 17.1 |
| pH | 2.3 | 2.9 | 4.7 |

TABLE A23

| Sample No. | pH | Initial Sample | | | 3 Days at 60° C. | | | 7 Days at 60° C. | | |
|---|---|---|---|---|---|---|---|---|---|---|
| | | D50 | 1.3μ↑ | 0.1% E | D50 | 1.3μ↑ | 0.1% E | D50 | 1.3μ↑ | 0.1% E |
| G-1 | 2.3 | 0.76 | 6 | 0.40 | 0.81 | 11 | 0.42 | 0.90 | 21 | 0.45 |
| G-2 | 2.9 | 0.78 | 6 | 0.41 | 0.81 | 11 | 0.43 | 0.84 | 15 | 0.44 |
| G-3 | 4.7 | 0.89 | 13 | 0.48 | 0.96 | 23 | 0.49 | 1.01 | 29 | 0.50 |

TABLE A24

| Sample No. | pH | Initial Sample Evaluation Score | | 3 Days at 60° C. Evaluation Score (Evaluation) | | 7 Days at 60° C. Evaluation Score (Evaluation) | |
|---|---|---|---|---|---|---|---|
| | | D50 | 1.3μ↑ | D50 | 1.3μ↑ | D50 | 1.3μ↑ |
| G-1 | 2.3 | 5 | 5 | 5 (◎) | 4 (○) | 5 (◎) | 3 (X) |
| G-2 | 2.9 | 5 | 5 | 5 (◎) | 4 (○) | 5 (◎) | 4 (○) |
| G-3 | 4.7 | 5 | 4 | 4 (○) | 3 (○) | 3 (X) | 3 (○) |

TABLE A25

| Sample No. | pH | 0 Minutes D50 | 0 Minutes 1.3μ↑ | 3 Minutes D50 | 3 Minutes 1.3μ↑ | 6 Minutes D50 | 6 Minutes 1.3μ↑ |
|---|---|---|---|---|---|---|---|
| G-1 | 2.3 | 0.77 | 7 | 0.88 | 24 | 0.93 | 29 |
| G-2 | 2.9 | 0.78 | 6 | 0.86 | 20 | 0.87 | 22 |
| G-3 | 4.7 | 0.91 | 15 | 1.01 | 30 | 1.04 | 34 |

Test Example H: Antiseptic Effects

Preparation of Emulsion Composition

An emulsion composition was prepared according to the formulation shown in Table A26.

Figure 9:
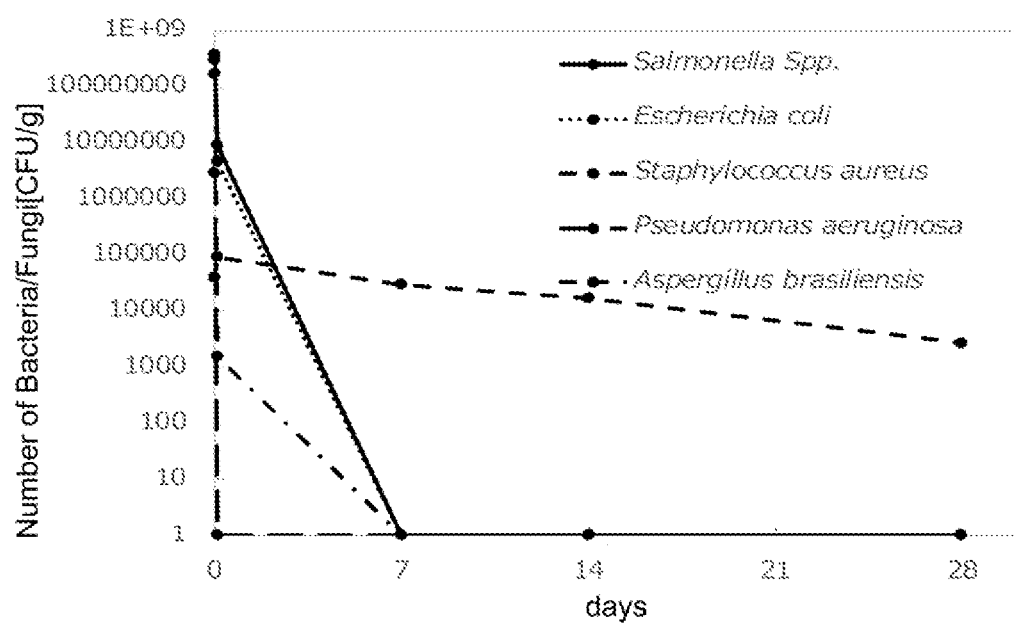
FIG. 9: Results of the measurement of the number of bacteria/fungi in the initial sample, and the samples on Day 7, Day 14, and Day 28 in Test Example H.
Figure 10:
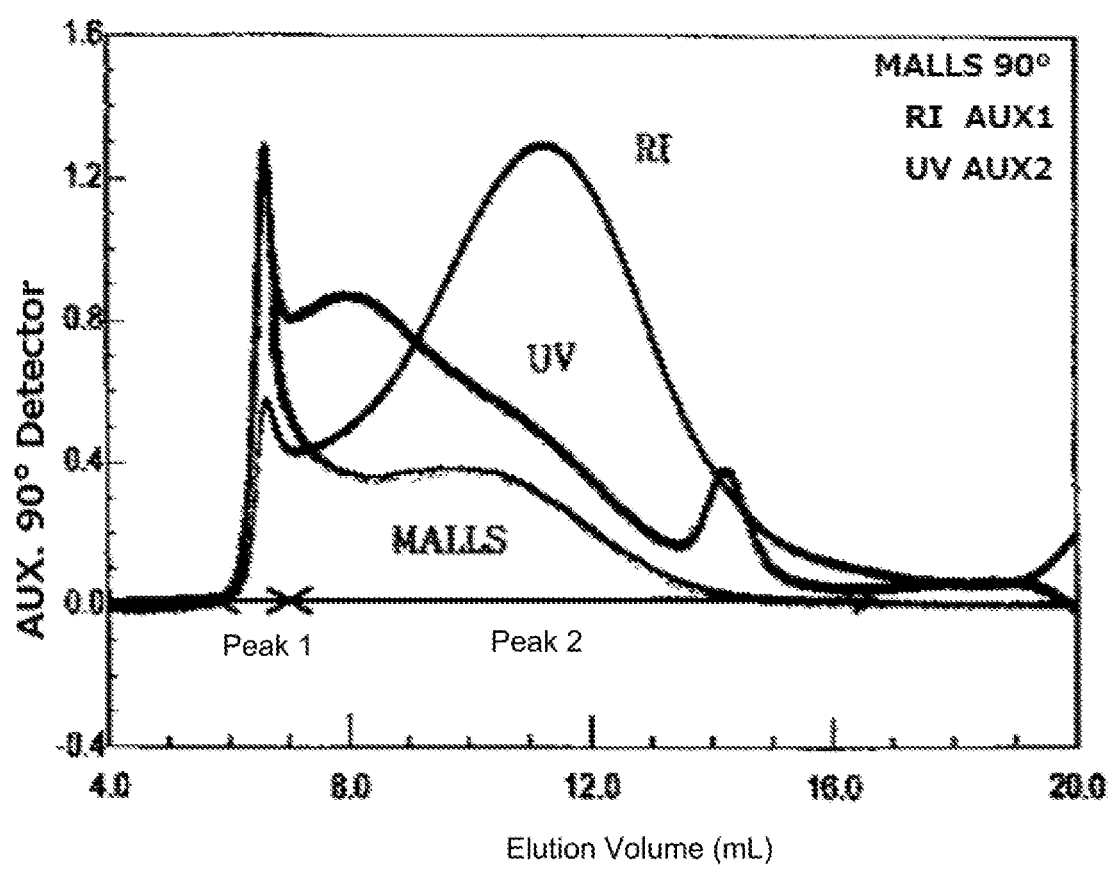
FIG. 10: A chromatogram showing results of analysis of unmodified gum arabic (*Acacia senegal*) by a GPC-MALLS method.

The antiseptic effects of the prepared emulsion composition were examined according to the following method. FIG. 9 shows the results.

Antiseptic Effects Test

The antiseptic effects of the emulsion composition were examined according to the method of the 17th revised (the latest) preservative effectiveness test of the Japanese Pharmacopoeia (US Pharmacopeia USO39 (2016)).

Procedures

Test bacteria or fungi were inoculated in a sample (emulsion composition) and the sample was stored at 25° C. The number of bacteria or fungi was measured in the initial sample, and in the samples of Day 7, Day 14, and Day 28.

Test Bacteria and Fungi

*Escherichia Coli*
Pseudomonas Aeruginosa
Staphylococcus Aureus
Yeast: *Candida Albicans*
*Aspergillus Brasiliensis*

TABLE A26

| Formulation Mass % | H-1 |
|---|---|
| Medium-Chain Triglyceride | 10 |
| GumArabic (Molecular Weight: 150 × 10⁴) | 18 |
| Sodium Chloride | 3.5 |
| Phosphoric Acid | 0.2 |
| Propylene Glycol | 10 |
| Ion-Exchanged Water (added to result in 100%) | 100 |
| pH | 3.3 |

As shown in FIG. 9, large reduction in the number of bacteria/fungi was confirmed in emulsion composition H-1 as a result of the antiseptic effects test in accordance with the Japanese Pharmacopoeia. It was thus revealed that emulsion composition H-1 is significantly superior in antiseptic effects.

The results revealed that the present invention provides an emulsion composition having excellent antiseptic effects without using a preservative such as sodium benzoate.

An Example of embodiment B of the present invention is shown below.

Materials

Unmodified gum arabic: Gum arabic having different molecular weights (molecular weight of 0.80 million, 1.10 million, 1.50 million, and 4.00 million) was prepared. The molecular weights were calculated by the GPC-MALLS method described in this specification. This gum arabic may hereinafter be referred to as "GumA."

Medium-chain triglyceride (ODO): Caprylic acid/capric acid=3/1, produced by Nisshin OilliO Group, Ltd.

The following abbreviations may be used in this specification.

Decaglycerin fatty acid ester: DGFE
Propylene glycol: PG
Sodium chloride: NaCl
Unmeasurable: ND
Emulsion Stability Test
Evaluation of Emulsifiability The prepared emulsion composition (drink model) was evaluated in terms of the following items.

D50 μm or a particle size D50: median diameter 0.1.3 μm↑ (or 1.3μ↑): Frequency of a particle size of 1.3 μm or more 0.1% E (720 nm): Turbidity of a 0.1% aqueous diluent of a sample (emulsion composition) at 720 nm "D50 μm" and "1.3 μm↑" were found by measuring the particle size distribution of the emulsion composition under the following conditions.

Conditions

Particle-Size Distribution Analyzer: Microtrac MT3000EX-II (MicrotracBEL Corp.)

Measurement Method: Refraction Index=1.81, Measurement Range=0.021 to 2000 μm, Volumetric Basis "0.1% E (720 nm)" was found by using a 0.1% aqueous solution of each sample (emulsion composition), which was obtained by diluting the sample with ion-exchanged water, and measuring the turbidity of the diluent at 720 nm under the following conditions.

Conditions

Spectrophotometer: V-660DS spectrophotometer, produced by JASCO Corporation

Measurement Conditions: Quartz cell, 10 mm×10 mm, Absorbance (Abs)

Evaluation of Emulsion Storage Stability

The prepared emulsion composition (drink model) was placed in a 30-mL glass bottle to fill and stored in a constant-temperature bath at 60° C. The evaluation was performed in terms of the following items using the emulsion composition three days and seven days after the storage.

Evaluation Items

D50 μm or a particle size D50: median diameter
The unit in the tables is μm.

1.3 μm↑ (or 1.3 u<): Frequency of a particle size of 1.3 μm or more

The numbers in the tables denote proportions based on the number of all particles (unit: %).

0.1% E (720 nm): Turbidity of a 0.1% aqueous diluent of a sample (emulsion composition) at 720 nm The preferable range of turbidity as a clouding agent is 0.2 or more. The upper limit is preferably, but not particularly limited to, for example, not more than 1, preferably not more than 0.8.

Evaluation of Emulsion Physical Stability

Figure 11:
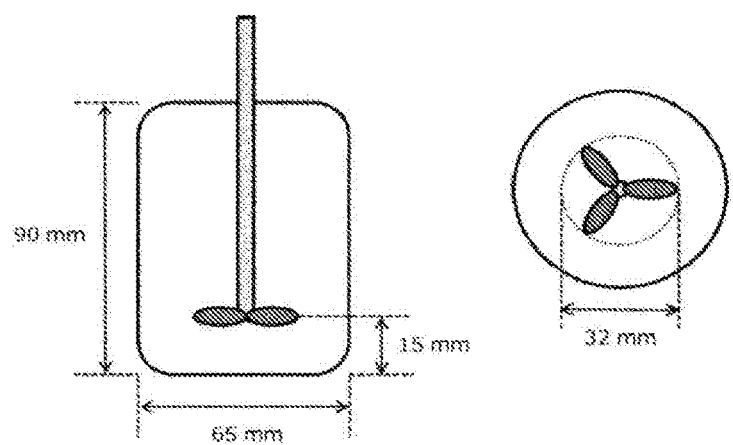
FIG. 11: A schematic diagram showing a test for evaluating emulsion physical stability (accelerated test). The figure on the left is a lateral view and the figure on the right is an upper view of the test system.

An accelerated test was performed to evaluate, as one of the indices of emulsion physical stability, changes of emulsified particles when the emulsion composition (drink model) was stirred under a high temperature condition. FIG. 11 shows a schematic diagram.

Instruments: 200-mL beaker (glass beaker, diameter=65 mm, height=90 mm)

Stirring blade (a metal rod having a diameter of 5 mm with three blades having a diameter of 32 mm on its top end)

Measurement Method:

1) 200 g of a sample (emulsion composition) is weighed and placed in a 200-mL beaker.

2) The sample is allowed to stand at 60° C. for 20 minutes.

3) A blade is placed in a portion 15 mm high from the bottom of the 200-mL beaker.
4) The sample is stirred with the stirring blade at a rotation rate of 1300 rpm.
5) The emulsion composition is sampled for a predetermined time (0 minutes, 3 minutes, and 6 minutes).

The particle size distribution is measured under the following measurement conditions.

Measurement Conditions:
Particle-Size Distribution Analyzer: Microtrac MT3000EX-II (MicrotracBEL Corp.)
Measurement Method: Refraction Index=1.81, Measurement Range=0.021 to 2000 μm, Volumetric Basis
Evaluation of Emulsion Stability Tables B1 and B2 below show evaluation criteria in the evaluation of emulsion stability in each Example.

"Evaluation (changes over time)" was performed using a difference (score difference) between an "emulsion state (evaluation score)" immediately after the preparation (initial sample) of an emulsion composition (drink model) and an emulsion state (evaluation score) of the emulsion composition at the time of evaluation (after the test of the emulsion storage stability or after the test of the emulsion physical stability) as an index.

The "evaluation (changes over time)" was performed by grading samples having an initial sample evaluation score of 3 or more (better than normal) in 4 levels, i.e., A, B, C and D (A being the best), according to Table B2. The samples having an initial sample evaluation score of less than 3 were regarded as originally having a poor emulsion state, and the evaluation over time was not performed for these samples (shown as "–" in the tables).

TABLE B1

| Evaluation Score (Emulsion State) | D50 μm | 1.3 μm↑ (1.3 u<) |
|---|---|---|
| 5: Excellent | Not more than 0.9 μm | Not more than 10% |
| 4: Very Good | More than 0.9 μm to not more than 1.0 μm | More than 10% to not more than 20% |
| 3: Good | More than 1.0 μm to not more than 1.2 μm | More than 20% to not more than 35% |
| 2: Bad | More than 1.2 μm to not more than 2.0 μm | More than 35% to not more than 50% |
| 1: Very Bad | More than 2.0 μm— | More than 50%— |

TABLE B2

| Evaluation (Changes Over Time) | Difference (Variation) in Evaluation Score (Emulsion State) |
|---|---|
| A: Very Stable | 0 |
| B: Stable | −1 |
| C: Relatively Unstable | −2 |
| D: Unstable | −3 or less |
| — | A score of less than 3 for Initial Sample |

Method for Producing Emulsion Composition (Drink Model)

The emulsion compositions (drink model) were produced according to the formulations in the tables. The materials shown in the formulations were stirred at 3000 rpm for 5 minutes, thereby preparing a mixed liquid. Subsequently, the mixed liquid was homogenized with a high-pressure homogenizer (15MR-8TA homogenizer, produced by Manton-Gaulin Co., Ltd.) (350 kg/cm$^2$, 5 times), thereby producing an emulsion composition.

Test Example A: Gum Arabic Molecular Weight

Preparation of Emulsion Composition (Drink Model)

Emulsion compositions (drink model) A-1 to A-12 were prepared according to the formulation in Table B3.

An emulsion stability test was performed using the prepared emulsion composition.

Figure 12:
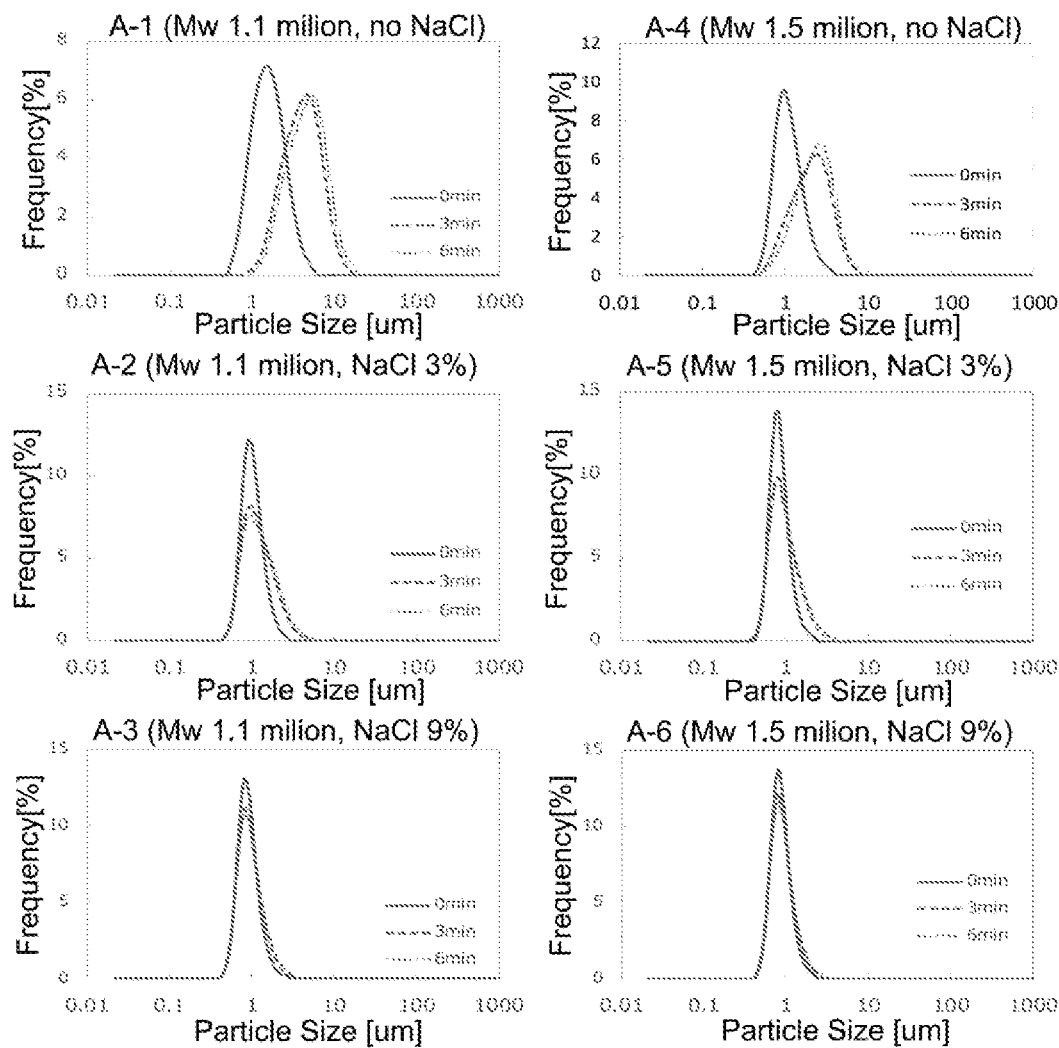
FIG. 12: Results (particle size distribution) of the emulsion physical stability test for samples A-1 to A-6 in Test Example A.
Figure 13:
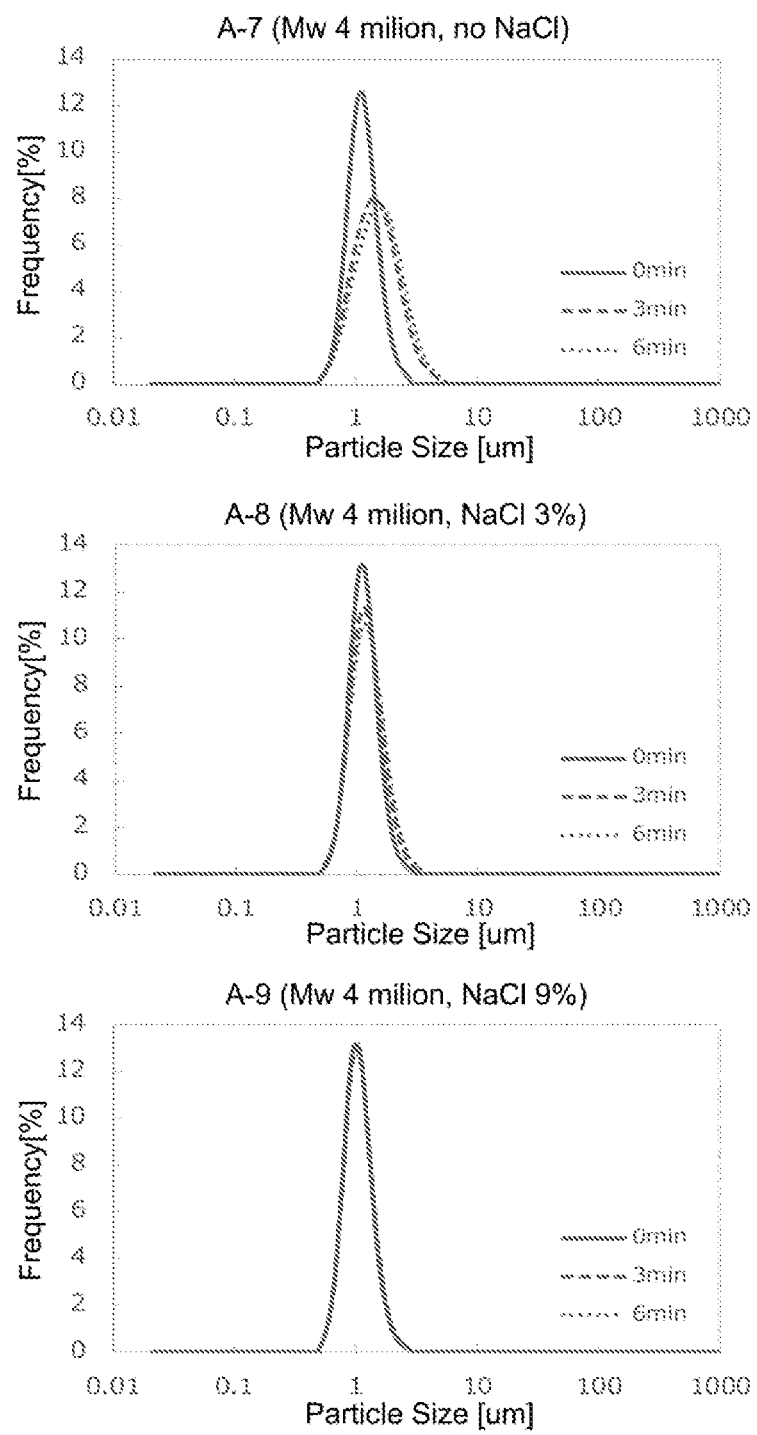
FIG. 13: Results (particle size distribution) of the emulsion physical stability test for samples A-7 to A-9 in Test Example A.

The test results for emulsifiability and emulsion storage stability are shown in Tables B4 and B5, and the results of the emulsion physical stability test are shown in Table B6 and FIGS. 12 and 13.

The pH of the emulsion compositions A-1 to A-12 was within the range of 2.5 to 3.5.

TABLE B3

| (Emulsion Compositions A-1 to A-12) Formulation | Mass % |
|---|---|
| Medium-Chain Triglyceride | 15 |
| GumA (Molecular Weight: see Tables B4 to 6) | 17.5 |
| Sodium Chloride | See Tables B4 to Table B6 |
| Citric Acid (Anhydrous) | 0.5 |
| Propylene Glycol | 10 |
| Ion-Exchanged Water (added to result in 100%) | 100 |

TABLE B4

| Sample No. | GumA Molecular Weight (Million) | NaCl (%) | Initial Sample | | | 3 Days at 60° C. | | | 7 Days at 60° C. | | |
|---|---|---|---|---|---|---|---|---|---|---|---|
| | | | D50 | 1.3 u< [%] | 0.1% E | D50 | 1.3 u< [%] | 0.1% E | D50 | 1.3 u< [%] | 0.1% E |
| A-1 | 1.10 | 0 | 1.20 | 44 | 0.54 | 1.47 | 65 | 0.59 | 1.63 | 75 | 0.60 |
| A-2 | 1.10 | 3 | 0.92 | 16 | 0.49 | 0.97 | 22 | 0.51 | 1.05 | 31 | 0.51 |
| A-3 | 1.10 | 9 | 0.84 | 9 | 0.44 | 0.83 | 9 | 0.45 | 0.87 | 14 | 0.45 |
| A-4 | 1.50 | 0 | 0.95 | 21 | 0.48 | 1.07 | 33 | 0.50 | 1.15 | 41 | 0.52 |
| A-5 | 1.50 | 3 | 0.78 | 6 | 0.41 | 0.81 | 11 | 0.43 | 0.84 | 15 | 0.44 |
| A-6 | 1.50 | 9 | 0.80 | 8 | 0.42 | 0.82 | 8 | 0.42 | 0.82 | 10 | 0.42 |
| A-7 | 4.00 | 0 | 1.08 | 29 | 0.56 | 1.13 | 36 | 0.58 | 1.21 | 45 | 0.58 |
| A-8 | 4.00 | 3 | 1.07 | 27 | 0.59 | 1.10 | 32 | 0.59 | 1.15 | 39 | 0.59 |
| A-9 | 4.00 | 9 | 1.01 | 21 | 0.55 | 1.01 | 27 | 0.54 | 1.00 | 21 | 0.54 |
| A-10 | 0.80 | 0 | 2.48 | 87 | 0.55 | 2.40 | 94 | 0.62 | 2.46 | 96 | 0.65 |
| A-11 | 0.80 | 3 | 0.95 | 25 | 0.48 | 1.12 | 39 | 0.52 | 1.18 | 42 | 0.54 |
| A-12 | 0.80 | 9 | 0.91 | 16 | 0.47 | 0.94 | 18 | 0.49 | 0.98 | 22 | 0.50 |

TABLE B5

| Sample No. | GumA Molecular Weight (Million) | NaCl (%) | Initial Sample Evaluation Score D50 | Initial Sample Evaluation Score 1.3 u< [%] | 3 Days at 60° C. Evaluation Score (Evaluation) D50 | 3 Days at 60° C. Evaluation Score (Evaluation) 1.3 u< [%] | 7 Days at 60° C. Evaluation Score (Evaluation) D50 | 7 Days at 60° C. Evaluation Score (Evaluation) 1.3 u< [%] |
|---|---|---|---|---|---|---|---|---|
| A-1 | 1.10 | 0 | 3 | 2 | 2 (B) | 1 (—) | 2 (B) | 1 (—) |
| A-2 | 1.10 | 3 | 4 | 4 | 4 (A) | 3 (B) | 3 (B) | 3 (B) |
| A-3 | 1.10 | 9 | 5 | 5 | 5 (A) | 5 (A) | 5 (A) | 4 (B) |
| A-4 | 1.50 | 0 | 4 | 3 | 3 (B) | 3 (A) | 3 (B) | 2 (B) |
| A-5 | 1.50 | 3 | 5 | 5 | 5 (A) | 4 (B) | 5 (A) | 4 (B) |
| A-6 | 1.50 | 9 | 5 | 5 | 5 (A) | 5 (A) | 5 (A) | 5 (A) |
| A-7 | 4.00 | 0 | 3 | 3 | 3 (A) | 2 (B) | 2 (B) | 2 (B) |
| A-8 | 4.00 | 3 | 3 | 3 | 3 (A) | 3 (A) | 3 (A) | 2 (B) |
| A-9 | 4.00 | 9 | 3 | 3 | 3 (A) | 3 (A) | 4 (A) | 3 (A) |
| A-10 | 0.80 | 0 | 1 | 1 | 1 (—) | 1 (—) | 1 (—) | 1 (—) |
| A-11 | 0.80 | 3 | 4 | 3 | 3 (B) | 2 (B) | 3 (B) | 2 (B) |
| A-12 | 0.80 | 9 | 4 | 4 | 4 (A) | 4 (A) | 4 (A) | 3 (B) |

TABLE B6

| Sample No. | GumA Molecular Weight (Million) | NaCl (%) | Initial Sample (0 Minutes) D50 | Initial Sample (0 Minutes) 1.3 u< [%] | 3 Minutes D50 | 3 Minutes 1.3 u< [%] | 6 Minutes D50 | 6 Minutes 1.3 u< [%] |
|---|---|---|---|---|---|---|---|---|
| A-1 | 1.10 | 0 | 1.46 | 62 | 3.89 | 98 | 4.44 | 99 |
| A-2 | 1.10 | 3 | 0.92 | 16 | 1.05 | 35 | 1.10 | 40 |
| A-3 | 1.10 | 9 | 0.84 | 10 | 0.87 | 10 | 0.88 | 18 |
| A-4 | 1.50 | 0 | 1.01 | 29 | 2.01 | 78 | 2.25 | 88 |
| A-5 | 1.50 | 3 | 0.78 | 6 | 0.86 | 20 | 0.87 | 22 |
| A-6 | 1.50 | 9 | 0.81 | 8 | 0.83 | 11 | 0.84 | 14 |
| A-7 | 4.00 | 0 | 1.10 | 30 | 1.39 | 59 | 1.50 | 65 |
| A-8 | 4.00 | 3 | 1.07 | 27 | 1.13 | 36 | 1.15 | 39 |
| A-9 | 4.00 | 9 | 1.01 | 20 | 1.01 | 22 | 1.01 | 22 |

Tables B4 and B5 confirmed that the emulsion stability of emulsion compositions using gum arabic and a specific amount of sodium chloride was superior to that of an emulsion composition that does not contain sodium chloride. Regarding the emulsifiability, the particle size tends to decrease by having sodium chloride added. Regarding the emulsion storage stability, the variation in emulsified particles (D50, 1.3 μm↑) tends to decrease compared with the sample with no addition of sodium chloride.

The emulsion stability thereof had a tendency to increase along with an increase in the molecular weight of gum arabic.

Table B6 and FIGS. 12 and 13 show the results of the emulsion physical stability test. It was confirmed that the particle size distribution of the emulsion compositions using gum arabic having molecular weights of 1.10 million, 1.50 million, and 4.00 million, and a specific amount of sodium chloride after the accelerated test (3 and 6 minutes after the test) did not greatly vary. This indicated that the sample was superior in emulsion physical stability.

Test Example B: Consideration of Salt Content (1)

Preparation of Emulsion Composition

Emulsion compositions B-1 to B-11 were prepared according to the formulation shown in Table B7.

An emulsion stability test was performed using the prepared emulsion composition.

Figure 14:
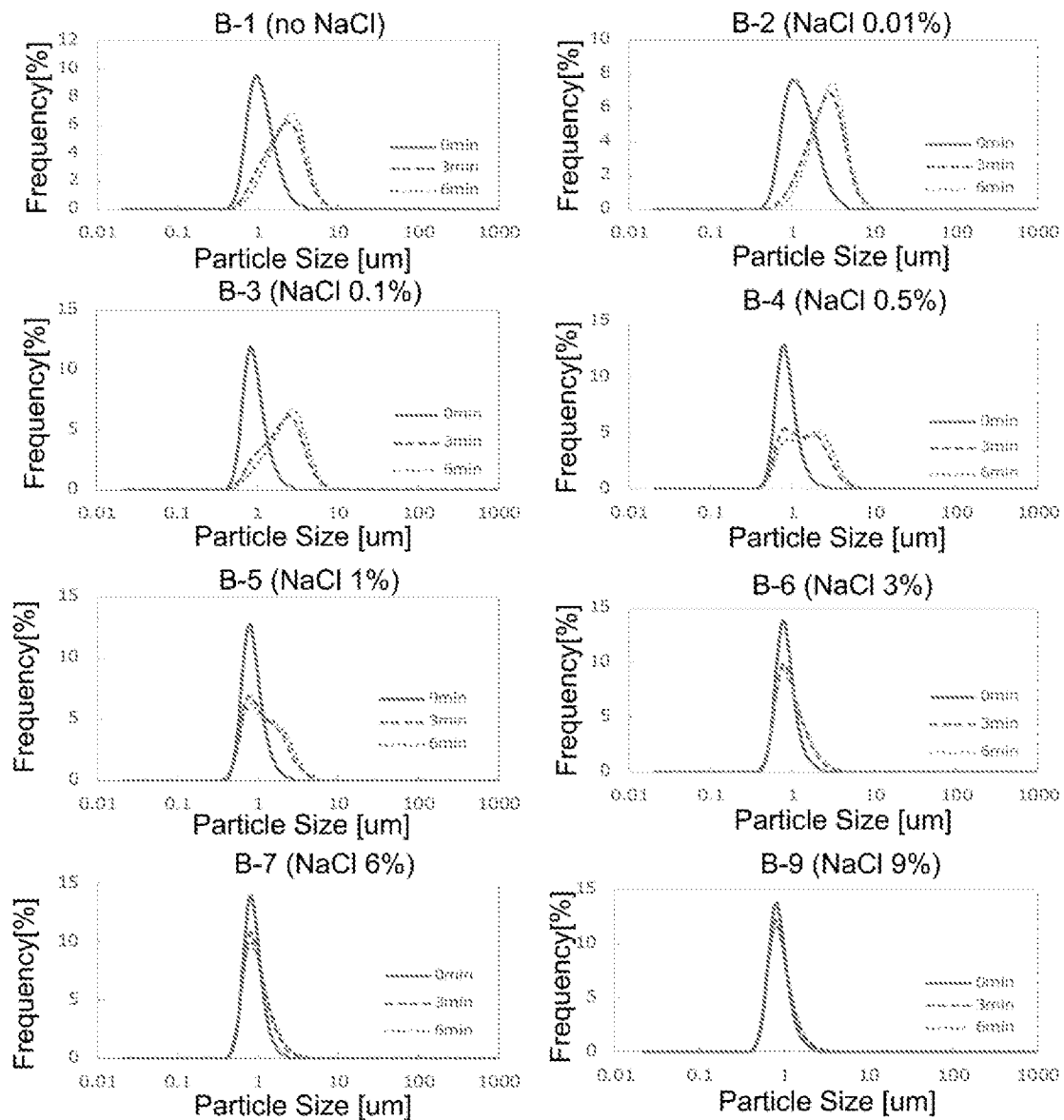
FIG. 14: Results (particle size distribution) of the emulsion physical stability test for samples B-1 to B-7 and B-9 in Test Example B.

The test results for emulsifiability and emulsion storage stability are shown in Tables B8 and B9, and the results of the emulsion physical stability test are shown in Table B10 and FIG. 14.

The pH of the emulsion compositions B-1 to B-11 was within the range of 2.5 to 3.5.

TABLE B7

(Emulsion Compositions B-1 to B-11)

| Formulation | Mass % |
|---|---|
| Medium-Chain Triglyceride | 15 |
| GumArabic (Molecular Weight: 1.50 million) | 17.5 |
| Sodium Chloride | See Tables B8 to Table B10 |
| Citric Acid (Anhydrous) | 0.5 |
| Propylene Glycol | 10 |
| Ion-Exchanged Water (added to result in 100%) | 100 |

TABLE B8

| Sample No. | Salt Content NaCl (%) | (part) per 100 parts of GumA | D50 [μm] Initial Sample | D50 [μm] 3 Days at 60° C. | D50 [μm] 7 Days at 60° C. | 1.3 u< [%] Initial Sample | 1.3 u< [%] 3 Days at 60° C. | 1.3 u< [%] 7 Days at 60° C. |
|---|---|---|---|---|---|---|---|---|
| B-1 | 0 | 0 | 0.95 | 1.07 | 1.15 | 21 | 33 | 41 |
| B-2 | 0.01 | 0.06 | 0.97 | 1.01 | 1.18 | 23 | 35 | 43 |
| B-3 | 0.1 | 0.6 | 0.83 | 0.95 | 1.07 | 10 | 25 | 37 |
| B-4 | 0.5 | 2.9 | 0.77 | 0.87 | 0.95 | 7 | 16 | 28 |
| B-5 | 1 | 5.7 | 0.78 | 0.85 | 0.91 | 7 | 16 | 22 |
| B-6 | 3 | 17.1 | 0.78 | 0.81 | 0.84 | 6 | 11 | 15 |
| B-7 | 6 | 34.2 | 0.81 | 0.83 | 0.86 | 7 | 9 | 14 |
| B-8 | 8 | 45.7 | 0.84 | 0.86 | 0.87 | 9 | 10 | 12 |
| B-9 | 9 | 51.4 | 0.80 | 0.82 | 0.82 | 8 | 8 | 10 |

TABLE B9

| Sample No. | Salt Content NaCl (%) | (part) per 100 parts of GumA | D50 [μm] Evaluation Score (Evaluation) Initial Sample | D50 [μm] Evaluation Score (Evaluation) 3 Days at 60° C. | D50 [μm] Evaluation Score (Evaluation) 7 Days at 60° C. | 1.3 u< [%] Evaluation Score (Evaluation) Initial Sample | 1.3 u< [%] Evaluation Score (Evaluation) 3 Days at 60° C. | 1.3 u< [%] Evaluation Score (Evaluation) 7 Days at 60° C. |
|---|---|---|---|---|---|---|---|---|
| B-1 | 0 | 0 | 4 | 3 (B) | 3(B) | 3 | 3 (A) | 2 (B) |
| B-2 | 0.01 | 0.06 | 4 | 3 (B) | 3 (B) | 3 | 3 (A) | 2 (B) |
| B-3 | 0.1 | 0.6 | 5 | 4 (B) | 3 (C) | 5 | 3 (C) | 2 (D) |
| B-4 | 0.5 | 2.9 | 5 | 5 (A) | 4(B) | 5 | 4 (B) | 3 (C) |
| B-5 | 1 | 5.7 | 5 | 5 (A) | 4(B) | 5 | 4 (B) | 3 (C) |
| B-6 | 3 | 17.1 | 5 | 5 (A) | 5(A) | 5 | 4 (B) | 4 (B) |
| B-7 | 6 | 34.2 | 5 | 5 (A) | 5(A) | 5 | 5 (A) | 4 (B) |
| B-8 | 8 | 45.7 | 5 | 5 (A) | 5(A) | 5 | 5 (A) | 4 (B) |
| B-9 | 9 | 51.4 | 5 | 5 (A) | 5(A) | 5 | 5 (A) | 5 (A) |

The results shown in Tables B8 and B9 confirmed that the emulsifiability and emulsion storage stability of the emulsion composition were improved by adding a predetermined amount of sodium chloride.

An emulsion composition was prepared using the same method as that for the emulsion composition described above, except that the sodium chloride content was changed to 12 mass % (sample B-10). However, in this emulsion composition, precipitation of sodium chloride was partially observed.

TABLE B10

| Sample No. | Salt Content NaCl (%) | (part) per 100 parts of GumA | 0 Minutes D50 | 0 Minutes 1.3 u< [%] | 3 Minutes D50 | 3 Minutes 1.3 u< [%] | 6 Minutes D50 | 6 Minutes 1.3 u< [%] |
|---|---|---|---|---|---|---|---|---|
| B-1 | 0 | 0 | 1.01 | 29 | 2.01 | 78 | 2.25 | 85 |
| B-2 | 0.01 | 0.06 | 1.15 | 42 | 2.47 | 88 | 2.71 | 93 |
| B-3 | 0.1 | 0.6 | 0.84 | 12 | 1.95 | 74 | 2.28 | 83 |
| B-4 | 0.5 | 2.9 | 0.80 | 9 | 1.27 | 50 | 1.51 | 59 |
| B-5 | 1 | 5.7 | 0.80 | 9 | 1.04 | 38 | 1.14 | 44 |
| B-6 | 3 | 17.1 | 0.78 | 6 | 0.86 | 20 | 0.87 | 22 |
| B-7 | 6 | 34.2 | 0.82 | 7 | 0.87 | 17 | 0.88 | 20 |
| B-9 | 9 | 51.4 | 0.81 | 8 | 0.83 | 11 | 0.84 | 14 |

Table B10 and FIG. 14 show the results of the emulsion physical stability test for samples B-1 to B-7, and B-9. It was confirmed that when the sodium chloride content was 3 mass % or more, the emulsion physical stability was significantly improved.

Test Example C: Consideration of Salt Content (2)

Preparation of Emulsion Composition

Emulsion compositions C-1 to C-4 were prepared according to the formulation shown in Table B11.

An emulsion stability test was performed using the prepared emulsion composition.

The test results for emulsifiability and emulsion storage stability are shown in Tables B12 and B13.

The pH of emulsion compositions C-1 to C-4 was within the range of 2.5 to 3.5.

TABLE B11

| (Emulsion Compositions C-1 to C-4) Formulation | Mass % |
|---|---|
| Medium-Chain Triglyceride | 15 |
| GumArabic (Molecular Weight: 1.50 million) | 17.5 |
| Sodium Chloride | See Tables B12 to Table B13 |
| Citric Acid (Anhydrous) | 0.5 |
| Glycerin | 20 |
| Ion-Exchanged Water (added to result in 100%) | 100 |

TABLE B12

| | | | D50 [μm] | | | 1.3 u< [%] | | |
|---|---|---|---|---|---|---|---|---|
| Sample No. | NaCl (%) | Salt Content (part) per 100 parts of GumA | Initial Sample | 3 Days at 60° C. | 7 Days at 60° C. | Initial Sample | 3 Days at 60° C. | 7 Days at 60° C. |
| C-1 | 0.1 | 0.6 | 0.72 | 0.76 | 0.80 | 5 | 11 | 18 |
| C-2 | 3 | 17.1 | 0.65 | 0.66 | 0.66 | 3 | 4 | 4 |
| C-3 | 8 | 45.7 | 0.56 | 0.56 | 0.56 | 2 | 2 | 2 |
| C-4 | 11.5 | 65.7 | 0.50 | 0.51 | 0.51 | 1 | 1 | 1 |

TABLE B13

| | | | D50 [μm] Evaluation Score (Evaluation) | | | 1.3 u< [%] Evaluation Score (Evaluation) | | |
|---|---|---|---|---|---|---|---|---|
| Sample No. | NaCl (%) | Salt Content (part) per 100 parts of GumA | Initial Sample | 3 Days at 60° C. | 7 Days at 60° C. | Initial Sample | 3 Days at 60° C. | 7 Days at 60° C. |
| C-1 | 0.1 | 0.6 | 5 | 5 (A) | 5 (A) | 5 | 4 (B) | 4(B) |
| C-2 | 3 | 17.1 | 5 | 5 (A) | 5 (A) | 5 | 5 (A) | 5 (A) |
| C-3 | 8 | 45.7 | 5 | 5 (A) | 5 (A) | 5 | 5 (A) | 5 (A) |
| C-4 | 11.5 | 65.7 | 5 | 5 (A) | 5 (A) | 5 | 5 (A) | 5 (A) |

Tables B12 and B13 revealed that the emulsifiability and emulsion storage stability of the emulsion composition were improved by adding sodium chloride.

Test Example D: Consideration of Emulsifier Other than Gum Arabic

Preparation of Emulsion Composition

Emulsion compositions D-1 to D-6 were prepared according to the formulation shown in Table B14. An emulsion stability test was performed using the prepared emulsion composition.

The test results for emulsifiability and emulsion storage stability are shown in Tables B15 and B16.

TABLE B14

| | (Emulsion Compositions D-1 to D-6) Formulation | | | | | |
|---|---|---|---|---|---|---|
| | D-1 Mass % | D-2 Mass % | D-3 Mass % | D-4 Mass % | D-5 Mass % | D-6 Mass % |
| Medium-Chain Triglyceride | 15 | 15 | 15 | 15 | 15 | 15 |
| GumArabic (Molecular Weight: 1.50 million) | 17.5 | 17.5 | 17.5 | 17.5 | — | — |

TABLE B14-continued (Emulsion Compositions D-1 to D-6)
Formulation

| | D-1 Mass % | D-2 Mass % | D-3 Mass % | D-4 Mass % | D-5 Mass % | D-6 Mass % |
|---|---|---|---|---|---|---|
| Decaglycerin Fatty Acid Ester | — | — | — | — | 17.5 | 17.5 |
| Sodium Chloride | — | 8 | — | 8 | — | 8 |
| Propylene Glycol | — | — | 10 | 10 | — | — |
| Ion-Exchanged Water (added to result in 100%) | 100 | 100 | 100 | 100 | 100 | 100 |

TABLE B15

| | | | | Salt Content (part) per 100 parts of Emulsifier | D50 [μm] | | | 1.3 u< [%] | | |
|---|---|---|---|---|---|---|---|---|---|---|
| Sample No. | Emulsifier | PG (%) | NaCl (%) | | Initial Sample | 3 Days at 60° C. | 7 Days at 60° C. | Initial Sample | 3 Days at 60° C. | 7 Days at 60° C. |
| D-1 | GumA | 0 | 0 | 0 | 0.41 | 0.51 | 0.72 | 1 | 20 | 36 |
| D-2 | GumA | 0 | 8 | 45.7 | 0.54 | 0.72 | 0.73 | 4 | 10 | 13 |
| D-3 | GumA | 10 | 0 | 0 | 0.88 | 1.11 | 1.12 | 15 | 41 | 45 |
| D-4 | GumA | 10 | 8 | 45.7 | 0.88 | 0.90 | 0.92 | 12 | 14 | 16 |
| D-5 | DGFE | 0 | 0 | 0 | 0.13 | — | — | 0 | — | — |
| D-6 | DGFE | 0 | 8 | 45.7 | 16.54 | ND | ND | 100 | ND | ND |

ND: unmeasurable

TABLE B16

| | | | | Salt Content (part) per 100 parts of Emulsifier | D50 [μm] Evaluation Score (Evaluation) | | | 1.3 u< [%] Evaluation Score (Evaluation) | | |
|---|---|---|---|---|---|---|---|---|---|---|
| Sample No. | Emulsifier | PG (%) | NaCl (%) | | Initial Sample | 3 Days at 60° C. | 7 Days at 60° C. | Initial Sample | 3 Days at 60° C. | 7 Days at 60° C. |
| D-1 | GumA | 0 | 0 | 0 | 5 | 5 (A) | 5 (A) | 5 | 3 (C) | 2 (D) |
| D-2 | GumA | 0 | 8 | 45.7 | 5 | 5 (A) | 5 (A) | 5 | 5 (A) | 4 (B) |
| D-3 | GumA | 10 | 0 | 0 | 5 | 3 (C) | 3 (C) | 4 | 2 (C) | 2 (C) |
| D-4 | GumA | 10 | 8 | 45.7 | 5 | 5 (A) | 4 (B) | 4 | 4 (A) | 4 (A) |
| D-5 | DGFE | 0 | 0 | 0 | 5 | — | — | 5 | — | — |
| D-6 | DGFE | 0 | 8 | 45.7 | 1 | ND | ND | 100 | ND | ND |

ND: unmeasurable

The results for D-1 to D-4 using gum arabic revealed that the emulsion stability (emulsifiability and emulsion storage stability) of the emulsion composition was improved by adding a predetermined amount of salt.

In emulsion composition (D-5), which contains, as an emulsifier, decaglycerin fatty acid ester, which is generally used, and which does not contain sodium chloride, the emulsified particle diameter (D50) was small, namely, 0.13 μm, and the emulsion composition did not have sufficient turbidity, which is a property required for use as a clouding agent. The turbidity (0.1% E (720 nm)) of D-5 was measured and found to be 0.095, and a 0.1% aqueous solution was transparent.

In emulsion composition (D-6), which contains decaglycerin fatty acid ester and also contains sodium chloride, a part of the oil phase was separated after the homogenization treatment, and an uniform emulsion composition could not be prepared. The particle size distribution in the emulsified portion of the emulsion composition was measured. The emulsified particle diameter (D50) was significantly large, namely, 16.54 μm.

These results revealed that addition of sodium chloride generally serves to inhibit the emulsification of an emulsion composition, as known by conventional technical standards.

D-1 and D-2 are free of propylene glycol as polyhydric alcohol. D-3 and D-4 are emulsion compositions containing propylene glycol. A comparison between D-1 and D-3 revealed that the emulsified particle diameter immediately after the preparation was 0.41 μm (no addition of propylene glycol) and 0.88 μm (with propylene glycol), and that, therefore, the addition of propylene glycol decreased the emulsifiability. It was also revealed that the emulsion storage stability (1.3 μm↑) was 1% (no addition of propylene glycol) and 15% (with propylene glycol), and that, therefore, the addition of propylene glycol also decreased emulsion storage stability.

On the other hand, it was revealed that emulsifiability and emulsion storage stability were improved by further using sodium chloride in the sample in which propylene glycol was added (D-4).

Test Example E: Consideration of Oil/Fat Content

Preparation of Emulsion Composition

An emulsion composition E-1 was prepared according to the formulation shown in Table B17.

Figure 15:
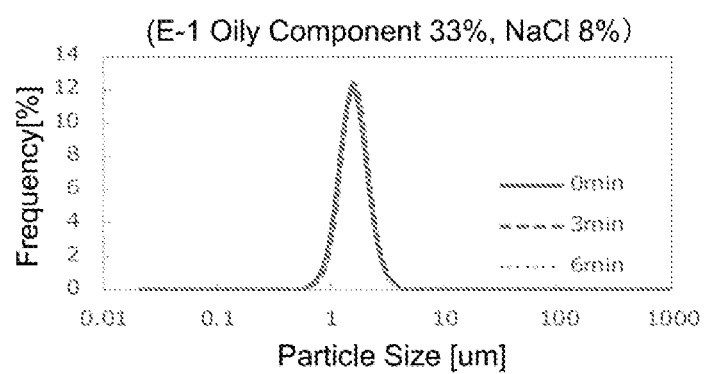
FIG. 15: Results (particle size distribution) of the emulsion physical stability test for sample E-1 in Test Example E.

An emulsion stability test (emulsion physical stability test) was performed using the prepared emulsion composition. FIG. 15 shows the results.

TABLE B17

| (Emulsion Composition E-1) Formulation | Mass % |
|---|---|
| Medium-Chain Triglyceride | 33 |
| GumArabic (Molecular Weight: 1.50 million) | 17.5 |
| Sodium Chloride | 8 |
| Ion-Exchanged Water (added to result in 100%) | 100 |
| Salt Content (part) per 100 parts of GumArabic | 45.71 |

FIG. 15 revealed that an emulsion composition having significantly superior emulsion physical stability can be prepared by incorporating gum arabic having a molecular weight of 1.50 million and a predetermined amount of sodium chloride.

Test Example F: Consideration of Types of Salt

Preparation of Emulsion Composition

Emulsion compositions F-1 to F-4 were prepared according to the formulation shown in Table B18.

An emulsion stability test was performed using the prepared emulsion composition.

Figure 16:
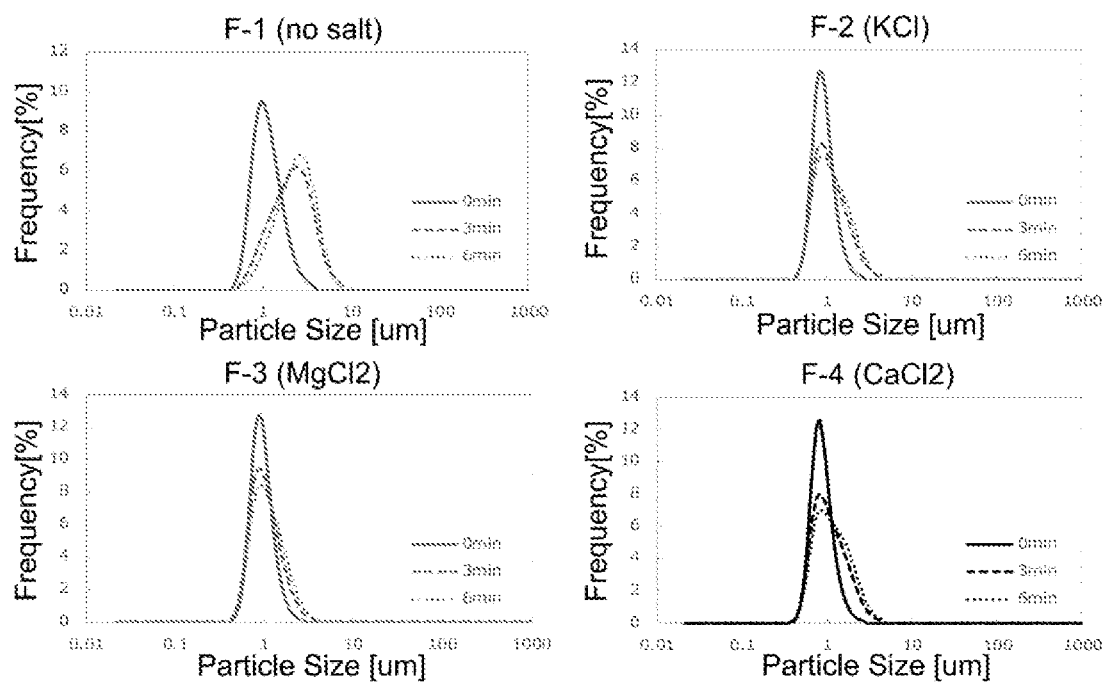
FIG. 16: Results (particle size distribution) of the emulsion physical stability test for samples F-1 to F-4 in Test Example F.

The test results for emulsifiability and emulsion storage stability are shown in Tables B19 and B20, and the results of the emulsion physical stability test are shown in Tables B21 and FIG. 16.

The pH of the emulsion compositions F-1 to F-4 was 3.3, 3.0, 2.6 and 2.5, respectively.

The turbidities (0.1% E (720 nm)) of the emulsion compositions F-1 to F-4 were within the range of 0.45 to 0.52.

TABLE B18

| (Emulsion Composition F-1 to F-3) Formulation | Mass % |
|---|---|
| Medium-Chain Triglyceride | 15 |
| GumArabic (Molecular Weight: 1.50 million) | 17.5 |
| Salt | See Tables B19 to Table B21 |
| Citric Acid (Anhydrous) | 0.5 |
| Propylene Glycol | 10 |
| Ion-Exchanged Water (added to result in 100%) | 100 |

TABLE B19

| Sample No. | Salt | Salt Content (%) | Salt Content (part) per 100 parts of GumA | D50 [μm] Initial Sample | D50 [μm] 3 Days at 60° C. | D50 [μm] 7 Days at 60° C. | 1.3 u< [%] Initial Sample | 1.3 u< [%] 3 Days at 60° C. | 1.3 u< [%] 7 Days at 60° C. |
|---|---|---|---|---|---|---|---|---|---|
| F-1 | Nil | 0 | 0 | 0.95 | 1.01 | 1.15 | 21 | 33 | 41 |
| F-2 | Potassium Chloride | 3.84 | 21.9 | 0.86 | 0.89 | 0.95 | 11 | 15 | 22 |
| F-3 | Magnesium Chloride | 4.89 | 27.9 | 0.87 | 0.89 | 0.96 | 11 | 14 | 22 |

TABLE B20

| Sample No. | Salt | Salt Content (%) | Salt Content (part) per 100 parts of GumA | D50 [μm] Evaluation Score (Evaluation) Initial Sample | D50 [μm] 3 Days at 60° C. | D50 [μm] 7 days at 60° C. | 1.3 u< [%] Evaluation Score (Evaluation) Initial Sample | 1.3 u< [%] 3 Days at 60° C. | 1.3 u< [%] 7 Days at 60° C. |
|---|---|---|---|---|---|---|---|---|---|
| F-1 | Nil | 0 | 0 | 4 | 3 (B) | 3 (B) | 3 | 3 (A) | 2 (B) |
| F-2 | Potassium Chloride | 3.84 | 21.9 | 5 | 5 (A) | 4 (B) | 4 | 4 (A) | 3 (B) |
| F-3 | Magnesium Chloride | 4.89 | 27.9 | 5 | 5 (A) | 4 (B) | 4 | 4 (A) | 3 (B) |

TABLE B21

| Sample No. | Salt | Salt Content (%) | Salt Content (part) per 100 parts of GumA | 0 Minutes D50 | 0 Minutes 1.3 u< [%] | 3 Minutes D50 | 3 Minutes 1.3 u< [%] | 6 Minutes D50 | 6 Minutes 1.3 u< [%] |
|---|---|---|---|---|---|---|---|---|---|
| F-1 | Nil | 0 | 0 | 1.01 | 29 | 2.01 | 78 | 2.25 | 88 |
| F-2 | Potassium Chloride | 3.84 | 21.9 | 0.86 | 11 | 0.99 | 31 | 1.06 | 38 |
| F-3 | Magnesium Chloride | 4.89 | 27.9 | 0.88 | 12 | 0.94 | 24 | 1.01 | 32 |

TABLE B21-continued

| Sample No. | Salt | Salt Content (%) | Salt Content (part) per 100 parts of GumA | 0 Minutes D50 | 0 Minutes 1.3 u< [%] | 3 Minutes D50 | 3 Minutes 1.3 u< [%] | 6 Minutes D50 | 6 Minutes 1.3 u< [%] |
|---|---|---|---|---|---|---|---|---|---|
| F-4 | Calcium Chloride | 5.70 | 32.6 | 0.81 | 9 | 0.96 | 30 | 1.06 | 38 |

As shown in Tables B19 to B21 and FIG. 16, the emulsion stability of the emulsion composition was improved by adding a salt also when potassium chloride and magnesium chloride were used.

As shown in Table B21 and FIG. 16, the emulsion stability of the emulsion composition was improved also when calcium chloride was used.

Test Example G: Consideration of pH

Preparation of Emulsion Composition

Emulsion compositions G-1 to G-3 were prepared according to the formulation shown in Table B22.

An emulsion stability test was performed using the prepared emulsion composition.

Figure 17:
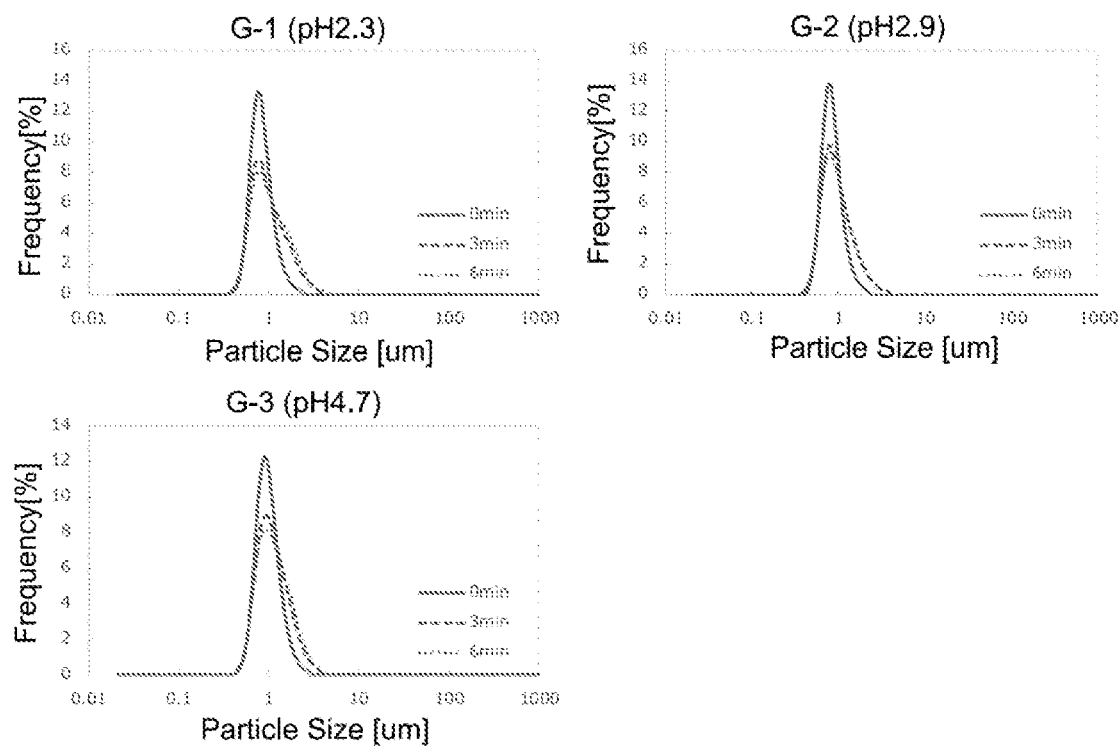
FIG. 17: Results (particle size distribution) of the emulsion physical stability test for sample G-1 to G-3 in Test Example G.

The results for emulsifiability and emulsion storage stability are shown in Tables B23 and B24. The results of the emulsion physical stability test are shown in Table B25 and FIG. 17.

TABLE B22

| (Emulsion Compositions G-1 to G-3) Formulation | G-1 Mass % | G-2 Mass % | G-3 Mass % |
|---|---|---|---|
| Medium-Chain Triglyceride | 15 | 15 | 15 |
| GumArabic (Molecular Weight: 1.50 million) | 17.5 | 17.5 | 17.5 |
| Sodium Chloride | 3.0 | 3.0 | 3.0 |
| Citric Acid (Anhydrous) | 0.5 | 0.5 | 0.5 |
| 6N Hydrochloric Acid | Adjusted to pH below | — | — |
| 6N Sodium Hydroxide | — | — | Adjusted to pH below |
| Propylene Glycol | 10 | 10 | 10 |
| Ion-Exchanged Water (added to result in 100%) | 100 | 100 | 100 |
| NaCl Content (part) per 100 parts of GumArabic | 17.1 | 17.1 | 17.1 |
| pH | 2.3 | 2.9 | 4.7 |

TABLE B23

| | | Initial Sample | | | 3 Days at 60° C. | | | 7 Days at 60° C. | | |
|---|---|---|---|---|---|---|---|---|---|---|
| Sample No. | pH | D50 | 1.3 u< [%] | 0.1% E | D50 | 1.3 u< [%] | 0.1% E | D50 | 1.3 u< [%] | 0.1% E |
| G-1 | 2.3 | 0.76 | 6 | 0.40 | 0.81 | 11 | 0.42 | 0.90 | 21 | 0.45 |
| G-2 | 2.9 | 0.78 | 6 | 0.41 | 0.81 | 11 | 0.43 | 0.84 | 15 | 0.44 |
| G-3 | 4.7 | 0.89 | 13 | 0.48 | 0.96 | 23 | 1.49 | 1.01 | 29 | 0.50 |

TABLE B24

| | | Initial Sample Evaluation Score | | 3 Days at 60° C. Evaluation Score (Evaluation) | | 7 Days at 60° C. Evaluation Score (Evaluation) | |
|---|---|---|---|---|---|---|---|
| Sample No. | pH | D50 | 1.3 u< [%] | D50 | 1.3 u< [%] | D50 | 1.3 u< [%] |
| G-1 | 2.3 | 5 | 5 | 5 (A) | 4 (B) | 5 (A) | 3 (C) |
| G-2 | 2.9 | 5 | 5 | 5 (A) | 4 (B) | 5 (A) | 4 (B) |
| G-3 | 4.7 | 5 | 4 | 4 (B) | 3 (B) | 3 (C) | 3 (B) |

TABLE B25

| | | 0 Minutes | | 3 Minutes | | 6 Minutes | |
|---|---|---|---|---|---|---|---|
| Sample No. | pH | D50 | 1.3 u< [%] | D50 | 1.3 u< [%] | D50 | 1.3 u< [%] |
| G-1 | 2.3 | 0.77 | 7 | 0.88 | 24 | 0.93 | 29 |
| G-2 | 2.9 | 0.78 | 6 | 0.86 | 20 | 0.87 | 22 |
| G-3 | 4.7 | 0.91 | 15 | 1.01 | 30 | 1.04 | 34 |

Test Example H: Antiseptic Effects Test

Preparation of Emulsion Composition

An emulsion composition H-1 was prepared according to the formulation shown in Table B26.

Figure 18:
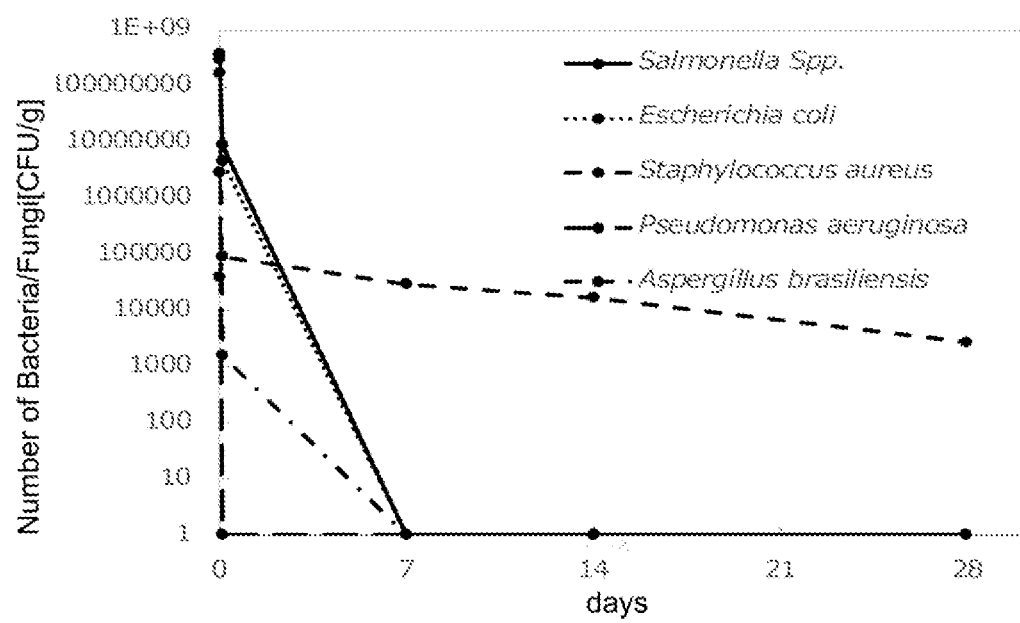
FIG. 18: Results of the measurement of the number of bacteria/fungi in the initial sample, and the samples on Day 7, Day 14, and Day 28 in Test Example H.

The antiseptic effects of the prepared emulsion composition were examined according to the following method. FIG. 18 shows the results.

Antiseptic Effects Test

The antiseptic effects of the emulsion composition were examined according to the method of the 17th revised (the latest) preservative effectiveness test of the Japanese Pharmacopoeia (US 15 Pharmacopeia USO39 (2016)).

Procedures

Test bacteria or fungi were inoculated in a sample (emulsion composition) and the sample was stored at 25° C. The number of bacteria or fungi was measured in the initial sample, and in the samples of Day 7, Day 14, and Day 28.

Test Bacteria and Fungi

*Escherichia Coli*

*Pseudomonas Aeruginosa*

*Staphylococcus Aureus*

Yeast: *Candida Albicans*
*Aspergillus Brasiliensis*

TABLE B26

| (Emulsion Composition H-1) Formulation | Mass % |
|---|---|
| Medium-Chain Triglyceride | 10 |
| GumArabic (Molecular Weight: 1.50 million) | 18 |
| NaCl | 3.5 |
| Phosphoric Acid | 0.2 |
| Propylene Glycol | 10 |
| Ion-Exchanged Water (added to result in 100%) | 100 |
| pH | 3.3 |

As shown in FIG. 18, large reduction in the number of bacteria/fungi was confirmed in the emulsion composition H-1 as a result of the antiseptic effects test in accordance with the Japanese Pharmacopoeia. It was thus revealed that the emulsion composition H-1 is significantly superior in antiseptic effects.

The results revealed that the present invention provides an emulsion composition having excellent antiseptic effects without using a preservative such as sodium benzoate.

Further example of the present invention is shown below.

Test Example I: Consideration of Oil/Fat Content

Preparation of Emulsion Composition

Emulsion compositions I-1 to I-10 were prepared according to the formulation shown in Table I1.

An emulsion stability test was performed using the prepared emulsion composition.

Figure 19:
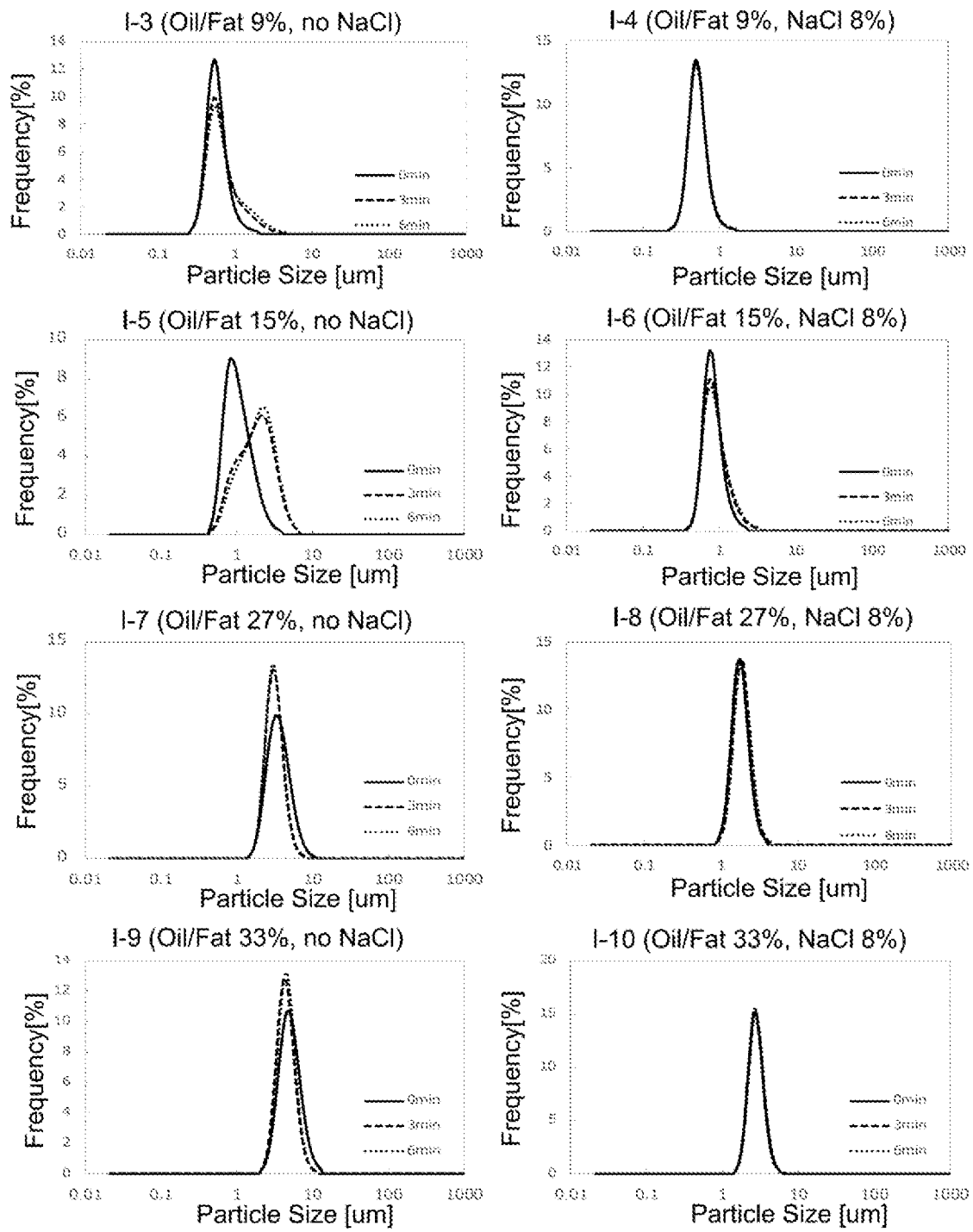
FIG. 19: Results (particle size distribution) of the emulsion physical stability test for samples I-5 to I-12 in Test Example I.

The test results for emulsifiability and emulsion storage stability are shown in Tables I2 and I3, and the results of the emulsion physical stability test are shown in FIG. 19.

The pH of emulsion compositions I-1 to I-10 was within the range of 2.5 to 3.5.

TABLE I1

| (Emulsion Composition) Formulation | Samples I-1 to I-10 Mass % |
|---|---|
| Medium-Chain Triglyceride | See Table I2 |
| GumArabic (Molecular Weight: 1.50 million) | 17.5 |
| Sodium Chloride | See Table I2 |
| Citric Acid (Anhydrous) | 0.5 |
| Propylene Glycol | 10 |
| Ion-Exchanged Water (added to result in 100%) | 100 |

TABLE I2

| | | | D50 [μm] | | 1.3 u< [%] | |
|---|---|---|---|---|---|---|
| Sample No. | Oil/Fat Content | NaCl (%) | Initial Sample | 7 Days at 60° C. | Initial Sample | 7 Days at 60° C. |
| I-1 | 3 | 0 | 0.18 | 0.24 | 0 | 1 |
| I-2 | 3 | 8 | 0.18 | 0.20 | 0 | 0 |
| I-3 | 9 | 0 | 0.52 | 0.61 | 1 | 9 |
| I-4 | 9 | 8 | 0.49 | 0.51 | 0 | 1 |
| I-5 | 15 | 0 | 0.86 | 1.09 | 16 | 38 |
| I-6 | 15 | 8 | 0.77 | 0.80 | 6 | 10 |
| I-7 | 27 | 0 | 3.31 | 3.19 | 100 | 100 |
| I-8 | 27 | 8 | 1.68 | 1.77 | 88 | 93 |
| I-9 | 33 | 0 | 5.17 | 4.74 | 100 | 100 |
| I-10 | 33 | 8 | 2.69 | 2.72 | 100 | 100 |

TABLE I3

| | | | D50 [μm] Evaluation Score (Evaluation) | | 1.3 u< [%] Evaluation Score (Evaluation) | |
|---|---|---|---|---|---|---|
| Sample No. | Oil/Fat Content | NaCl (%) | Initial Sample | 7 Days at 60° C. | Initial Sample | 7 Days at 60° C. |
| I-1 | 3 | 0 | 5 | 5 (A) | 5 | 2 (D) |
| I-2 | 3 | 8 | 5 | 5 (A) | 5 | 3 (C) |
| I-3 | 9 | 0 | 5 | 5 (A) | 5 | 3 (C) |
| I-4 | 9 | 8 | 5 | 5 (A) | 5 | 5 (A) |
| I-5 | 15 | 0 | 5 | 3 (C) | 4 | 2 (C) |
| I-6 | 15 | 8 | 5 | 5 (A) | 5 | 5 (A) |
| I-7 | 27 | 0 | 1 | 1 (—) | 1 | 1 (—) |
| I-8 | 27 | 8 | 2 | 2 (—) | 1 | 1 (—) |
| I-9 | 33 | 0 | 1 | 1 (—) | 1 | 1 (—) |
| I-10 | 33 | 8 | 1 | 1 (—) | 1 | 1 (—) |

Tables I2 and I3, and FIG. 19 revealed that the emulsion stability of the emulsion compositions with various oil and fat content was improved by adding sodium chloride.

Samples No. I-7 to I-10 contain a large amount of oils/fats. Such samples generally have difficulties in reducing the median diameter of the emulsified particles. However, as shown in Table I2, the median diameter of the emulsified particles was greatly reduced by incorporating sodium chloride. Further, FIG. 19 shows that the emulsion physical stability was improved by adding sodium chloride.

Test Example J: Consideration of Salt

Preparation of Emulsion Composition

Emulsion compositions J-1 to J-5 were prepared according to the formulation shown in Table J1.

The salt content was set so that the cation concentration was 0.5 mol/kg.

An emulsion stability test was performed using the prepared emulsion composition.

Figure 20:
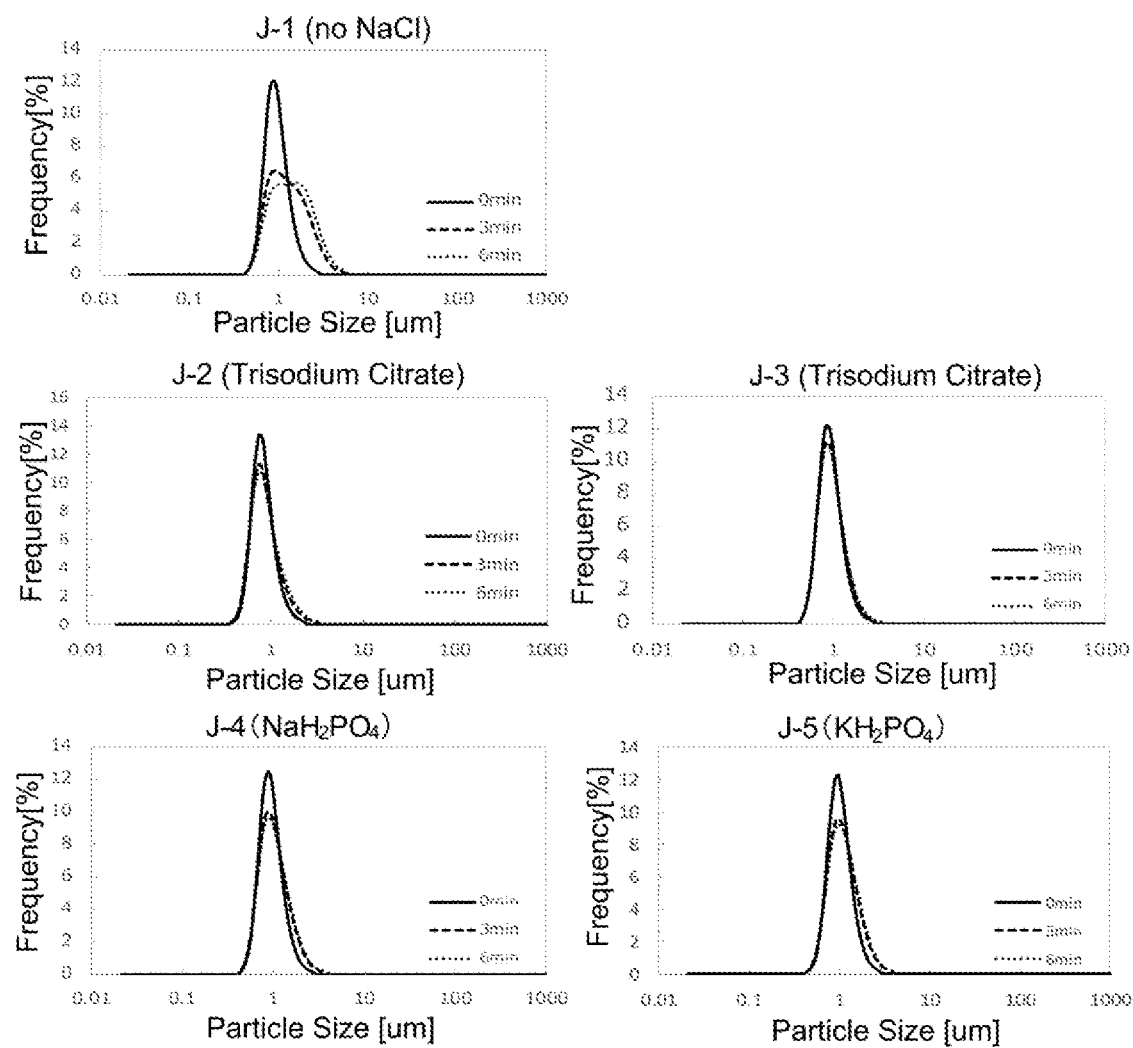
FIG. 20: Results (particle size distribution) of the emulsion physical stability test for samples J-1 to J-5 in Test Example J.

FIG. 20 shows the results of the emulsion physical stability test.

TABLE J1

| (Emulsion Compositions J-1 to J-5) Formulation | Mass % |
|---|---|
| Medium-Chain Triglyceride | 15 |
| GumArabic (Molecular Weight: 1.50 million) | 17.5 |
| Salt | See Table J2 |
| Propylene Glycol | 10 |
| Ion-Exchanged Water (added to result in 100%) | 100 |

TABLE J2

| Sample No. | Salt | Salt Content (%) | Salt Content (part) per 100 parts of GumA | pH |
|---|---|---|---|---|
| J-1 | Nil | 0 | 0 | 4.3 |
| J-2 | Trisodium Citrate (Dihydrate) | 5.0 | 28.6 | 6.3 |
| J-3 | Trisodium Citrate (Dihydrate) | 15.1 | 86.3 | 6.7 |
| J-4 | Sodium Dihydrogen Phosphate (Anhydrate) | 6.2 | 35.4 | 3.9 |
| J-5 | Potassium Dihydrogen Phosphate (Anhydrate) | 7.0 | 40 | 3.6 |

FIG. 20 shows that the emulsion stability of the emulsion composition was improved by adding an organic acid salt.

Test Example K: Desalted Gum Arabic

Preparation of Desalted Gum Arabic 100 mL of ion-exchange resin (strongly acidic cation-exchange resin Diaion SK-1B, produced by Mitsubishi Chemical Corporation) was added to 200 g of a 35 mass % gum arabic aqueous solution, and the mixture was shaken for 60 minutes. The mixed liquid after shaking was filtrated with 100-mesh filter paper to remove the ion-exchange resin, thereby preparing a desalted gum arabic aqueous solution.

Table K1 shows the analysis results (ICP analysis results) of the ion concentration before and after the treatment with the ion-exchange resin.

TABLE K1

|  | ICP Analysis [ppm] | | | |
| --- | --- | --- | --- | --- |
|  | $Na^+$ | $Mg^{2+}$ | $K^+$ | $Ca^{2+}$ |
| Before Treatment | 10 | 530 | 1800 | 1800 |
| After Treatment | 30 | 1 | 20 | 2 |

The results shown in Table K1 confirmed desalting of gum arabic.

Preparation of Emulsion Composition

Emulsion compositions K-1 to K-4 were prepared according to the formulation shown in Table K2.

TABLE K2

Figure 21:
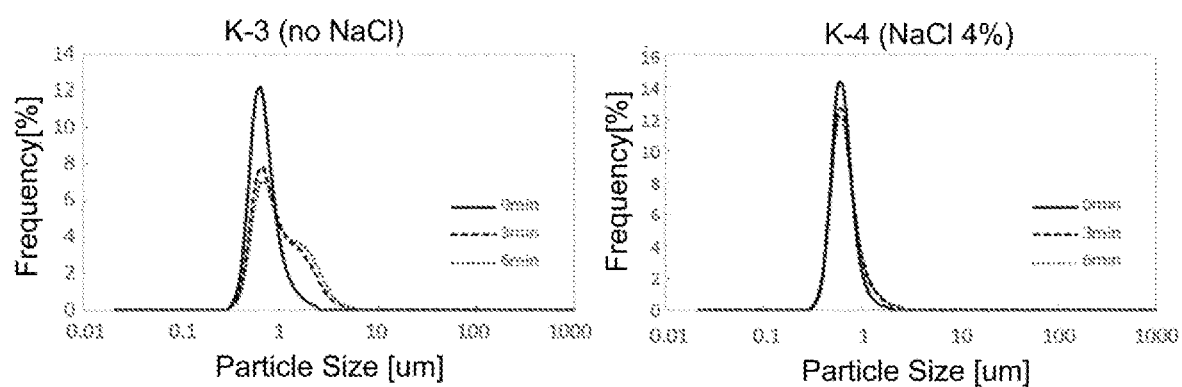
FIG. 21: Results (particle size distribution) of the emulsion physical stability test for samples K-3 to K-4 in Test Example K.

| (Emulsion Compositions K-1 to K-4) Formulation | K-1, K-2 Mass % | K-3, K-4 Mass % |
| --- | --- | --- |
| Medium-Chain Triglyceride | 12 | 12 |
| Orange Essential Oil | 1 | 1 |
| Desalted GumArabic (Molecular Weight: 1.50 million) | 15 | 15 |
| Sodium Chloride | See Table K3 | See FIG. 21 |
| 85% Phosphoric Acid | 0.5 | 0.5 |
| Propylene Glycol | 10 | — |
| Glycerin | — | 25 |
| Ion-Exchanged Water (added to result in 100%) | 100 | 100 |

An emulsion stability test was performed using the prepared emulsion composition.

Emulsion compositions K-1 and K-2 were tested for emulsifiability and emulsion storage stability, and emulsion compositions K-3 and K-4 were tested for emulsion physical stability. Tables K3 and FIG. 21 show the results.

The pH of the emulsion compositions K-1 to K-4 was within the range of 2 to 3.

TABLE K3

| | | | D50 [μm] | | 1.3 u< [%] | |
| --- | --- | --- | --- | --- | --- | --- |
| Sample No. | Polyhydric Alcohol | Polyhydric Alcohol Content (%) | NaCl (%) | Initial Sample | 7 Days at 60° C. | Initial Sample | 7 Days at 60° C. |
| K-1 | Glycerin | 25 | 0 | 0.57 | 3.00 | 1 | 100 |
| K-2 | Glycerin | 25 | 4 | 0.51 | 2.86 | 1 | 100 |

Table K3 and FIG. 21 revealed that the emulsion stability of the emulsion compositions was improved by adding sodium chloride also when desalted gum arabic was used.

Test Example L: Consideration of Gum Arabic Content

Preparation of Emulsion Composition

Emulsion compositions L-1 to L-6 were prepared according to the formulation shown in Table L1.

TABLE L1

| (Emulsion Compositions L-1 to L-6) Formulation | Mass % |
| --- | --- |
| Medium-Chain Triglyceride | 15 |
| GumArabic (Molecular Weight: 1.5 million) | See Table L2 |
| Sodium Chloride | See Table L2 |
| Citric Acid (Anhydrous) | 0.5 |
| Ion-Exchanged Water (added to result in 100%) | 100 |

An emulsion stability test was performed using the prepared emulsion composition.

Figure 22:
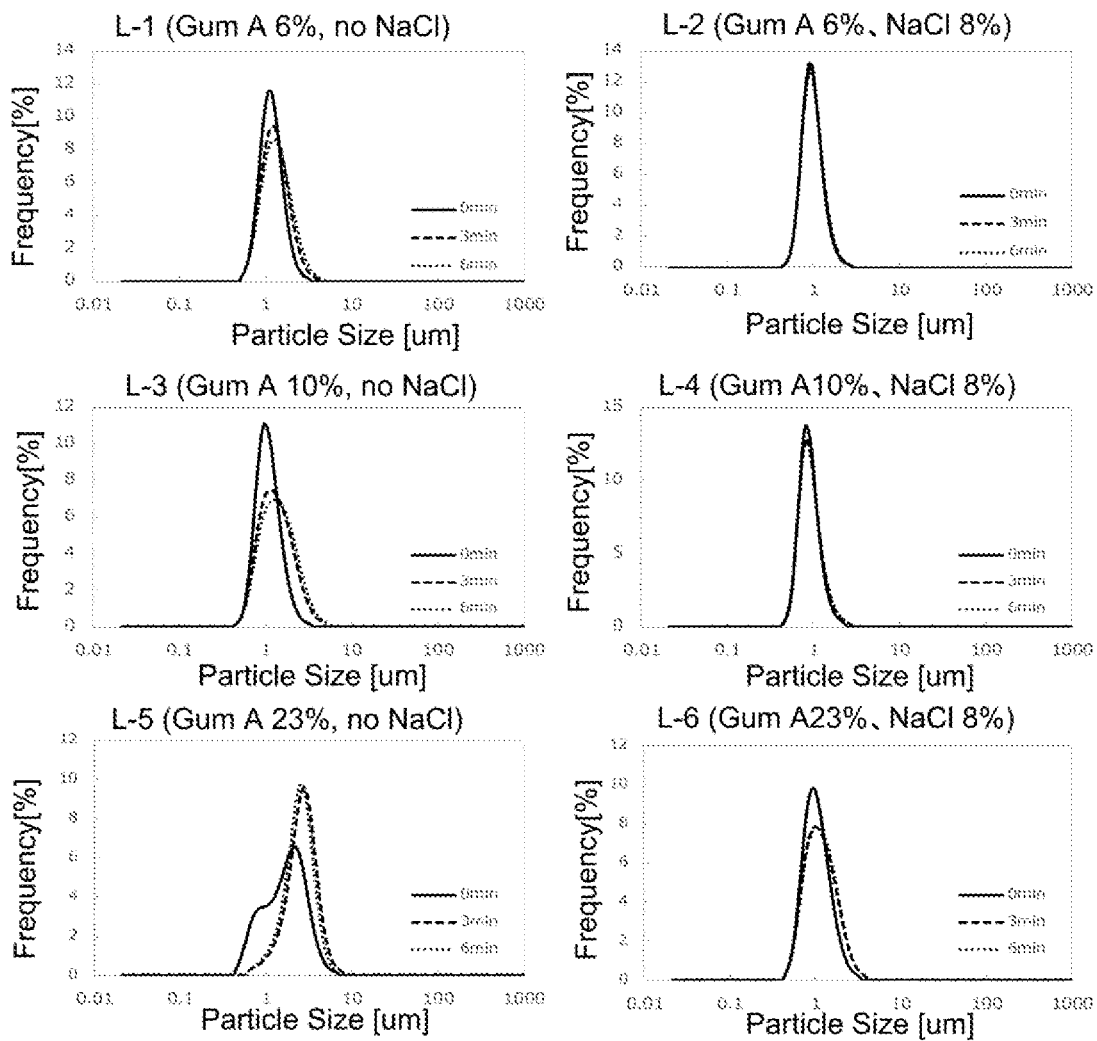
FIG. 22: Results (particle size distribution) of the emulsion physical stability test for samples L-1 to L-6 in Test Example L.

The test results for emulsifiability and emulsion storage stability are shown in Tables L2 and L3, and the results of the emulsion physical stability test are shown in FIG. 22. The pH of emulsion compositions L-1 to L-6 was within the range of 2.5 to 3.5.

TABLE L2

| | | | D50 [μm] | | 1.3 u< [%] | |
| --- | --- | --- | --- | --- | --- | --- |
| Sample No. | GumA Content | NaCl (%) | Initial Sample | 7 Days at 60° C. | Initial Sample | 7 Days at 60° C. |
| L-1 | 6 | 0 | 1.01 | 1.30 | 26 | 52 |
| L-2 | 6 | 8 | 0.91 | 0.94 | 13 | 18 |
| L-3 | 10 | 0 | 0.95 | 1.21 | 18 | 46 |
| L-4 | 10 | 8 | 0.84 | 0.85 | 8 | 10 |
| L-5 | 23 | 0 | 0.86 | 1.13 | 26 | 42 |
| L-6 | 23 | 8 | 0.93 | 0.98 | 19 | 23 |

TABLE L3

| | | | D50 [μm] | | 1.3 u< [%] | |
| --- | --- | --- | --- | --- | --- | --- |
| Sample No. | GumA Content | NaCl (%) | Initial Sample | 7 Days at 60° C. | Initial Sample | 7 Days at 60° C. |
| L-1 | 6 | 0 | 3 | 2 (B) | 3 | 1 (C) |
| L-2 | 6 | 8 | 4 | 4 (A) | 4 | 4 (A) |
| L-3 | 10 | 0 | 4 | 2 (C) | 4 | 2 (C) |
| L-4 | 10 | 8 | 5 | 5 (A) | 5 | 5 (A) |
| L-5 | 23 | 0 | 5 | 3 (C) | 3 | 2 (B) |
| L-6 | 23 | 8 | 4 | 4 (A) | 4 | 3 (B) |

Tables L2 and L3, and FIG. 22 revealed that the emulsion stability of the emulsion compositions with various gum arabic content was also improved by adding sodium chloride.

Test Example M: Gum Arabic Content (2)

Preparation of Emulsion Composition

Emulsion compositions M-1 to M-2 were prepared according to the formulation shown in Table M1.

TABLE M1

Figure 23:
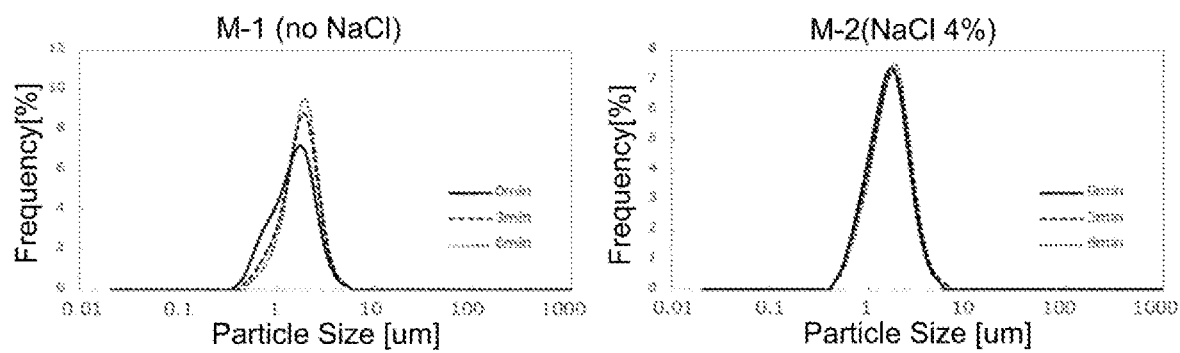
FIG. 23: Results (particle size distribution) of the emulsion physical stability test for samples M-1 to M-2 in Test Example M.

| (Emulsion Composition) Formulation | M-1 to M-2 Mass % |
|---|---|
| Medium-Chain Triglyceride | 15 |
| GumArabic (Molecular Weight: 1.50 million) | 30 |
| Sodium Chloride | See FIG. 23 |
| Citric Acid (Anhydrous) | 0.5 |
| Propylene Glycol | 5 |
| Ion-Exchanged Water (added to result in 100%) | 100 |

An emulsion stability test was performed using the prepared emulsion composition.

FIG. 23 shows the results of the emulsion physical stability test.

FIG. 23 revealed that the emulsion stability of the emulsion composition was improved by adding sodium chloride.

Test Example N: Polyhydric Alcohol Content (1)

Preparation of Emulsion Composition

Emulsion compositions N-1 to N-3 were prepared according to the formulation shown in Table N1.

TABLE N1

| (Emulsion Compositions N-1 to N-3) Formulation | Mass % |
|---|---|
| Medium-Chain Triglyceride | 12 |
| GumArabic (Molecular Weight: 1.50 million) | 17.5 |
| Sodium Chloride | 4 |
| Citric Acid (Anhydrous) | 0.5 |
| Glycerin | See Table N2 |
| Ion-Exchanged Water (added to result in 100%) | 100 |

An emulsion stability test was performed using the prepared emulsion composition.

Figure 24:
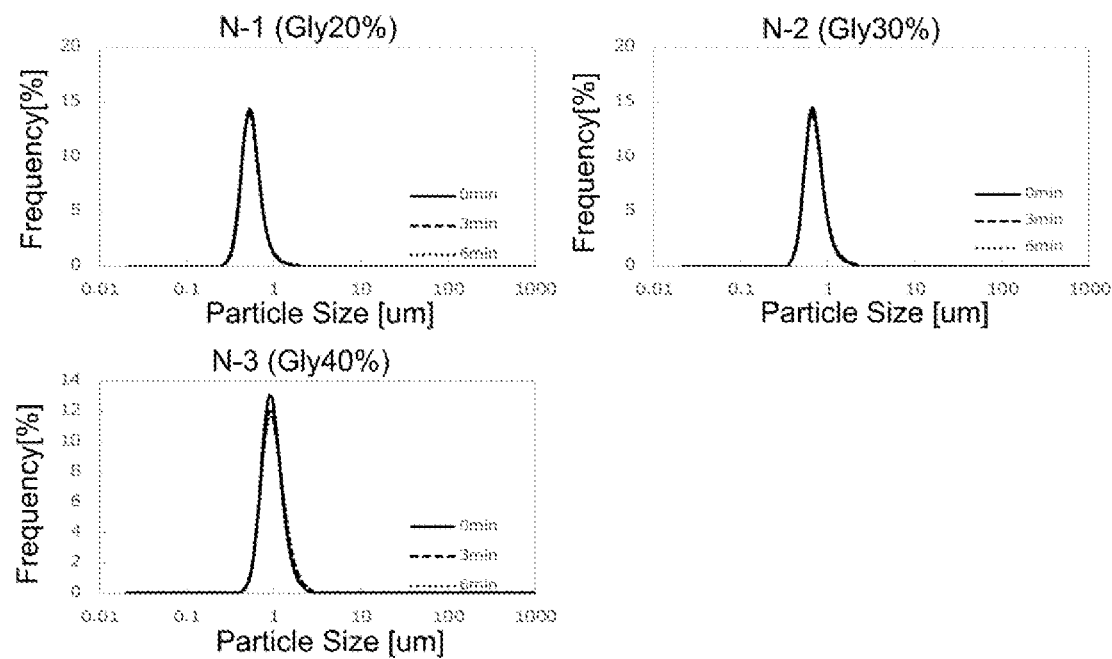
FIG. 24: Results (particle size distribution) of the emulsion physical stability test for samples N-1 to N-3 in Test Example N.

The test results for emulsifiability and emulsion storage stability are shown in Tables N2 and N3, and the results of the emulsion physical stability test are shown in FIG. 24. The pH of emulsion compositions N-1 to N-3 was within the range of 2.5 to 3.5.

TABLE N2

| | | | D50 [µm] | | 1.3 u< [%] | |
|---|---|---|---|---|---|---|
| Sample No. | Glycerin Content | NaCl (%) | Initial Sample | 7 Days at 60° C. | Initial Sample | 7 Days at 60° C. |
| N-1 | 20 | 4 | 0.53 | 0.54 | 1 | 2 |
| N-2 | 30 | 4 | 0.69 | 0.68 | 3 | 3 |
| N-3 | 40 | 4 | 0.91 | 0.89 | 13 | 12 |

TABLE N3

| | | | D50 [µm] | | 1.3 u< [%] | |
|---|---|---|---|---|---|---|
| Sample No. | Glycerin Content | NaCl (%) | Initial Sample | 7 Days at 60° C. | Initial Sample | 7 Days at 60° C. |
| N-1 | 20 | 4 | 5 | 5 (A) | 5 | 5 (A) |
| N-2 | 30 | 4 | 5 | 5 (A) | 5 | 5 (A) |
| N-3 | 40 | 4 | 4 | 5 (A) | 4 | 4 (A) |

Tables N2 and N3, and FIG. 24 revealed that emulsion compositions with excellent emulsion stability can be prepared by adding sodium chloride to emulsion compositions with various glycerin content.

Test Example O: Polyhydric Alcohol Content (2)

Preparation of Emulsion Composition

Emulsion compositions O-1 to O-6 were prepared according to the formulation shown in Table O1.

The materials (1) shown in the formulation were added to ion-exchanged water, and stirred at 3000 rpm for 5 minutes, thereby preparing a mixed liquid. Subsequently, the mixed liquid was homogenized with a high-pressure homogenizer (15MR-8TA homogenizer, produced by Manton-Gaulin Co., Ltd.) (350 kg/cm$^2$, 4 times). Materials (2) were added to the treated solution and the solution was stirred for 1 minute at 700 rpm, followed by homogenization with a high-pressure homogenizer (350 kg/cm$^2$, 1 time), thereby preparing an emulsion composition.

TABLE O1

| (Emulsion Compositions O-1 to O-6) Formulation | | Mass % |
|---|---|---|
| (1) | Medium-Chain Triglyceride | 9 |
| | GumArabic (Molecular Weight: 1.50 million) | 10.5 |
| | Sodium Chloride | See Table O2 |
| | Citric Acid (Anhydrous) | 0.3 |
| (2) | Propylene Glycol | See Table O2 |
| | Ion-Exchanged Water (added to result in 100%) | 100 |

An emulsion stability test was performed using the prepared emulsion composition.

Figure 25:
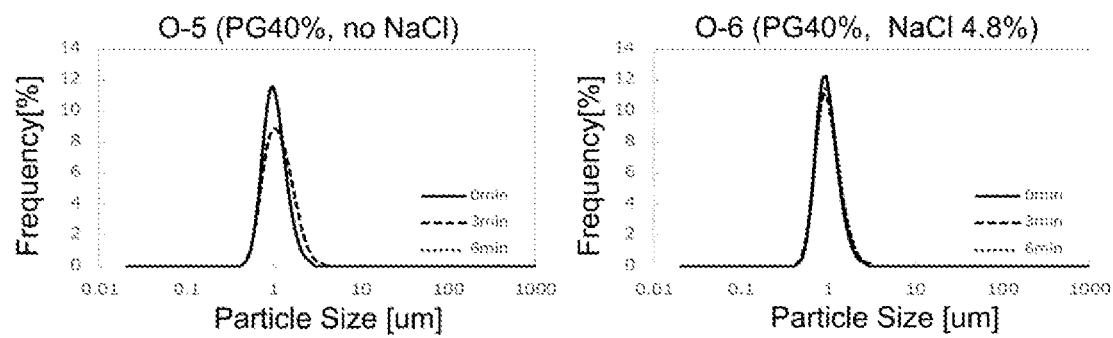
FIG. 25: Results (particle size distribution) of the emulsion physical stability test for samples O-5 and O-6 in Test Example O.

The test results for emulsifiability and emulsion storage stability are shown in Tables O2 and O3, and the results of the emulsion physical stability test are shown in FIG. 25. The pH of emulsion compositions O-1 to O-6 was within the range of 2.5 to 3.5.

TABLE O2

| | | Poly- | | D50 [µm] | | 1.3 u< [%] | |
|---|---|---|---|---|---|---|---|
| Sample No. | Poly- hydric Alcohol | hydric Alcohol Content | NaCl (%) | Initial Sample | 7 Days at 60° C. | Initial Sample | 7 Days at 60° C. |
| O-1 | PG | 20 | 0 | 0.62 | 0.78 | 2 | 15 |
| O-2 | PG | 20 | 4.8 | 0.60 | 0.67 | 2 | 6 |
| O-3 | PG | 30 | 0 | 0.70 | 1.38 | 4 | 57 |
| O-4 | PG | 30 | 4.8 | 0.73 | 1.07 | 5 | 36 |
| O-5 | PG | 40 | 0 | 0.94 | 2.09 | 17 | 97 |
| O-6 | PG | 40 | 4.8 | 0.85 | 1.79 | 14 | 94 |

TABLE O3

| Sample No. | Polyhydric Alcohol | Polyhydric Alcohol Content | NaCl (%) | D50 [μm] Initial Sample | D50 [μm] 7 Days at 60° C. | 1.3 u< [%] Initial Sample | 1.3 u< [%] 7 Days at 60° C. |
|---|---|---|---|---|---|---|---|
| O-1 | PG | 20 | 0 | 5 | 5 (A) | 5 | 4 (B) |
| O-2 | PG | 20 | 4.8 | 5 | 5 (A) | 5 | 5 (A) |
| O-3 | PG | 30 | 0 | 5 | 2 (D) | 5 | 1 (D) |
| O-4 | PG | 30 | 4.8 | 5 | 3 (C) | 5 | 2 (D) |
| O-5 | PG | 40 | 0 | 4 | 1 (D) | 4 | 1 (D) |
| O-6 | PG | 40 | 4.8 | 5 | 2 (D) | 4 | 1 (D) |

Tables O2 and O3, and FIG. 25 revealed that the emulsion stability of the emulsion compositions with various polyhydric alcohols was improved by adding sodium chloride.

Test Example P: Polyhydric Alcohol Content (3)

Preparation of Emulsion Composition

Emulsion compositions P-1 to P-4 were prepared in the same manner as in Test Example O according to the formulation shown in Table P1.

TABLE P1

Figure 26:
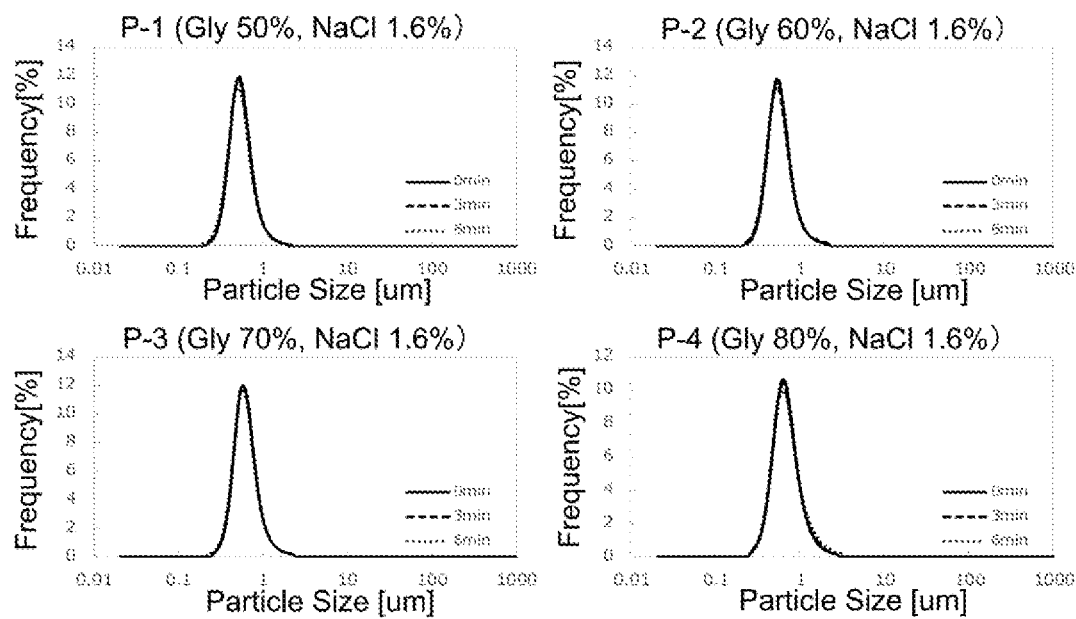
FIG. 26: Results (particle size distribution) of the emulsion physical stability test for samples P-1 to P-4 in Test Example P.

| (Emulsion Compositions P-1 to P-4) Formulation | | Mass % |
|---|---|---|
| (1) | Medium-Chain Triglyceride | 4 |
| | GumArabic (Molecular Weight: 1.50 million) | 10 |
| | Sodium Chloride | 1.6 |
| | Citric Acid (Anhydrous) | 0.1 |
| (2) | Glycerin | See FIG. 26 (50, 60, 70, 80) |
| | Ion-Exchanged Water (added to result in 100%) | 100 |

An emulsion stability test was performed using the prepared emulsion composition.

FIG. 26 shows the results of the emulsion physical stability test.

The pH of emulsion compositions P-1 to P-4 was within the range of 2.5 to 3.5.

FIG. 26 revealed that preparation of emulsion compositions superior in emulsion stability with various glycerin content is possible by adding sodium chloride.

Test Example Q: Consideration of pH

Preparation of Emulsion Composition

Emulsion compositions Q-1 to Q-5 were prepared according to the formulation shown in Table Q1. The pH of the emulsion compositions was adjusted to those shown in Table Q2 using HCl or NaOH.

TABLE Q1

| (Emulsion Compositions Q-1 to Q-5) Formulation | Mass % |
|---|---|
| Medium-Chain Triglyceride | 15 |
| GumArabic (Molecular Weight: 1.50 million) | 17.5 |
| Sodium Chloride | 3 |
| Ion-Exchanged Water (added to result in 100%) | 100 |

An emulsion stability test was performed using the prepared emulsion composition. The results for emulsion stability test are shown in Tables Q2 and Q3.

TABLE Q2

| Sample No. | pH | NaCl (%) | D50 [μm] Initial Sample | D50 [μm] 3 Days at 60° C. | 1.3 u< [%] Initial Sample | 1.3 u< [%] 3 Days at 60° C. |
|---|---|---|---|---|---|---|
| Q-1 | 2.4 | 3 | 0.72 | 0.76 | 5 | 10 |
| Q-2 | 2.9 | 3 | 0.74 | 0.78 | 6 | 12 |
| Q-3 | 3.9 | 3 | 0.86 | 0.92 | 12 | 22 |
| Q-4 | 5.1 | 3 | 0.80 | 0.84 | 7 | 15 |
| Q-5 | 6.3 | 3 | 0.77 | 0.89 | 6 | 27 |

TABLE Q3

| Sample No. | pH | NaCl (%) | D50 [μm] Initial Sample | D50 [μm] 3 Days at 60° C. | 1.3 u< [%] Initial Sample | 1.3 u< [%] 3 Days at 60° C. |
|---|---|---|---|---|---|---|
| Q-1 | 2.4 | 3 | 5 | 5 (A) | 5 | 5 (A) |
| Q-2 | 2.9 | 3 | 5 | 5 (A) | 5 | 4 (B) |
| Q-3 | 3.9 | 3 | 5 | 4 (B) | 4 | 3 (B) |
| Q-4 | 5.1 | 3 | 5 | 5 (A) | 5 | 4 (B) |
| Q-3 | 6.3 | 3 | 5 | 5 (A) | 5 | 3 (C) |

Tables Q2 and Q3 revealed that preparation of emulsion compositions superior in emulsion stability with various pH is possible by adding sodium chloride.

Test Example R: Consideration of Powderization

Preparation of Emulsion Composition

Emulsion compositions R-1 to R-2 were prepared according to the formulation shown in Table R. The pH of the emulsion compositions was within the range of 2.5 to 3.5. The prepared emulsion compositions were spray-dried using a spray dryer (APV Nordic Anhydro) at an inlet temperature of 160° C. and an outlet temperature of 85-90° C. at 20000 rpm, thereby obtaining a powdery emulsion composition.

Table R2 shows the final formulation of the powdery emulsion composition.

TABLE R1

| (Emulsion Composition) Formulation | R-1 Mass % | R-2 Mass % |
|---|---|---|
| Medium-Chain Triglyceride | 12 | 12 |
| GumArabic (Molecular Weight: 1.5 million) | 10.5 | 10.5 |
| Sodium Chloride | — | 2 |
| Citric Acid (Anhydrous) | 0.5 | 0.5 |
| Dextrin | 17 | 17 |
| Ion-Exchanged Water (added to result in 100%) | 100 | 100 |

TABLE R2

| (Powdery Emulsion Composition) Formulation | R-1 Mass % | R-2 Mass % |
|---|---|---|
| Medium-Chain Triglyceride | 30 | 30 |
| GumArabic (Molecular Weight: 1.50 million) | 26.25 | 26.25 |
| Sodium Chloride | 0 | 5 |
| Citric Acid (Anhydrous) | 1.25 | 1.25 |
| Dextrin | 42.5 | 37.5 |
| Total | 100 | 100 |

An emulsion stability test was performed using the prepared powdery emulsion composition.

Emulsion Stability Test

An aqueous solution was prepared by diluting the powdery emulsion composition with ion-exchanged water, and the emulsion stability of the resulting aqueous solution was tested. Table R3 shows the results.

In Table R3, "Initial Sample" shows the results of the powdery emulsion composition immediately after the preparation. "Powder (Plastic Bag)" shows the results of storing the powdery emulsion composition in a polyethylene bag (Product Name: Unipack E-8, Seisannipponsha Ltd., capacity=20 g) at 60° C. for seven days.

"Powder (aluminum vapor deposition)" shows the results of 7 days storage of a powdery emulsion composition placed and sealed in a zippered AL/PET laminate film (product name: Lamizip, AL-10, Seisannipponsha Ltd., capacity=20 g) at 60° C.

TABLE R3

| Sample No. | NaCl (%) | Initial Sample D50 [nm] | Initial Sample 1.3 u< [%] | Powder (Plastic Bag) D50 [μm] | Powder (Plastic Bag) 1.3 u< [%] | Powder (Aluminum Vapor Deposition) D50 [μm] | Powder (Aluminum Vapor Deposition) 1.3 u< [%] |
|---|---|---|---|---|---|---|---|
| R-1 | 0 | 0.86. | 29 | 1.01 | 39 | 1.30 | 51 |
| R-2 | 5 | 0.76 | 23 | 0.82 | 30 | 0.91 | 36 |

Table R3 revealed that the emulsion stability of the powdery emulsion composition was improved by adding sodium chloride.

Test Example S: Consideration of Oil Phase Content

Preparation of Emulsion Composition

An emulsion composition was prepared according to the formulation shown in Table S1.

An emulsion stability test was performed using the prepared emulsion composition.

Figure 27:
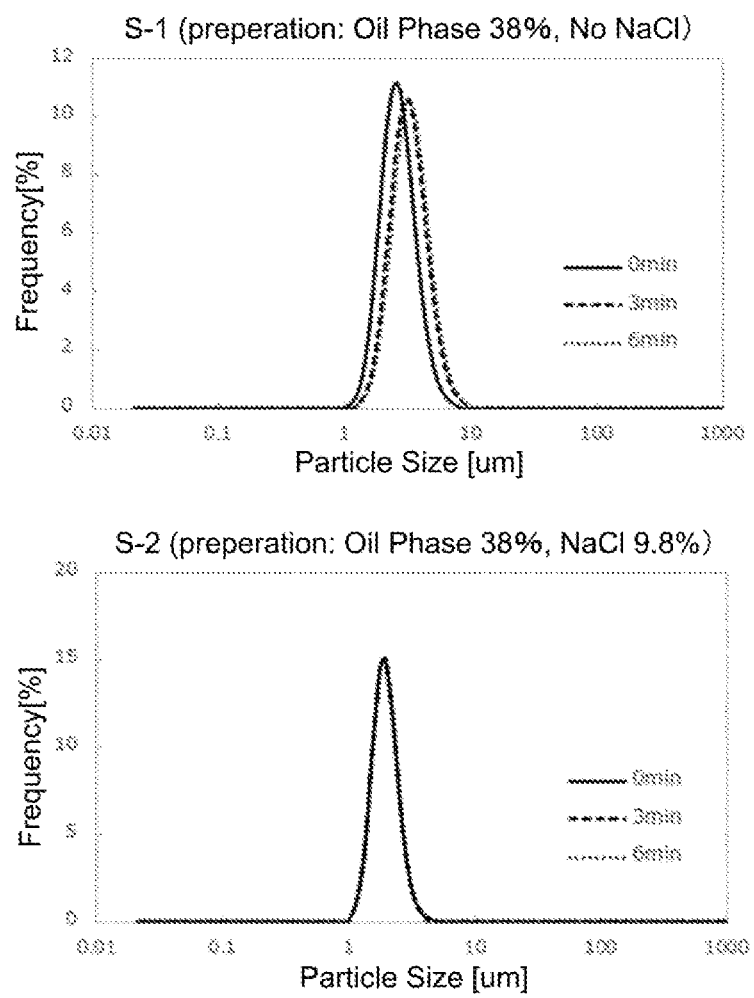
FIG. 27: Results (particle size distribution) of the emulsion physical stability test for samples S-1 to S-2 in Test Example S.

The test results for emulsifiability and emulsion storage stability are shown in Table S2, and the results of the emulsion physical stability test are shown in FIG. 27.

The pH of emulsion compositions S-1 and S-2 was within the range of 2.5 to 3.5.

TABLE S1

| Formulation | Mass % |
|---|---|
| Medium-Chain Triglyceride | 38 |
| GumArabic (Molecular Weight: 150 × 10$^4$) | 12 |
| Sodium Chloride | See Table S2 |
| Citric Acid (Anhydrous) | 0.5 |
| Propylene Glycol | 5 |
| Ion-Exchanged Water (added to result in 100%) | 100 |

TABLE S2

| Sample No. | Oil/Fat Content | NaCl (%) | D50 [μm] Initial Sample | D50 [μm] 7 Days at 60° C. | 1.3 u< [%] Initial Sample | 1.3 u< [%] 7 Days at 60° C. |
|---|---|---|---|---|---|---|
| S-1 | 38 | 0 | 2.20 | 3.24 | 98 | 100 |
| S-2 | 38 | 9.8 | 1.83 | 1.94 | 95 | 98 |

Table S2 revealed that the emulsion stability of the emulsion composition was improved by adding sodium chloride also when the oil/fat content was large, i.e., 38%. Further, FIG. 27 shows that the emulsion physical stability was improved by adding sodium chloride.

The invention claimed is:

1. An emulsion composition comprising:
water;
an oily component;
gum arabic having a weight average molecular weight of not less than 1 million; and
a salt,
wherein the salt content in the emulsion composition is 1.5 to 8 mass %,
wherein the salt is at least one inorganic salt selected from the group consisting of sodium chloride, potassium chloride, calcium chloride, and magnesium chloride,
wherein the salt content is 90 parts by mass or less per 100 parts by mass of the gum arabic,
wherein the emulsion composition has a pH in the range of 2 to 4.5, and
wherein the weight average molecular weight of the gum arabic is determined by using gel filtration chromatography and a multi-angle laser light scattering detector (GPC-MALLS).

2. An aqueous composition comprising the emulsion composition according to claim 1.

3. A food or drink comprising the emulsion composition according to claim 1.

4. The food or drink according to claim 3, wherein the food or drink is a drink.

5. A method for improving the emulsion stability of an emulsion composition comprising
water,
an oily component, and
gum arabic having a weight average molecular weight of not less than 1 million,
the method comprising incorporating a salt into the composition,
wherein the salt content in the emulsion composition is 1.5 to 8 mass %,
wherein the salt is at least one inorganic salt selected from the group consisting of sodium chloride, potassium chloride, calcium chloride, and magnesium chloride,
wherein the emulsion composition has a pH in the range of 2 to 4.5,
wherein the salt content is 90 parts by mass or less per 100 parts by mass of the gum arabic, and
wherein the weight average molecular weight of the gum arabic is determined by using gel filtration chromatography and a multi-angle laser light scattering detector (GPC-MALLS).

6. The emulsion composition according to claim 1, wherein the oily component determines whether the emulsion composition is an emulsified flavoring preparation, emulsified colorant preparation, emulsified nutrition fortifier preparation, emulsified functional material preparation, or clouding agent.

* * * * *